United States Patent
Brunette et al.

(10) Patent No.: US 10,450,314 B2
(45) Date of Patent: *Oct. 22, 2019

(54) PTERIDINE DERIVATIVES AS MODULATORS OF ROR GAMMA

(71) Applicants: Boehringer Ingelheim International GmbH, Ingelheim am Rhein (DE); Steven Richard Brunette, New Milford, CT (US); Johanna Csengery, New Fairfield, CT (US); Robert Owen Hughes, Newtown, CT (US); Xiang Li, New Milford, CT (US); Robert Sibley, North Haven, CT (US); Michael Robert Turner, Danbury, CT (US); Zhaoming Xiong, Ridgefield, CT (US)

(72) Inventors: Steven Richard Brunette, New Milford, CT (US); Johanna Csengery, New Fairfield, CT (US); Robert Owen Hughes, Newtown, CT (US); Xiang Li, New Milford, CT (US); Robert Sibley, North Haven, CT (US); Michael Robert Turner, Danbury, CT (US); Zhaoming Xiong, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/763,690

(22) PCT Filed: Sep. 28, 2016

(86) PCT No.: PCT/US2016/054040
§ 371 (c)(1),
(2) Date: Mar. 27, 2018

(87) PCT Pub. No.: WO2017/058831
PCT Pub. Date: Apr. 6, 2017

(65) Prior Publication Data
US 2018/0298005 A1    Oct. 18, 2018

Related U.S. Application Data

(60) Provisional application No. 62/235,610, filed on Oct. 1, 2015.

(51) Int. Cl.
*C07D 475/00* (2006.01)
*A61K 31/519* (2006.01)
*C07D 475/10* (2006.01)

(52) U.S. Cl.
CPC ......... *C07D 475/00* (2013.01); *A61K 31/519* (2013.01); *C07D 475/10* (2013.01)

(58) Field of Classification Search
CPC .................... C07D 475/00; A61K 31/519
See application file for complete search history.

(56) References Cited

U.S. PATENT DOCUMENTS

| 2015/0291607 A1 | 10/2015 | Bakonyi et al. |
| 2016/0075706 A1 | 3/2016 | Bakonyi et al. |
| 2016/0159791 A1 | 6/2016 | Cook et al. |

FOREIGN PATENT DOCUMENTS

| WO | 2015017335 A1 | 2/2015 |
| WO | 2015160654 A1 | 10/2015 |

OTHER PUBLICATIONS

Rosenblum, Treating Human Autoimmunity: Current Practice and Future Prospects, Sci Transl Med, vol. 4, No. 125, p. 1-20. (Year: 2012).*
Larsen, Allergy immunotherapy: The future of allergy treatment, Drug Discovery Today, vol. 21, No. 1, p. 26-37. (Year: 2016).*
Hughes et al., "Investigation of 1-8 aminopyridiopyrazinones as PDE5 inhibitors: Evaluation of modifications to the central ring system", Bioorganic & Medicinal Chemistry Letters, 2009, vol. 19, No. 15, pp. 4092-4096.
International Search Report and Written Opinion for corresponding PCT/US2016/054040, dated Nov. 13, 2016.

* cited by examiner

*Primary Examiner* — Karen Cheng
(74) *Attorney, Agent, or Firm* — Philip I. Datlow

(57) ABSTRACT

The present invention encompasses compounds of formula (I) wherein the variables are defined herein which are suitable for the modulation of RORγ and the treatment of diseases related to the modulation of RORγ. The present invention also encompasses processes of making compounds of formula (I) and pharmaceutical preparations containing them.

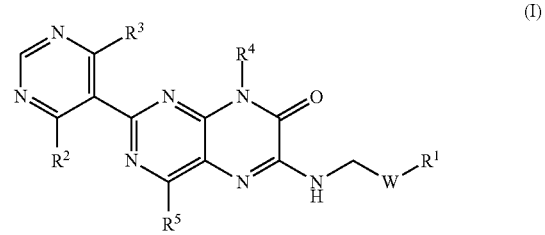

(I)

9 Claims, No Drawings

PTERIDINE DERIVATIVES AS MODULATORS OF ROR GAMMA

BACKGROUND OF THE INVENTION

Technical Field

The present invention relates to novel compounds which modulate the activity of RORγ and their use as medicaments.

Background

RORγ (retinoic acid receptor related orphan receptor gamma) (also referred to as "RORγt") is a transcription factor belonging to the steroid hormone receptor superfamily (reviewed in Jetten 2006. Adv. Dev Biol. 16: 313-355.). RORγ has been identified as a transcriptional factor that is required for the differentiation of T cells and secretion of Interleukin 17 (IL-17) from a subset of T cells termed $Th_{17}$ cells (Ivanov, Cell 2006, 126, 1121-1133). The rationale for the use of a RORγ targeted therapy for the treatment of chronic inflammatory diseases is based on the emerging evidence that $Th_{17}$ cells and the cytokine IL-17 contribute to the initiation and progression of the pathogenesis of several autoimmune diseases including psoriasis, ankylosing spondylitis, rheumatoid arthritis, multiple sclerosis and Crohn's disease (reviewed in Miossec, Nature Drug Discovery 2012, 11, 763-776; see also Khan et al., Bioorganic & Medicinal Chemistry Letters 23 (2013), 532-536). The outcome of recent clinical trials with neutralizing antibodies to IL-17 and its receptor IL-17RA (Leonardi 2012, New England Journal of Medicine, 366, 1190-1199; Papp 2012, New England Journal of Medicine 366, 1181-1189) in psoriasis highlight the role of IL-17 in the pathogenesis of this disease. As such, attenuation of IL-17 secretion from activated $Th_{17}$ T cells via inhibition of RORγ may offer similar therapeutic benefit.

SUMMARY OF THE INVENTION

The invention comprises a novel class of heteroaromatic compounds and methods for making and using the same, said compounds having the general structure of formula (I), wherein the substituent groups are as herein defined:

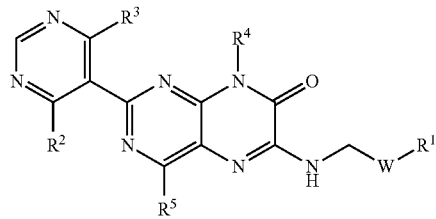

(I)

These compounds are useful for the treatment of autoimmune and allergic disorders in that they exhibit potent inhibitory activity against RORγ.

In a further aspect, a goal of the present invention is to provide compounds with metabolic stability properties consistent with acceptable pharmacokinetic properties. As is known in the art, compounds having poor metabolic stability may not readily achieve desirable therapeutic levels. The preferred compounds of the present invention would be expected to have metabolic stability properties consistent with being a suitable drug.

DETAILED DESCRIPTION OF THE INVENTION

Definitions and Conventions Used

Terms that are not specifically defined here have the meanings that would be apparent to a person skilled in the art, in light of the overall disclosure and the context as a whole.

As used herein, the following definitions apply, unless stated otherwise:

The use of the prefix $C_{x-y}$, wherein x and y each represent a natural number, indicates that the chain or ring structure or combination of chain and ring structure as a whole, specified and mentioned in direct association, may consist of a maximum of y and a minimum of x number of carbon atoms.

In general, for groups comprising two or more subgroups, unless otherwise indicated the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached. However, if a bond is depicted just prior to the first named subgroup, then that first named subgroup is the radical attachment point, for example, the substituent "—S(O)$_n$C$_{1-6}$alkyl" means a $C_{1-6}$-alkyl-group which is bound to an S(O)$_n$ group, the latter of which is bound to the core or to the group to which the substituent is attached.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

For example, the term "$C_{1-5}$alkyl" includes for example H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Further examples of alkyl are methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 2,2-dimethyl-1-propyl(neo-pentyl; —CH$_2$C(CH$_3$)$_3$), 2-methyl-1-butyl (—CH$_2$CH(CH$_3$)CH$_2$CH$_3$), 1-hexyl (n-hexyl; —CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$), 2,3-dimethyl-1-butyl (—CH$_2$CH(CH$_3$)CH(CH$_3$) CH$_3$), 2,2-dimethyl-1-butyl (—CH$_2$C(CH$_3$)$_2$CH$_2$CH$_3$), 3,3-dimethyl-1-butyl (—CH$_2$CH$_2$C(CH$_3$)$_3$), 2-methyl-1-pentyl (—CH$_2$CH(CH$_3$)CH$_2$CH$_2$CH$_3$), 3-methyl-1-pentyl (—CH$_2$CH$_2$CH(CH$_3$)CH$_2$CH$_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example C$_{x-y}$alkylamino or C$_{x-y}$alkoxy.

Unlike alkyl, alkenyl, when used alone or in combination, consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed. Alkenyl may optionally be present in the cis or trans or E or Z orientation with regard to the double bond(s).

Unlike alkyl, alkynyl, when used alone or in combination, consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Haloalkyl (haloalkenyl, haloalkynyl), when used alone or in combination, is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —CF$_3$, —CHF$_2$, —CH$_2$F, —CF$_2$CF$_3$, —CHFCF$_3$, —CH$_2$CF$_3$, —CF$_2$CH$_3$, —CHFCH$_3$, —CF$_2$CF$_2$CF$_3$, —CF$_2$CH$_2$CH$_3$, —CF=CF$_2$, —CCl=CH$_2$, —CBr=CH$_2$, —C≡C—CF$_3$, —CHFCH$_2$CH$_3$, —CHFCH$_2$CF$_3$ etc.

Halogen relates to fluorine, chlorine, bromine and/or iodine atoms.

The term "cycloalkyl", when used alone or in combination, refers to a nonaromatic 3 to 12-membered (but preferably, 3 to 6-membered) monocyclic carbocyclic radical or a nonaromatic 6 to 10-membered fused bicyclic, bridged bicyclic, propellane or spirocyclic carbocyclic radical. The C$_{3-12}$ cycloalkyl may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[1.1.1]pentane, bicyclo[3.3.0]octane, bicyclo [4.3.0]nonane, and bicyclo[4.4.0]decanyl (decahydronaphthalenyl). Non-limiting examples of 6 to 10-membered bridged bicyclic carbocyclic radicals include bicyclo[2.2.2] heptanyl, bicyclo[2.2.2]octanyl, and bicyclo[3.2.1]octanyl. Non-limiting examples of 6 to 10-membered propellane carbocyclic radicals include but are not limited to [1.1.1.] propellane, [3.3.3]propellane and [3.3.1]propellane. Non-limiting examples of 6 to 10-membered spirocyclic carbocyclic radicals include but are not limited to spiro[3,3] heptanyl, spiro[3,4]octanyl and spiro[4,4]heptanyl.

The term "heterocyclyl", when used alone or in combination, refers to a heterocyclic ring system that contains 2-10 carbon atoms and one to four heteroatom ring atoms chosen from NH, NR', oxygen and sulfur wherein R' is C$_{1-6}$ alkyl. The term "heterocyclyl" includes stable nonaromatic 4-8 membered monocyclic heterocyclic radicals or a stable nonaromatic 6 to 11-membered fused bicyclic, bridged bicyclic or spirocyclic heterocyclic radical. The heterocycle may be either completely saturated or partially unsaturated. In one embodiment the heterocycle is a C$_{3-6}$ heterocycle, i.e., containing 3 to 6 ring carbon atoms. Non-limiting examples of nonaromatic monocyclic heterocyclic radicals include tetrahydrofuranyl, azetidinyl, pyrrolidinyl, pyranyl, tetrahydropyranyl, dioxanyl, thiomorpholinyl, 1,1-dioxo-1.lamda$_6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1] heptanyl, 3-azabicyclo[3.1.0]hexanyl, and 3-azabicyclo [3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. Sulfur and nitrogen may optionally be present in all the possible oxidation stages (for example, sulfur: sulfoxide —SO—, sulfone —SO$_2$—; nitrogen: N-oxide).

The term "aryl", when used alone or in combination, refers to an aromatic hydrocarbon ring containing from six to fourteen carbon ring atoms (e.g., a C$_{6-14}$ aryl, preferably C$_6$-10 aryl). The term C$_{6-14}$ aryl includes monocyclic rings, fused rings and bicyclic rings where at least one of the rings is aromatic. Non-limiting examples of C$_{6-14}$ aryls include phenyl, indanyl, indenyl, benzocyclobutanyl, dihydronaphthyl, tetrahydronaphthyl, naphthyl, benzocycloheptanyl and benzocycloheptenyl.

As used herein, the term "heteroaryl", when used alone or in combination, refers to a heteroaromatic ring system that contains 2-10 carbon atoms and 1-4 heteroatom ring atoms selected from N, NH, NR', O and S wherein R' is C$_{1-6}$ alkyl. The term "heteroaryl" includes aromatic 5 to 6-membered monocyclic heteroaryls and aromatic 7 to 11-membered heteroaryl bicyclic or fused rings where at least one of the rings is aromatic. Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic or fused rings include benzimidazolyl, 1,3-dihydrobenzoimidazol-2-one, quinolinyl, dihydro-2H-quinolinyl, isoquinolinyl, quinazolinyl, indazolyl, thieno[2,3-d]pyrimidinyl, indolyl, isoindolyl, indazolyl, benzotriazolyl, benzofuranyl, benzopyranyl, benzodioxolyl, benzoxazolyl, benzothiazolyl, pyrrolo[2,3-b]pyridinyl, and imidazo[4,5-b] pyridinyl. Sulfur and nitrogen may optionally be present in all the possible oxidation stages (for example, sulphur: sulfoxide —SO—, sulfone —SO$_2$—; nitrogen: N-oxide).

The compounds of the invention are only those which are contemplated to be chemically stable as will be appreciated by those skilled in the art. For example, a compound which would have a "dangling valency", or a carbanion are not compounds contemplated by the inventive methods disclosed herein.

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof, and their corresponding unsolvated as well as solvated forms with pharmaceutically acceptable solvents such as water, ethanol and the like.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio. Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

By a therapeutically effective amount for the purposes of this invention is meant a quantity of substance that is capable of obviating symptoms of illness or alleviating these symptoms, or which prolong the survival of a treated patient.

Embodiments of the Invention

A general embodiment of the invention is directed to a compound of formula (I) below:

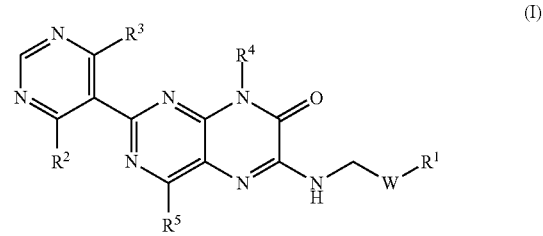

wherein:
$R^1$ is selected from —S(O)$_n$R$^6$, —S(O)$_n$NR$^7$R$^8$, and —S(O)(NH)R$^6$;
  wherein:
  R$^6$ is:
  C$_{1-3}$ alkyl
  R$^7$ and R$^8$ are each —H; and
  n is 1 or 2;
R$^2$ and R$^3$ are independently selected from
C$_{1-3}$alkyl;
cyclopropyl; and
methoxy;
R$^4$ is C$_{1-6}$alkyl, optionally substituted with one or two groups independently selected from
C$_{3-6}$cycloalkyl;
halogen;
—CF$_3$; and
—CN;
R$^5$ is selected from
C$_{1-3}$alkyl, optionally substituted with 1 to 3 fluoro groups;
—CH$_2$OH;
—CH$_2$OC(O)C$_{1-3}$alkyl; and
—OC$_{1-3}$alkyl;
W is selected from
pyridinyl;
pyrimidinyl;
pyrizinyl;
phenyl; and
piperidinyl;
and the pharmaceutically acceptable salts thereof.

In another embodiment, there are provided compounds of the formula (I) as described according to the embodiment above and wherein
R$^1$ is selected from —S(O)$_{nR6}$, —S(O)$_n$NR$^7$R$^8$, and —S(O)(NH)R$^6$;
wherein:
  R$^6$ is C$_{1-3}$ alkyl;
  R$^7$ and R$^8$ are each —H; and
  n is 2;
R$^2$ and R$^3$ are independently selected from
methyl;
cyclopropyl; and
methoxy;

R⁴ is C₄alkyl, optionally substituted with one or two groups independently selected from cyclopropyl;
—F;
—CF₃; and
—CN;
R⁵ is selected from
—CH₃;
—CH₂F;
—CH₂OH;
—CH₂OC(O)CH₃; and
—OCH₃;
W is selected from
2-pyridinyl, 3-pyridinyl, 2-pyrimidinyl, 2-pyrizinyl and phenyl;
and the pharmaceutically acceptable salts thereof.

In another embodiment, there are provided compounds of the formula (I) as described according to any of the embodiments above and wherein
R¹ is selected from —S(O)ₙR⁶, —S(O)ₙNR⁷R⁸, and —S(O)(NH)R⁶;
wherein:
R⁶ is C₁₋₂ alkyl;
R⁷ and R⁸ are each —H; and
n is 2;
R² and R³ are independently selected from
methyl;
cyclopropyl; and
methoxy;
R⁴ is C₄alkyl, optionally substituted with one or two groups independently selected from
cyclopropyl;
—F;
—CF₃; and
—CN;
R⁵ is selected from
—CH₃;
—CH₂F;
—CH₂OH;
—CH₂OC(O)CH₃; and
—OCH₃;
W is selected from
2-pyridinyl, 3-pyridinyl, 2-pyrimidinyl, 2-pyrizinyl and phenyl;
and the pharmaceutically acceptable salts thereof.

In another embodiment, there are provided compounds of the formula (I) as described according to any of the embodiments above and wherein
R¹ is selected from —S(O)ₙR⁶, —S(O)ₙNR⁷R⁸, and —S(O)(NH)R⁶;
wherein:
R⁶ is C₁₋₂ alkyl;
R⁷ and R⁸ are each —H; and
n is 2;
R² is methyl or methoxy;
R³ is cyclopropyl;
R⁴ is C₁₋₄alkyl, optionally substituted with a group selected from cyclopropyl and —CF₃;
R⁵ is selected from
—CH₃;
—CH₂F; and
—CH₂OH;
W is selected from
2-pyridinyl, 3-pyridinyl, 2-pyrimidinyl, and phenyl;
and the pharmaceutically acceptable salts thereof.

In another embodiment, there are provided compounds of the formula (I) as described according to any of the embodiments above and wherein
R² is methyl or methoxy;
R³ is cyclopropyl;
R⁴ is C₁₋₄alkyl, optionally substituted with a group selected from cyclopropyl and —CF₃;
R⁵ is —CH₃;
W is selected from
2-pyridinyl, 3-pyridinyl, 2-pyrimidinyl, and phenyl;
and the pharmaceutically acceptable salts thereof.

In another embodiment, there are provided compounds of the formula (I) as described according to any of the embodiments above and wherein
W is selected from 2-pyridinyl and, 3-pyridinyl;
and the pharmaceutically acceptable salts thereof.

In another aspect of the invention, there is provided a compound of the general formula (I) according to any of the embodiments above, or a pharmaceutically acceptable salt thereof for use in a therapeutic method as described hereinbefore and hereinafter.

Table 1 shows representative compounds of the invention which can be made by the methods described in the general synthetic schemes, the examples, and known methods in the art.

TABLE 1

| Example | Structure | RT | m/z [M + H]⁺ | HPLC Method |
| --- | --- | --- | --- | --- |
| 1 | 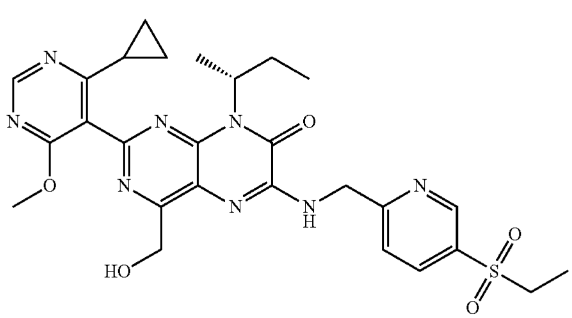 [SMILES: CC[C@@H](C)n1c(=O)c(NCc2ccc(S(=O)(=O)CC)cn2)nc2c(CO)nc(-c3c(OC)ncnc3C3CC3)nc21] | 0.96 | 581.5 | A |

TABLE 1-continued

| Example | Structure | RT | m/z [M + H]+ | HPLC Method |
|---|---|---|---|---|
| 2 | 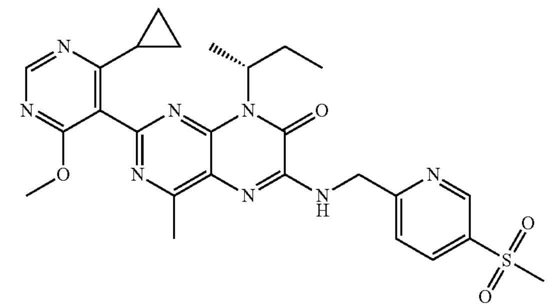 [SMILES: CC[C@@H](C)n1c(=O)c(NCc2ccc(S(C)(=O)=O)cn2)nc2c(C)nc(-c3c(OC)ncnc3C3CC3)nc21] | 0.99 | 551.4 | A |
| 3 | 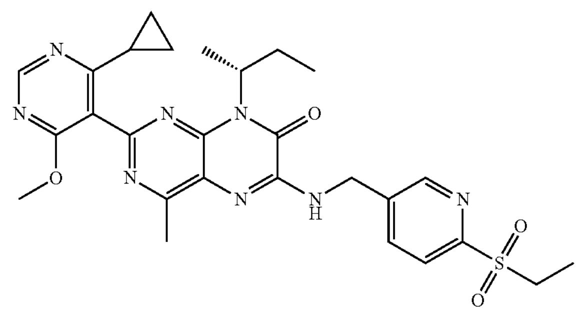 [SMILES: CC[C@@H](C)n1c(=O)c(NCc2ccc(S(=O)(=O)CC)nc2)nc2c(C)nc(-c3c(OC)ncnc3C3CC3)nc21] | 1.03 | 565.5 | A |
| 4 | 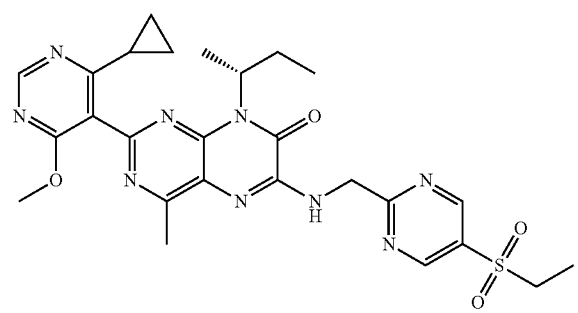 [SMILES: CC[C@@H](C)n1c(=O)c(NCc2ncc(S(=O)(=O)CC)cn2)nc2c(C)nc(-c3c(OC)ncnc3C3CC3)nc21] | 1.03 | 566.4 | A |
| 5 | 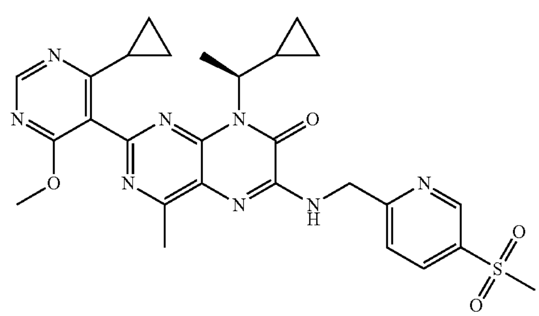 [SMILES: COc1ncnc(C2CC2)c1-c1nc(C)c2nc(NCc3ccc(S(C)(=O)=O)cn3)c(=O)n([C@@H](C)C3CC3)c2n1] | 1.01 | 563.4 | A |
| 6 | 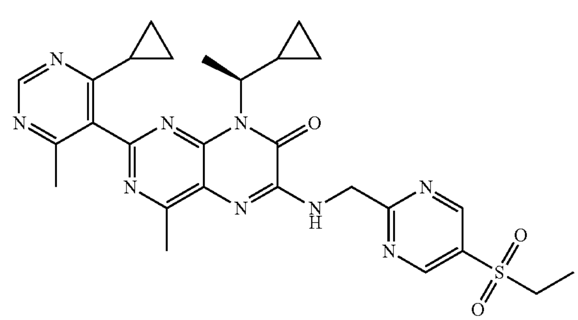 [SMILES: CCS(=O)(=O)c1cnc(CNc2nc3c(C)nc(-c4c(C)ncnc4C4CC4)nc3n([C@@H](C)C3CC3)c2=O)nc1] | 1.00 | 562.3 | A |

TABLE 1-continued

| Example | Structure | RT | m/z [M + H]+ | HPLC Method |
|---|---|---|---|---|
| 7 | 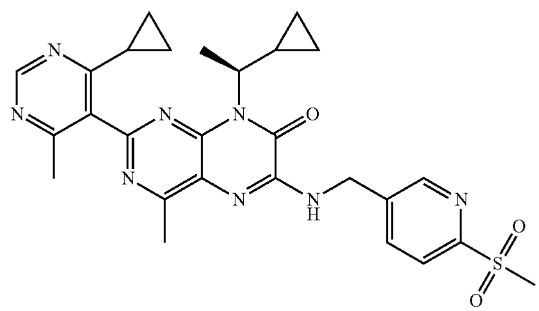 [SMILES: Cc1ncnc(C2CC2)c1-c1nc(C)c2nc(NCc3ccc(S(C)(=O)=O)nc3)c(=O)n([C@@H](C)C3CC3)c2n1] | 0.96 | 547.4 | A |
| 8 | 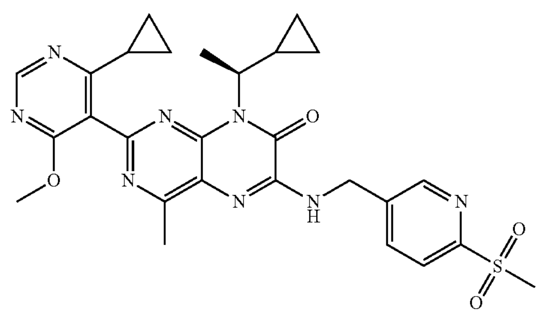 [SMILES: COc1ncnc(C2CC2)c1-c1nc(C)c2nc(NCc3ccc(S(C)(=O)=O)nc3)c(=O)n([C@@H](C)C3CC3)c2n1] | 1.01 | 563.5 | A |
| 9 | 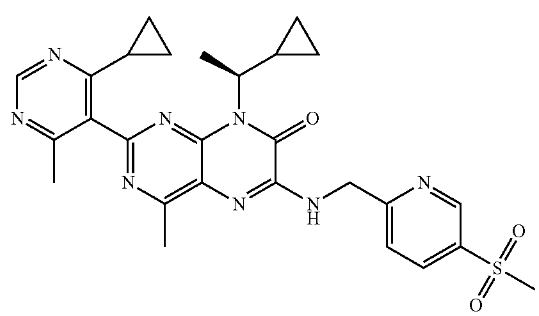 [SMILES: Cc1ncnc(C2CC2)c1-c1nc(C)c2nc(NCc3ccc(S(C)(=O)=O)cn3)c(=O)n([C@@H](C)C3CC3)c2n1] | 0.95 | 547.4 | A |
| 10 | 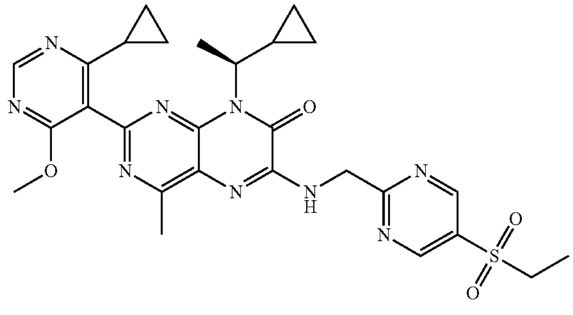 [SMILES: CCS(=O)(=O)c1cnc(CNc2nc3c(C)nc(-c4c(OC)ncnc4C4CC4)nc3n([C@@H](C)C3CC3)c2=O)nc1] | 1.05 | 578.4 | A |

TABLE 1-continued

| Example | Structure | RT | m/z [M + H]+ | HPLC Method |
|---|---|---|---|---|
| 11 | 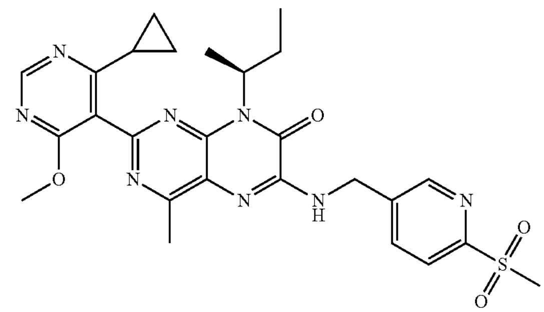 [SMILES: CC[C@H](C)n1c(=O)c(NCc2ccc(S(C)(=O)=O)nc2)nc2c(C)nc(-c3c(OC)ncnc3C3CC3)nc21] | 0.99 | 551.4 | A |
| 12 | 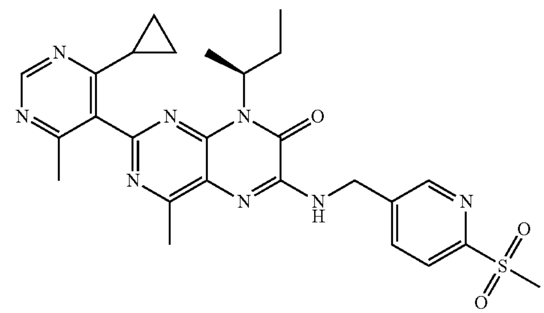 [SMILES: CC[C@H](C)n1c(=O)c(NCc2ccc(S(C)(=O)=O)nc2)nc2c(C)nc(-c3c(C)ncnc3C3CC3)nc21] | 0.94 | 535.5 | A |
| 13 | 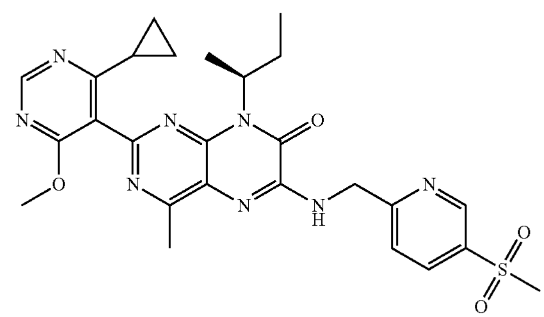 [SMILES: CC[C@H](C)n1c(=O)c(NCc2ccc(S(C)(=O)=O)cn2)nc2c(C)nc(-c3c(OC)ncnc3C3CC3)nc21] | 1.00 | 551.6 | A |
| 14 | 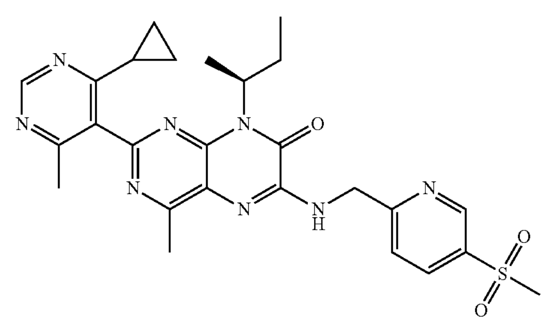 [SMILES: CC[C@H](C)n1c(=O)c(NCc2ccc(S(C)(=O)=O)cn2)nc2c(C)nc(-c3c(C)ncnc3C3CC3)nc21] | 0.95 | 535.7 | A |
| 15 | 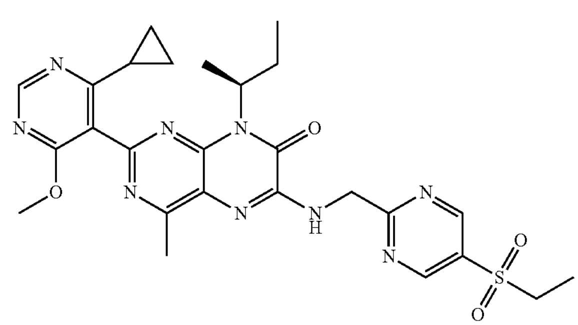 [SMILES: CC[C@H](C)n1c(=O)c(NCc2ncc(S(=O)(=O)CC)cn2)nc2c(C)nc(-c3c(OC)ncnc3C3CC3)nc21] | 1.04 | 566.7 | A |

TABLE 1-continued

| Example | Structure | RT | m/z [M + H]+ | HPLC Method |
|---------|-----------|-----|--------------|-------------|
| 16 | 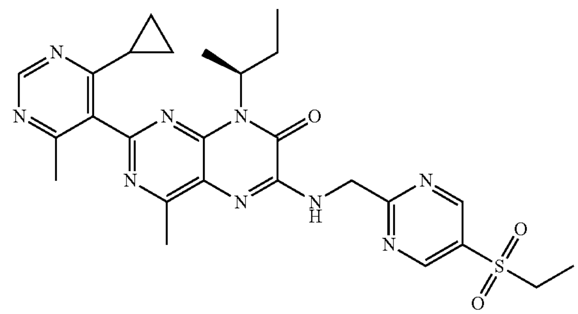 [SMILES: CC[C@H](C)n1c(=O)c(NCc2ncc(S(=O)(=O)CC)cn2)nc2c(C)nc(-c3c(C)ncnc3C3CC3)nc21] | 0.99 | 550.3 | A |
| 17 | 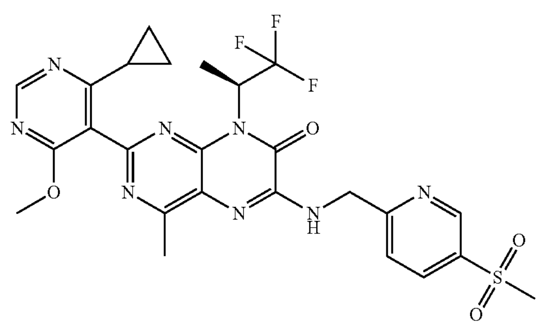 [SMILES: COc1ncnc(C2CC2)c1-c1nc(C)c2nc(NCc3ccc(S(C)(=O)=O)cn3)c(=O)n([C@@H](C)C(F)(F)F)c2n1] | 1.01 | 591.3 | A |
| 18 | 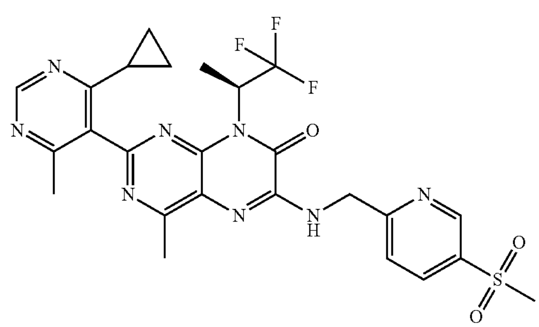 [SMILES: Cc1ncnc(C2CC2)c1-c1nc(C)c2nc(NCc3ccc(S(C)(=O)=O)cn3)c(=O)n([C@@H](C)C(F)(F)F)c2n1] | 0.94 | 575.4 | A |
| 19 | 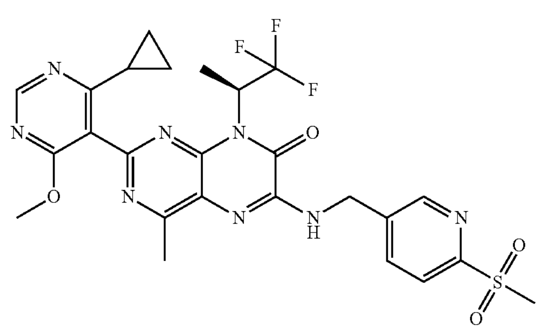 [SMILES: COc1ncnc(C2CC2)c1-c1nc(C)c2nc(NCc3ccc(S(C)(=O)=O)nc3)c(=O)n([C@@H](C)C(F)(F)F)c2n1] | 1.01 | 591.5 | A |

TABLE 1-continued

| Example | Structure | RT | m/z [M + H]+ | HPLC Method |
|---|---|---|---|---|
| 20 | 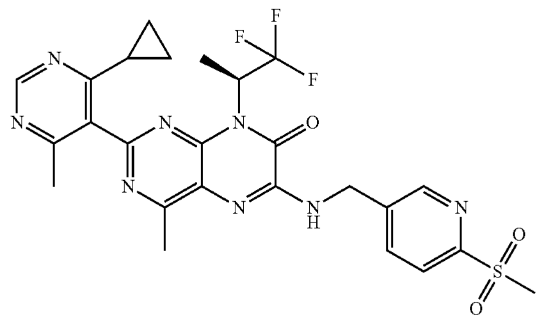 [SMILES: Cc1ncnc(C2CC2)c1-c1nc(C)c2nc(NCc3ccc(S(C)(=O)=O)nc3)c(=O)n([C@@H](C)C(F)(F)F)c2n1] | 0.96 | 575.4 | A |
| 21 | 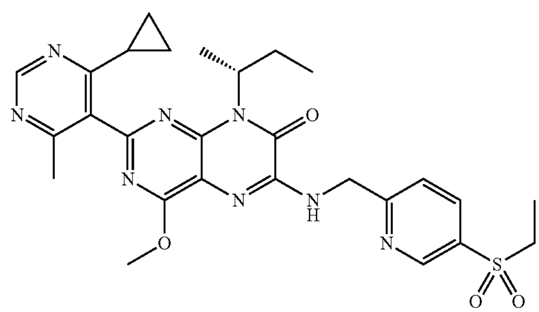 [SMILES: CC[C@@H](C)n1c(=O)c(NCc2ccc(S(=O)(=O)CC)cn2)nc2c(OC)nc(-c3c(C)ncnc3C3CC3)nc21] | 1.02 | 565.4 | A |
| 22 | 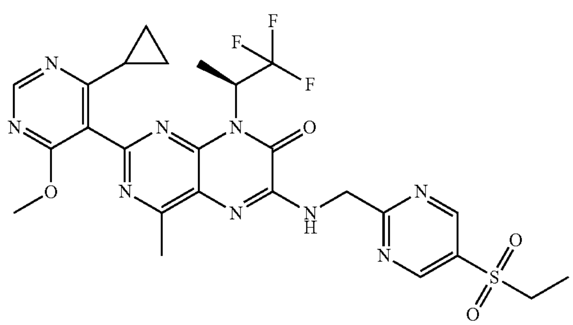 [SMILES: CCS(=O)(=O)c1cnc(CNc2nc3c(C)nc(-c4c(OC)ncnc4C4CC4)nc3n([C@@H](C)C(F)(F)F)c2=O)nc1] | 1.00 | 606.4 | A |
| 23 | 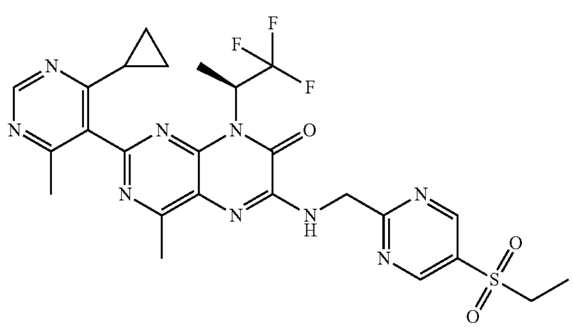 [SMILES: CCS(=O)(=O)c1cnc(CNc2nc3c(C)nc(-c4c(C)ncnc4C4CC4)nc3n([C@@H](C)C(F)(F)F)c2=O)nc1] | 0.95 | 590.4 | A |

TABLE 1-continued

| Example | Structure | RT | m/z [M + H]+ | HPLC Method |
|---------|-----------|------|-------|------|
| 24 | 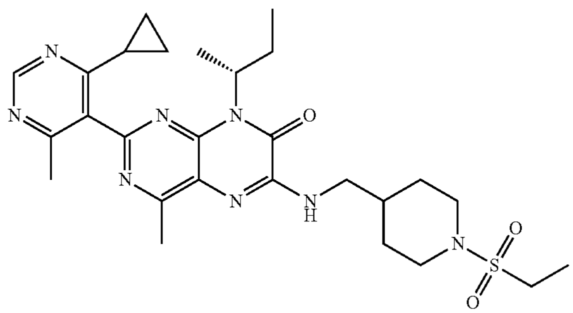 [SMILES: CC[C@@H](C)n1c(=O)c(NCC2CCN(S(=O)(=O)CC)CC2)nc2c(C)nc(-c3c(C)ncnc3C3CC3)nc21] | 1.20 | 555.3 | A |
| 25 | 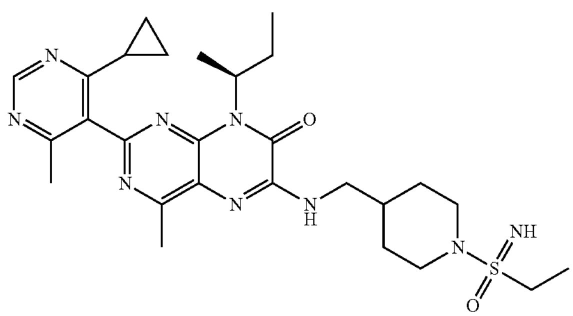 [SMILES: CC[C@H](C)n1c(=O)c(NCC2CCN(S(=N)(=O)CC)CC2)nc2c(C)nc(-c3c(C)ncnc3C3CC3)nc21] | 1.04 | 545.3 | A |
| 26a | 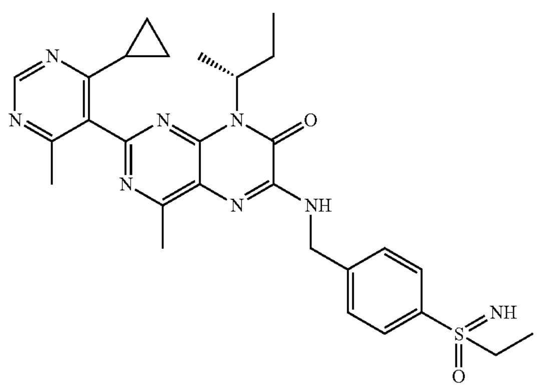 [SMILES: CC[C@@H](C)n1c(=O)c(NCc2ccc(S(=N)(=O)CC)cc2)nc2c(C)nc(-c3c(C)ncnc3C3CC3)nc21] | 1.04 | 547.3 | A |
| 26b | 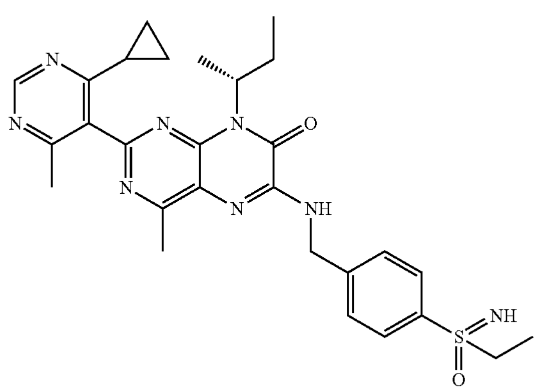 [SMILES: CC[C@@H](C)n1c(=O)c(NCc2ccc(S(=N)(=O)CC)cc2)nc2c(C)nc(-c3c(C)ncnc3C3CC3)nc21] | 1.04 | 547.2 | A |

TABLE 1-continued

| Example | Structure | RT | m/z [M + H]+ | HPLC Method |
|---|---|---|---|---|
| 27a | 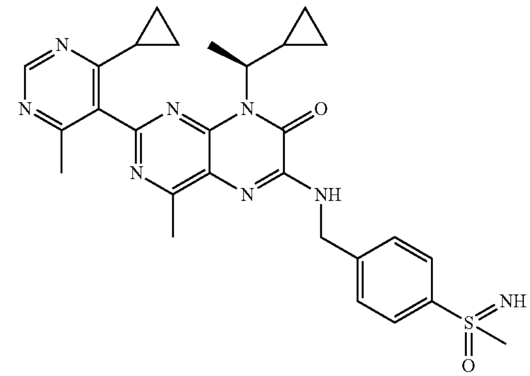 [SMILES: Cc1ncnc(C2CC2)c1-c1nc(C)c2nc(NCc3ccc(S(C)(=N)=O)cc3)c(=O)n([C@@H](C)C3CC3)c2n1] | 0.91 | 545.4 | A |
| 27b | 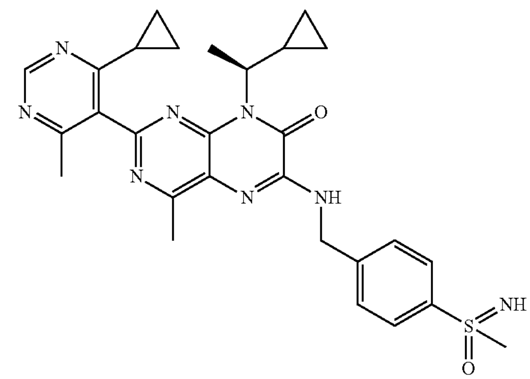 [SMILES: Cc1ncnc(C2CC2)c1-c1nc(C)c2nc(NCc3ccc(S(C)(=N)=O)cc3)c(=O)n([C@@H](C)C3CC3)c2n1] | 0.91 | 545.4 | A |
| 29a | 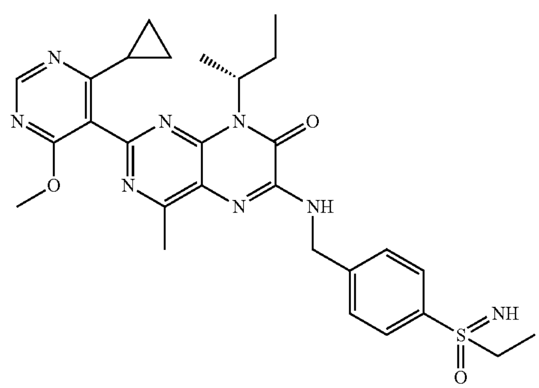 [SMILES: CC[C@@H](C)n1c(=O)c(NCc2ccc(S(=N)(=O)CC)cc2)nc2c(C)nc(-c3c(OC)ncnc3C3CC3)nc21] | 1.09 | 563.3 | A |
| 29b | 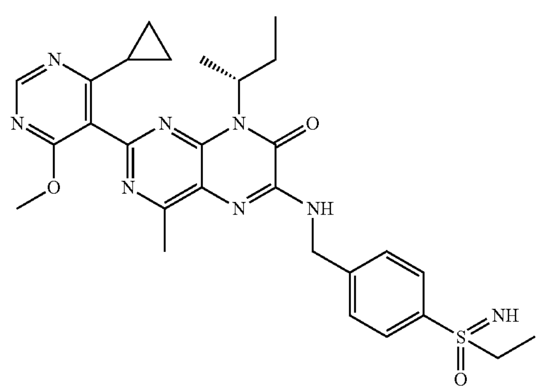 [SMILES: CC[C@@H](C)n1c(=O)c(NCc2ccc(S(=N)(=O)CC)cc2)nc2c(C)nc(-c3c(OC)ncnc3C3CC3)nc21] | 1.09 | 563.3 | A |

TABLE 1-continued

| Example | Structure | RT | m/z [M + H]+ | HPLC Method |
|---|---|---|---|---|
| 31 | 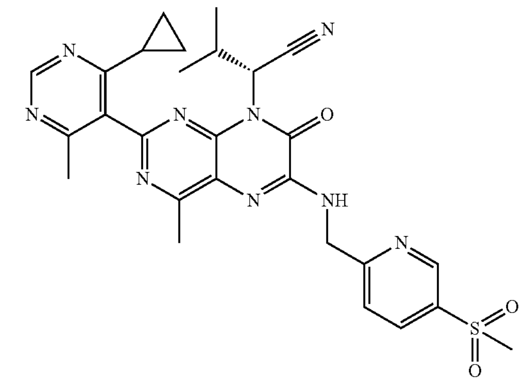 [SMILES: Cc1ncnc(C2CC2)c1-c1nc(C)c2nc(NCc3ccc(S(C)(=O)=O)cn3)c(=O)n([C@@H](C#N)C(C)C)c2n1] | 1.00 | 560.2 | A |
| 33 | 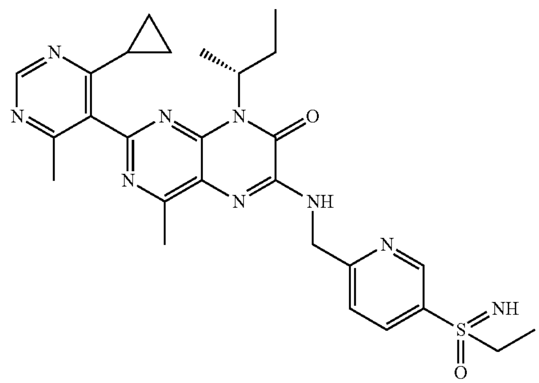 | 1.04 | 547.2 | A |
| 34a | 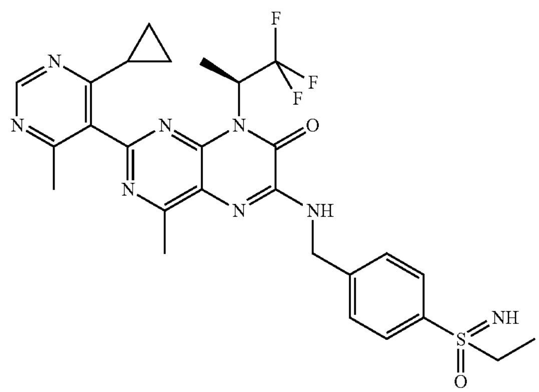 [SMILES: CCS(=N)(=O)c1ccc(CNc2nc3c(C)nc(-c4c(C)ncnc4C4CC4)nc3n([C@@H](C)C(F)(F)F)c2=O)cc1] | 0.90 | 587.2 | A |
| 34b | 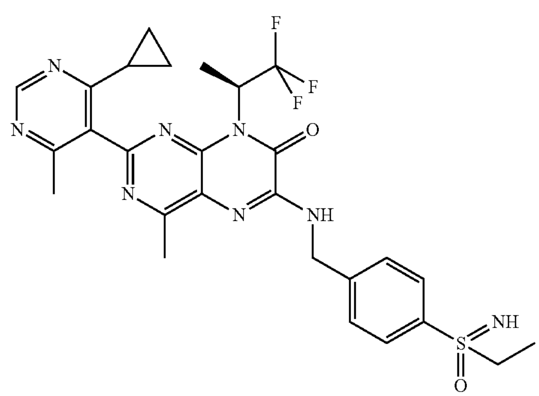 [SMILES: CCS(=N)(=O)c1ccc(CNc2nc3c(C)nc(-c4c(C)ncnc4C4CC4)nc3n([C@@H](C)C(F)(F)F)c2=O)cc1] | 0.90 | 587.2 | A |

TABLE 1-continued

| Example | Structure | RT | m/z [M + H]+ | HPLC Method |
|---|---|---|---|---|
| 36a | 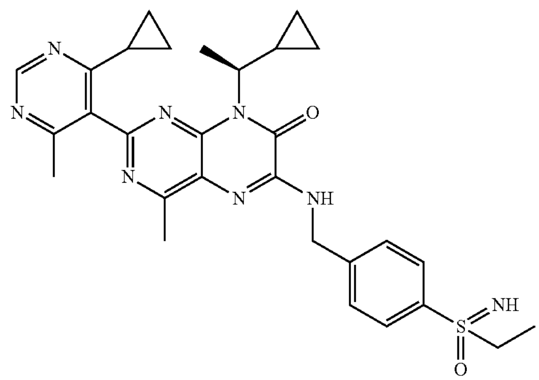 [SMILES: CCS(=N)(=O)c1ccc(CNc2nc3c(C)nc(-c4c(C)ncnc4C4CC4)nc3n([C@@H](C)C3CC3)c2=O)cc1] | 0.95 | 559.4 | A |
| 36b | 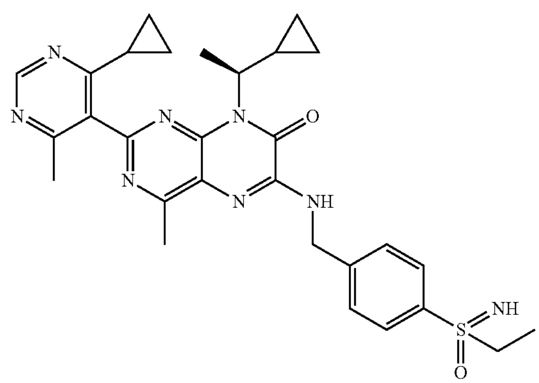 [SMILES: CCS(=N)(=O)c1ccc(CNc2nc3c(C)nc(-c4c(C)ncnc4C4CC4)nc3n([C@@H](C)C3CC3)c2=O)cc1] | 0.95 | 559.4 | A |
| 37 | 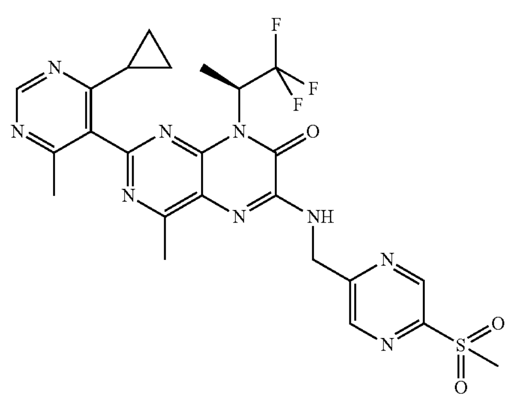 [SMILES: Cc1ncnc(C2CC2)c1-c1nc(C)c2nc(NCc3cnc(S(C)(=O)=O)cn3)c(=O)n([C@@H](C)C(F)(F)F)c2n1] | 1.07 | 576.2 | A |
| 38a | 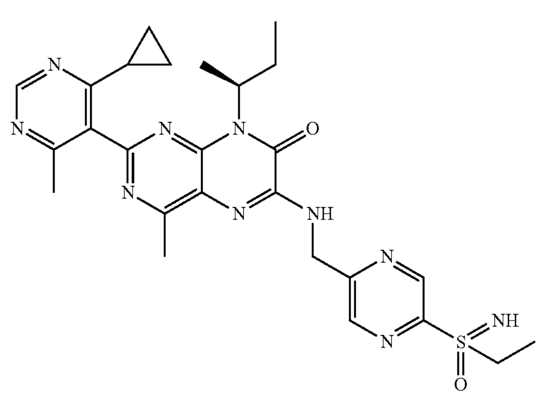 [SMILES: CC[C@H](C)n1c(=O)c(NCc2cnc(S(=N)(=O)CC)cn2)nc2c(C)nc(-c3c(C)ncnc3C3CC3)nc21] | 0.95 | 547.3 | A |

TABLE 1-continued

| Example | Structure | RT | m/z [M + H]⁺ | HPLC Method |
|---------|-----------|------|------|------|
| 38b | 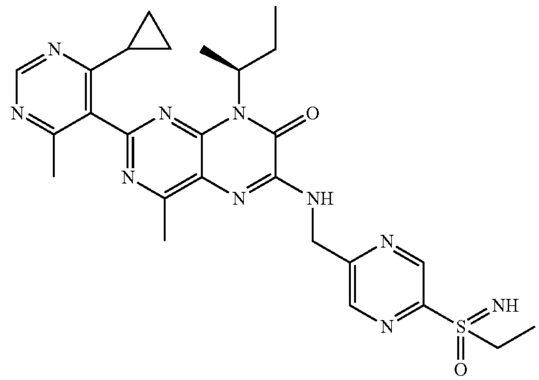 [SMILES: CC[C@H](C)n1c(=O)c(NCc2cnc(S(=N)(=O)CC)cn2)nc2c(C)nc(-c3c(C)ncnc3C3CC3)nc21] | 0.93 | 547.3 | A |
| 41 | 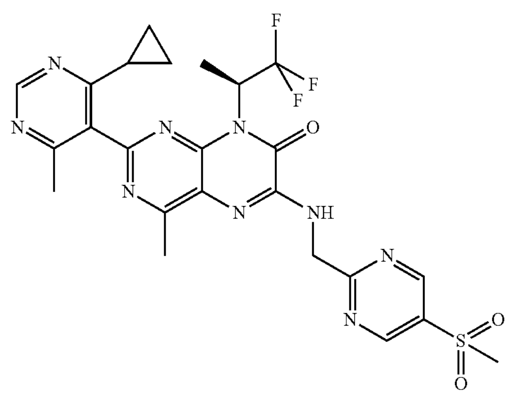 [SMILES: Cc1ncnc(C2CC2)c1-c1nc(C)c2nc(NCc3ncc(S(C)(=O)=O)cn3)c(=O)n([C@@H](C)C(F)(F)F)c2n1] | 1.07 | 574.2 | A |
| 42a | 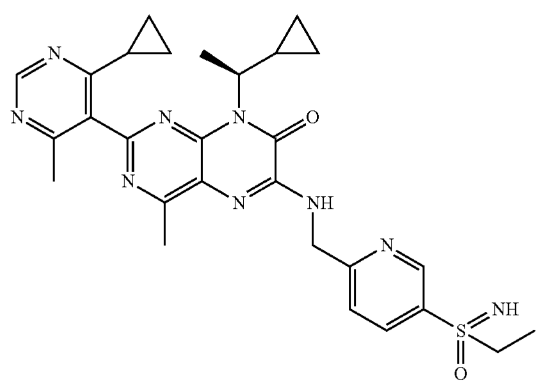 [SMILES: CCS(=N)(=O)c1ccc(CNc2nc3c(C)nc(-c4c(C)ncnc4C4CC4)nc3n([C@@H](C)C3CC3)c2=O)nc1] | 0.87 | 560.4 | A |
| 42b | 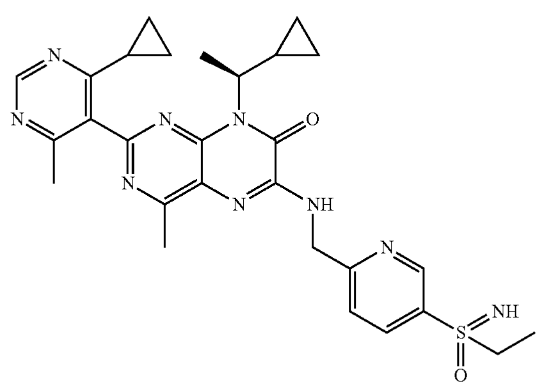 [SMILES: CCS(=N)(=O)c1ccc(CNc2nc3c(C)nc(-c4c(C)ncnc4C4CC4)nc3n([C@@H](C)C3CC3)c2=O)nc1] | 0.87 | 560.4 | A |

TABLE 1-continued

| Example | Structure | RT | m/z [M + H]+ | HPLC Method |
|---|---|---|---|---|
| 43a | 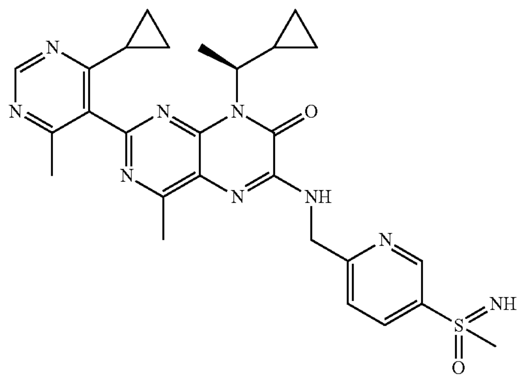 [SMILES: Cc1ncnc(C2CC2)c1-c1nc(C)c2nc(NCc3ccc(S(C)(=N)=O)cn3)c(=O)n([C@@H](C)C3CC3)c2n1] | 0.82 | 546.4 | A |
| 43b | 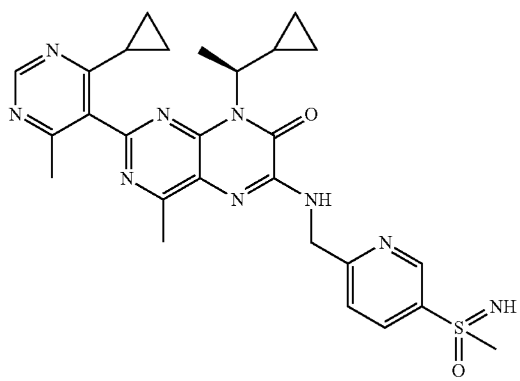 [SMILES: Cc1ncnc(C2CC2)c1-c1nc(C)c2nc(NCc3ccc(S(C)(=N)=O)cn3)c(=O)n([C@@H](C)C3CC3)c2n1] | 0.83 | 546.4 | A |
| 46 | 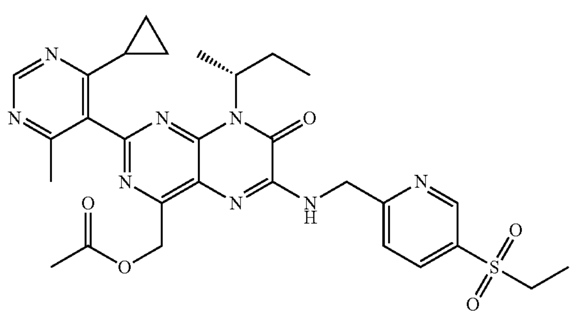 [SMILES: CC[C@@H](C)n1c(=O)c(NCc2ccc(S(=O)(=O)CC)cn2)nc2c(COC(C)=O)nc(-c3c(C)ncnc3C3CC3)nc21] | 1.03 | 607.7 | A |
| 47 | 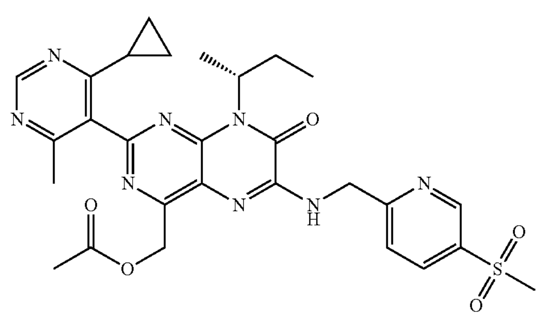 [SMILES: CC[C@@H](C)n1c(=O)c(NCc2ccc(S(C)(=O)=O)cn2)nc2c(COC(C)=O)nc(-c3c(C)ncnc3C3CC3)nc21] | 0.99 | 593.1 | A |

TABLE 1-continued

| Example | Structure | RT | m/z [M + H]+ | HPLC Method |
|---|---|---|---|---|
| 48 | 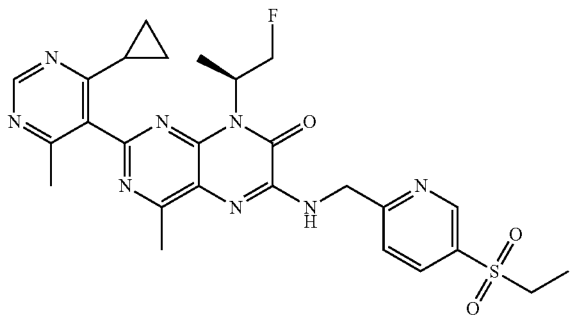 [SMILES: CCS(=O)(=O)c1ccc(CNc2nc3c(C)nc(-c4c(C)ncnc4C4CC4)nc3n([C@@H](C)CF)c2=O)nc1] | 0.86 | 553.1 | A |
| 49 | 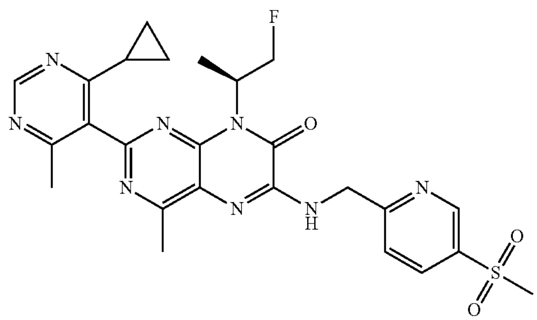 [SMILES: Cc1ncnc(C2CC2)c1-c1nc(C)c2nc(NCc3ccc(S(C)(=O)=O)cn3)c(=O)n([C@@H](C)CF)c2n1] | 0.81 | 539.1 | A |
| 50 | 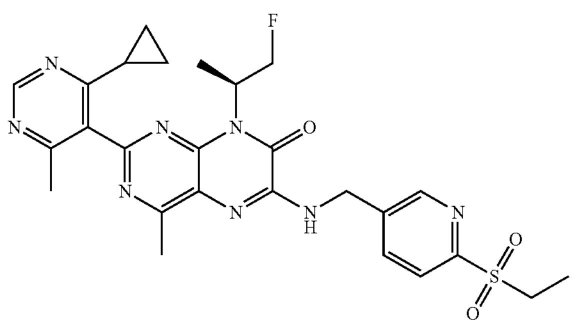 [SMILES: CCS(=O)(=O)c1ccc(CNc2nc3c(C)nc(-c4c(C)ncnc4C4CC4)nc3n([C@@H](C)CF)c2=O)cn1] | 0.86 | 553.1 | A |
| 51 | 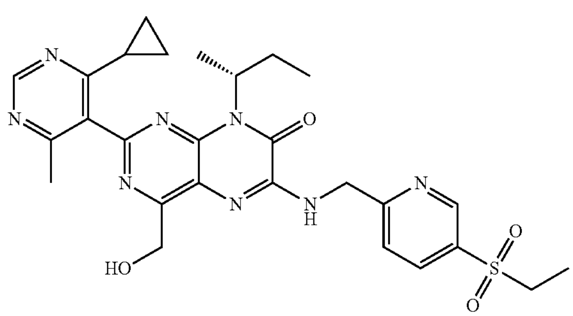 [SMILES: CC[C@@H](C)n1c(=O)c(NCc2ccc(S(=O)(=O)CC)cn2)nc2c(CO)nc(-c3c(C)ncnc3C3CC3)nc21] | 0.87 | 565.2 | A |
| 52 | 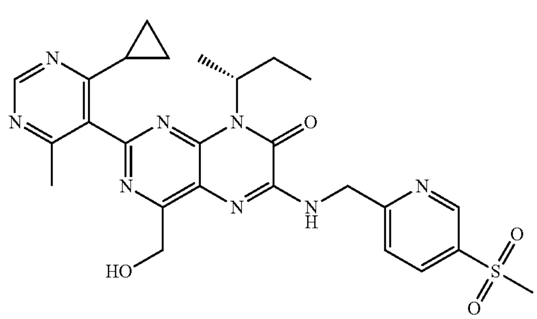 [SMILES: CC[C@@H](C)n1c(=O)c(NCc2ccc(S(C)(=O)=O)cn2)nc2c(CO)nc(-c3c(C)ncnc3C3CC3)nc21] | 0.83 | 551.2 | A |

TABLE 1-continued

| Example | Structure | RT | m/z [M + H]+ | HPLC Method |
|---|---|---|---|---|
| 53 | 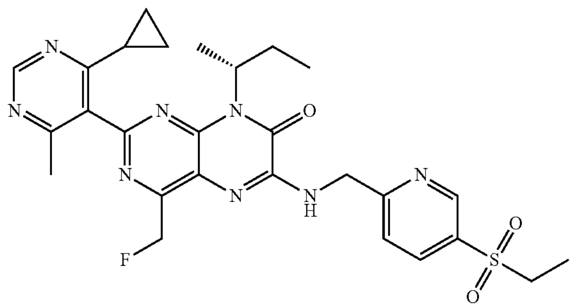 [SMILES: CC[C@@H](C)n1c(=O)c(NCc2ccc(S(=O)(=O)CC)cn2)nc2c(CF)nc(-c3c(C)ncnc3C3CC3)nc21] | 0.96 | 567.2 | A |
| 54 | 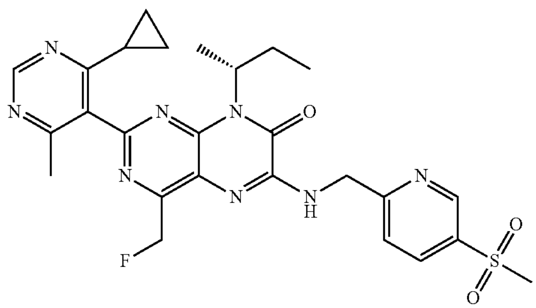 [SMILES: CC[C@@H](C)n1c(=O)c(NCc2ccc(S(C)(=O)=O)cn2)nc2c(CF)nc(-c3c(C)ncnc3C3CC3)nc21] | 0.91 | 553.2 | A |
| 55 | 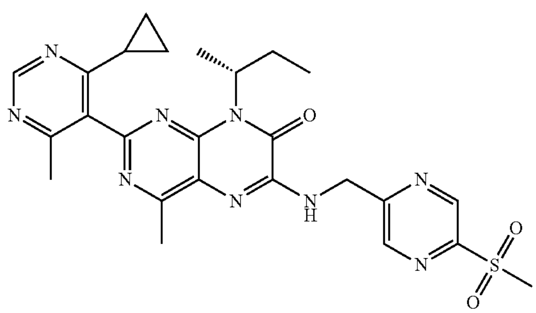 [SMILES: CC[C@@H](C)n1c(=O)c(NCc2cnc(S(C)(=O)=O)cn2)nc2c(C)nc(-c3c(C)ncnc3C3CC3)nc21] | 0.96 | 536.0 | A |
| 56 | 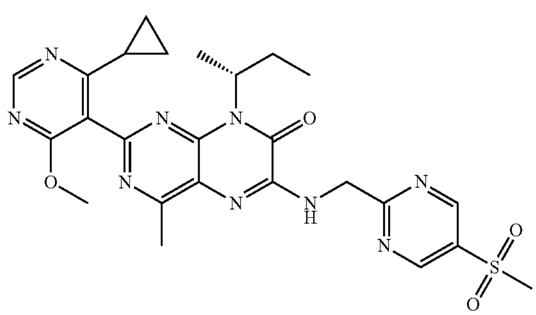 [SMILES: CC[C@@H](C)n1c(=O)c(NCc2ncc(S(C)(=O)=O)cn2)nc2c(C)nc(-c3c(OC)ncnc3C3CC3)nc21] | 1.02 | 552.0 | A |
| 57 | 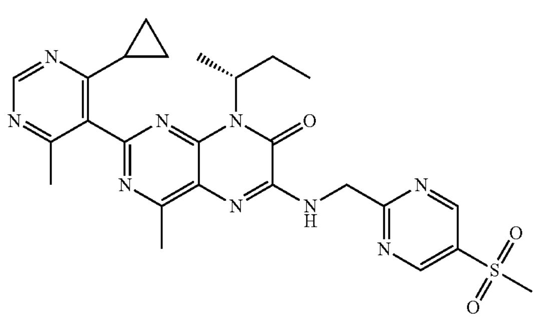 [SMILES: CC[C@@H](C)n1c(=O)c(NCc2ncc(S(C)(=O)=O)cn2)nc2c(C)nc(-c3c(C)ncnc3C3CC3)nc21] | 0.96 | 534.2 | A |

TABLE 1-continued

| Example | Structure | RT | m/z [M + H]+ | HPLC Method |
|---------|-----------|-----|--------------|-------------|
| 58 | 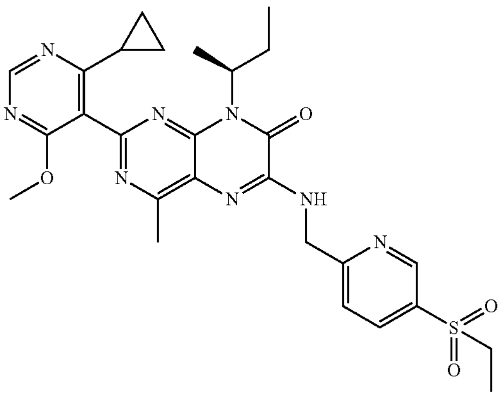 [SMILES: CC[C@H](C)n1c(=O)c(NCc2ccc(S(=O)(=O)CC)cn2)nc2c(C)nc(-c3c(OC)ncnc3C3CC3)nc21] | 1.08 | 564.9 | A |
| 59 | 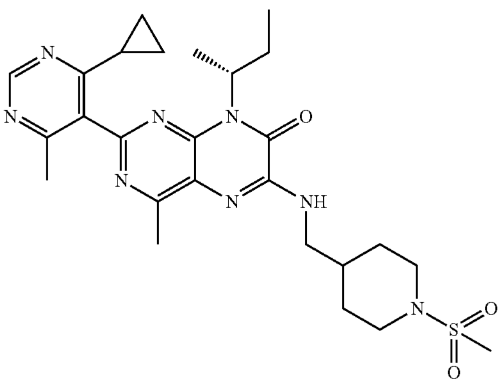 [SMILES: CC[C@@H](C)n1c(=O)c(NCC2CCN(S(C)(=O)=O)CC2)nc2c(C)nc(-c3c(C)ncnc3C3CC3)nc21] | 1.15 | 541.3 | A |
| 60 | 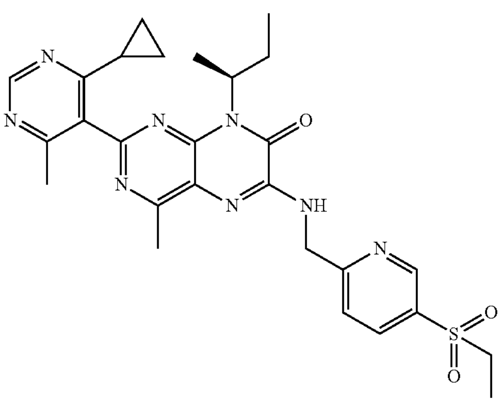 [SMILES: CC[C@H](C)n1c(=O)c(NCc2ccc(S(=O)(=O)CC)cn2)nc2c(C)nc(-c3c(C)ncnc3C3CC3)nc21] | 1.03 | 549.0 | A |
| 61 | 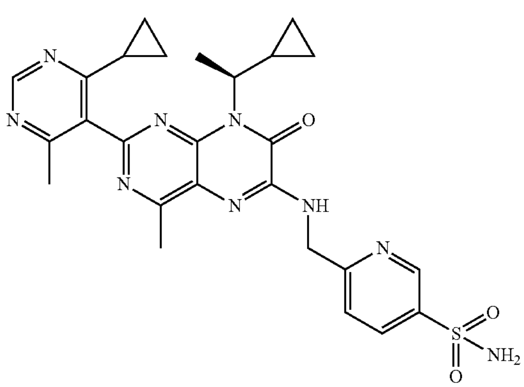 [SMILES: Cc1ncnc(C2CC2)c1-c1nc(C)c2nc(NCc3ccc(S(N)(=O)=O)cn3)c(=O)n([C@@H](C)C3CC3)c2n1] | 0.88 | 548.2 | A |

TABLE 1-continued
| Example | Structure | RT | m/z [M + H]+ | HPLC Method |
|---|---|---|---|---|
| 62 | 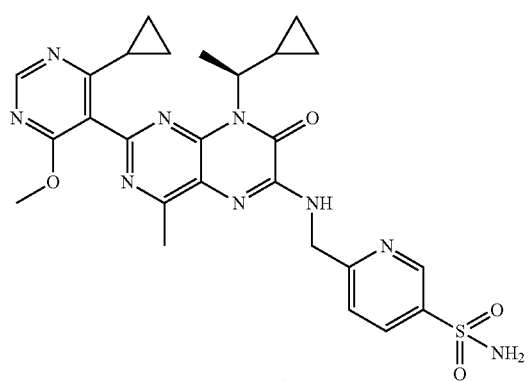 [SMILES: COc1ncnc(C2CC2)c1-c1nc(C)c2nc(NCc3ccc(S(N)(=O)=O)cn3)c(=O)n([C@@H](C)C3CC3)c2n1] | 0.94 | 565.2 | A |
| 63 | 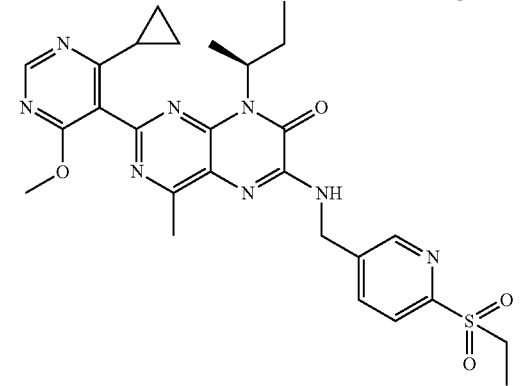 [SMILES: CC[C@H](C)n1c(=O)c(NCc2ccc(S(=O)(=O)CC)nc2)nc2c(C)nc(-c3c(OC)ncnc3C3CC3)nc21] | 1.07 | 563.2 | A |
| 64 | 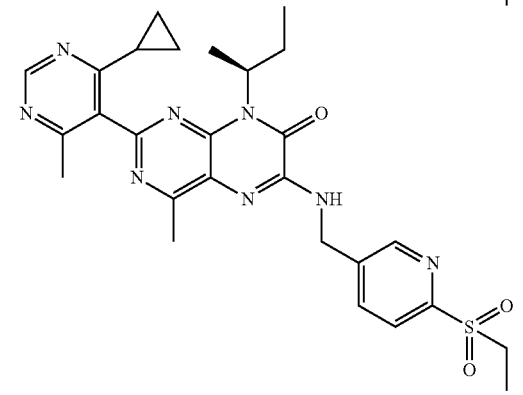 | 1.02 | 550.5 | A |
| 65 | 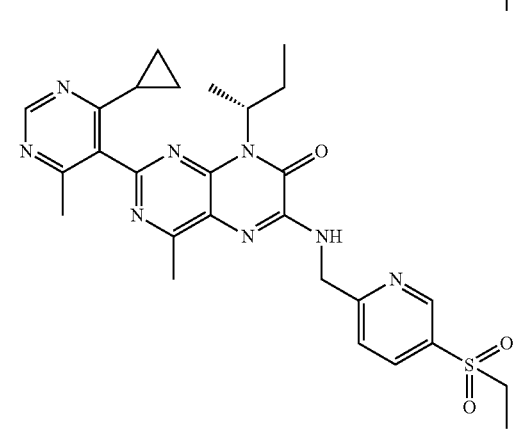 | 1.01 | 549.3 | A |

TABLE 1-continued

| Example | Structure | RT | m/z [M + H]+ | HPLC Method |
|---|---|---|---|---|
| 66 | 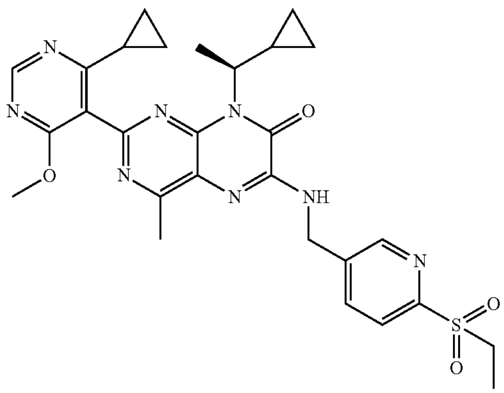 [SMILES: CCS(=O)(=O)c1ccc(CNc2nc3c(C)nc(-c4c(OC)ncnc4C4CC4)nc3n([C@@H](C)C3CC3)c2=O)cn1] | 1.09 | 577.0 | A |
| 67 | 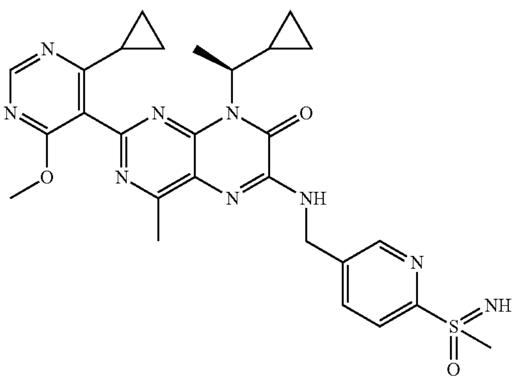 [SMILES: COc1ncnc(C2CC2)c1-c1nc(C)c2nc(NCc3ccc(S(C)(=N)=O)nc3)c(=O)n([C@@H](C)C3CC3)c2n1] | 0.95 | 561.3 | A |
| 68 | 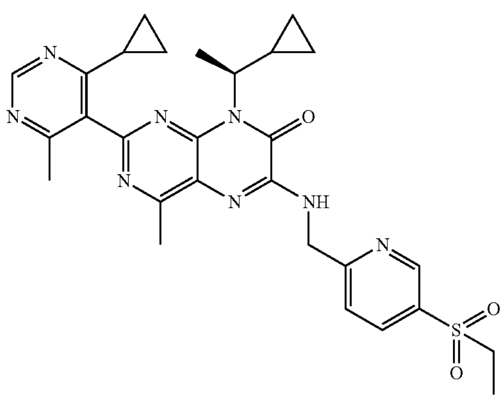 [SMILES: CCS(=O)(=O)c1ccc(CNc2nc3c(C)nc(-c4c(C)ncnc4C4CC4)nc3n([C@@H](C)C3CC3)c2=O)nc1] | 1.04 | 562.2 | A |
| 69 | 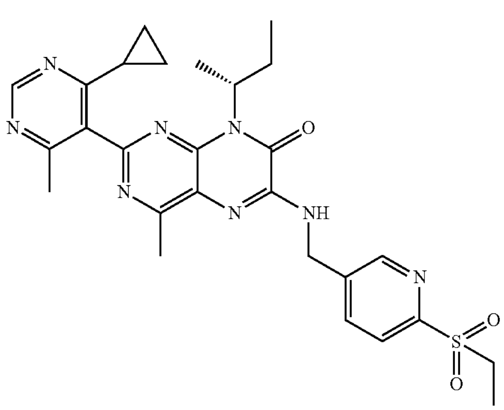 [SMILES: CC[C@@H](C)n1c(=O)c(NCc2ccc(S(=O)(=O)CC)nc2)nc2c(C)nc(-c3c(C)ncnc3C3CC3)nc21] | 1.02 | 547.3 | A |

TABLE 1-continued

| Example | Structure | RT | m/z [M + H]+ | HPLC Method |
|---------|-----------|-----|--------------|-------------|
| 70 | 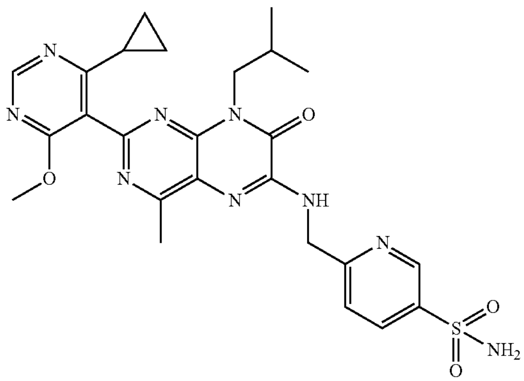 [SMILES: COc1ncnc(C2CC2)c1-c1nc(C)c2nc(NCc3ccc(S(N)(=O)=O)cn3)c(=O)n(CC(C)C)c2n1] | 0.92 | 552.5 | A |
| 71 | 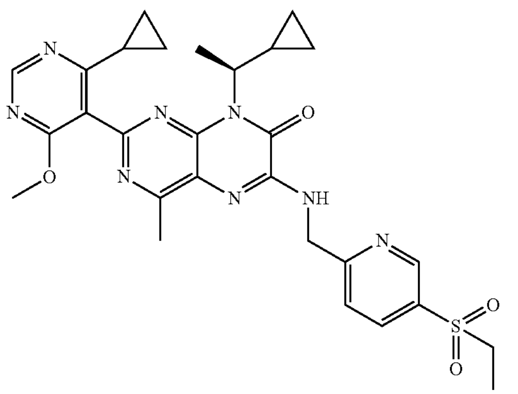 [SMILES: CCS(=O)(=O)c1ccc(CNc2nc3c(C)nc(-c4c(OC)ncnc4C4CC4)nc3n([C@@H](C)C3CC3)c2=O)nc1] | 1.09 | 578.4 | A |
| 72 | 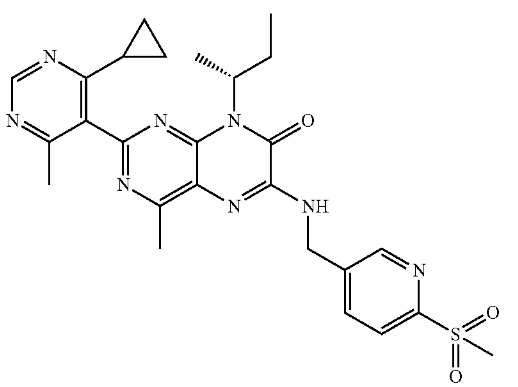 [SMILES: CC[C@@H](C)n1c(=O)c(NCc2ccc(S(C)(=O)=O)nc2)nc2c(C)nc(-c3c(C)ncnc3C3CC3)nc21] | 0.98 | 533.2 | A |
| 73 | 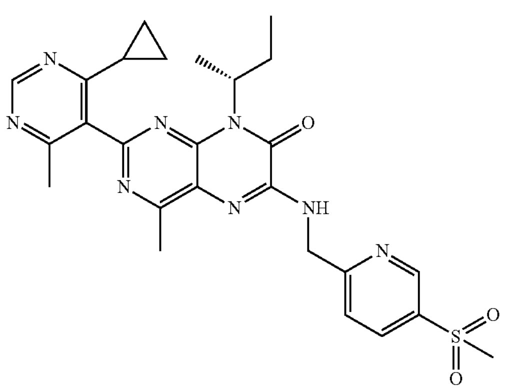 [SMILES: CC[C@@H](C)n1c(=O)c(NCc2ccc(S(C)(=O)=O)cn2)nc2c(C)nc(-c3c(C)ncnc3C3CC3)nc21] | 0.98 | 535.3 | A |

TABLE 1-continued
| Example | Structure | RT | m/z [M + H]+ | HPLC Method |
|---|---|---|---|---|
| 74 | 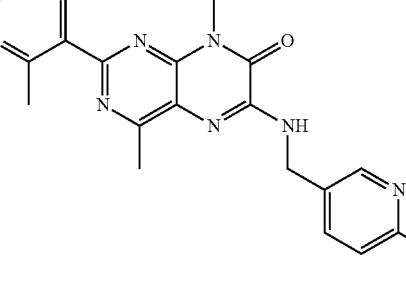 | 1.04 | 562.2 | A |
| 75 | 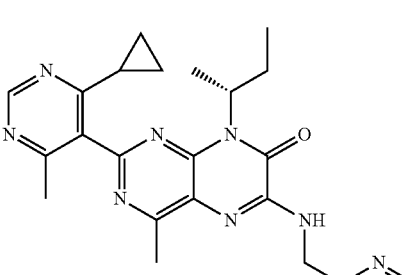 | 1.02 | 549.2 | A |
| 76 | 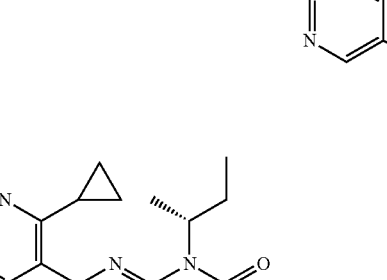 | 0.87 | 536.1 | A |
| 77 | 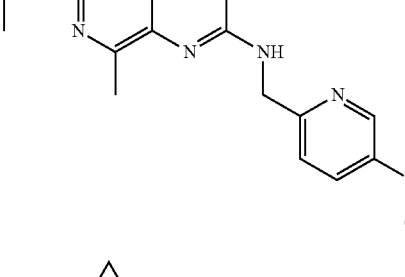 | 1.01 | 551.3 | A |

TABLE 1-continued

| Example | Structure | RT | m/z [M + H]+ | HPLC Method |
|---|---|---|---|---|
| 78 | 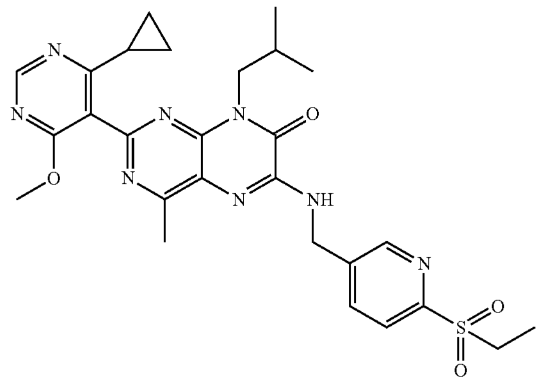 [SMILES: CCS(=O)(=O)c1ccc(CNc2nc3c(C)nc(-c4c(OC)ncnc4C4CC4)nc3n(CC(C)C)c2=O)cn1] | 1.01 | 565.1 | A |
| 79 | 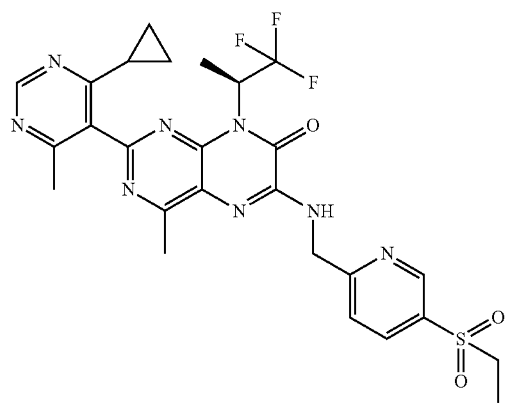 [SMILES: CCS(=O)(=O)c1ccc(CNc2nc3c(C)nc(-c4c(C)ncnc4C4CC4)nc3n([C@@H](C)C(F)(F)F)c2=O)nc1] | 1.01 | 589.2 | A |
| 80 | 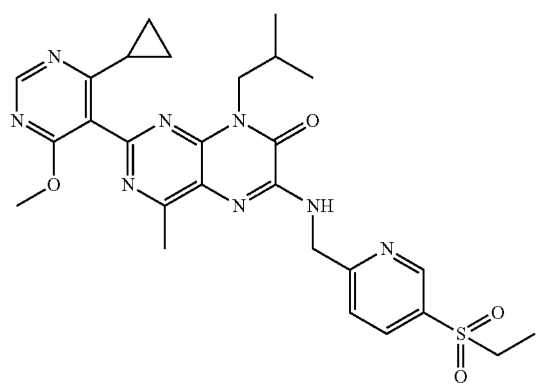 [SMILES: CCS(=O)(=O)c1ccc(CNc2nc3c(C)nc(-c4c(OC)ncnc4C4CC4)nc3n(CC(C)C)c2=O)nc1] | 1.06 | 565.3 | A |
| 81 | 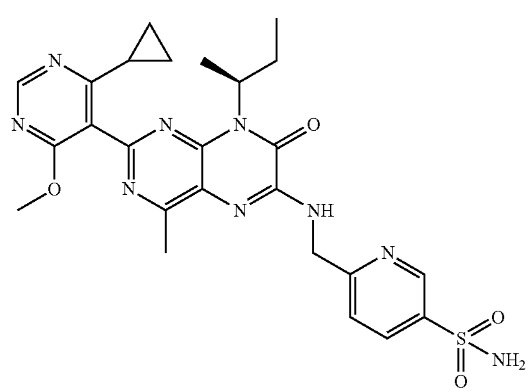 [SMILES: CC[C@H](C)n1c(=O)c(NCc2ccc(S(N)(=O)=O)cn2)nc2c(C)nc(-c3c(OC)ncnc3C3CC3)nc21] | 0.93 | 552.2 | A |

TABLE 1-continued

| Example | Structure | RT | m/z [M + H]+ | HPLC Method |
|---|---|---|---|---|
| 82 | 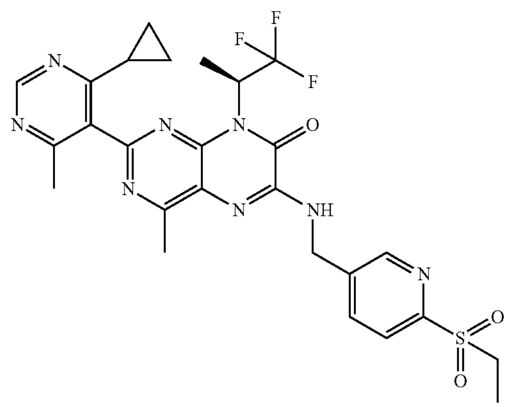 [SMILES: CCS(=O)(=O)c1ccc(CNc2nc3c(C)nc(-c4c(C)ncnc4C4CC4)nc3n([C@@H](C)C(F)(F)F)c2=O)cn1] | 1.01 | 589.1 | A |
| 83 | 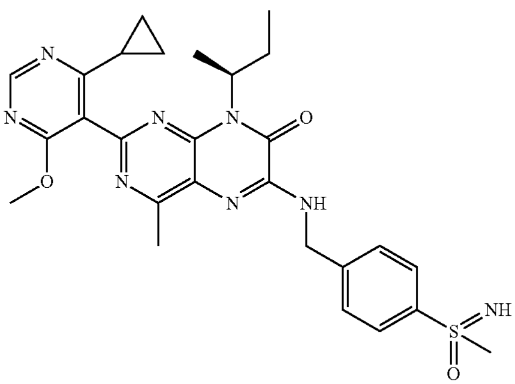 [SMILES: CC[C@H](C)n1c(=O)c(NCc2ccc(S(C)(=N)=O)cc2)nc2c(C)nc(-c3c(OC)ncnc3C3CC3)nc21] | 0.94 | 549.2 | A |
| 84 | 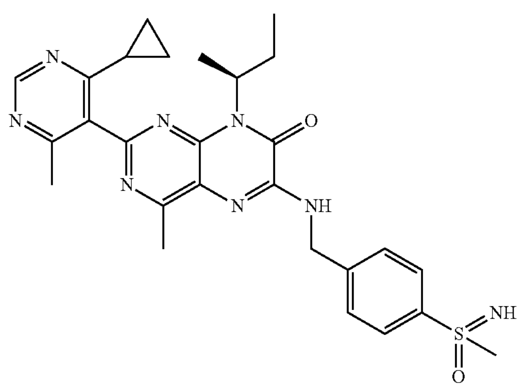 [SMILES: CC[C@H](C)n1c(=O)c(NCc2ccc(S(C)(=N)=O)cc2)nc2c(C)nc(-c3c(C)ncnc3C3CC3)nc21] | 0.87 | 533.2 | A |
| 85 | 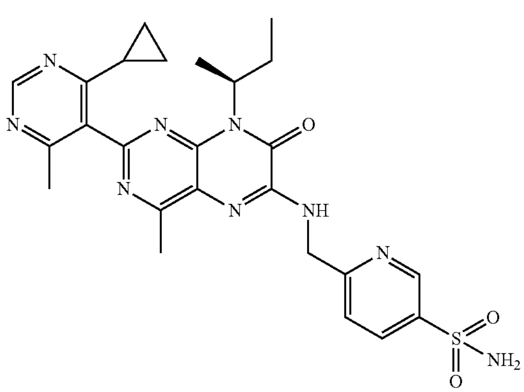 [SMILES: CC[C@H](C)n1c(=O)c(NCc2ccc(S(N)(=O)=O)cn2)nc2c(C)nc(-c3c(C)ncnc3C3CC3)nc21] | 0.91 | 536.2 | A |

TABLE 1-continued

| Example | Structure | RT | m/z [M + H]+ | HPLC Method |
|---|---|---|---|---|
| 86 | 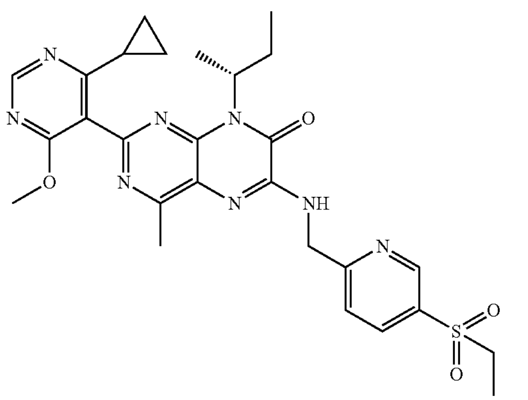 [SMILES: CC[C@@H](C)n1c(=O)c(NCc2ccc(S(=O)(=O)CC)cn2)nc2c(C)nc(-c3c(OC)ncnc3C3CC3)nc21] | 1.12 | 566.3 | A |
| 87 | 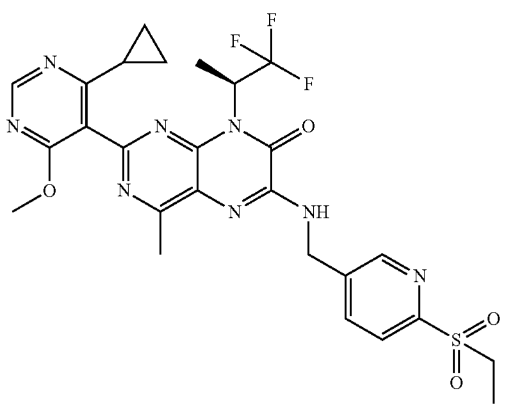 [SMILES: CCS(=O)(=O)c1ccc(CNc2nc3c(C)nc(-c4c(OC)ncnc4C4CC4)nc3n([C@@H](C)C(F)(F)F)c2=O)cn1] | 1.03 | 603.2 | A |
| 88 | 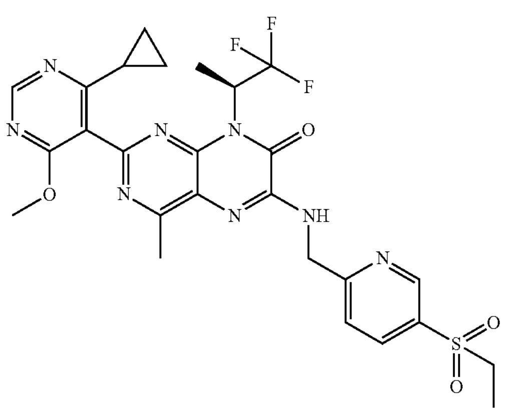 [SMILES: CCS(=O)(=O)c1ccc(CNc2nc3c(C)nc(-c4c(OC)ncnc4C4CC4)nc3n([C@@H](C)C(F)(F)F)c2=O)nc1] | 1.03 | 605.1 | A |
| 89 | 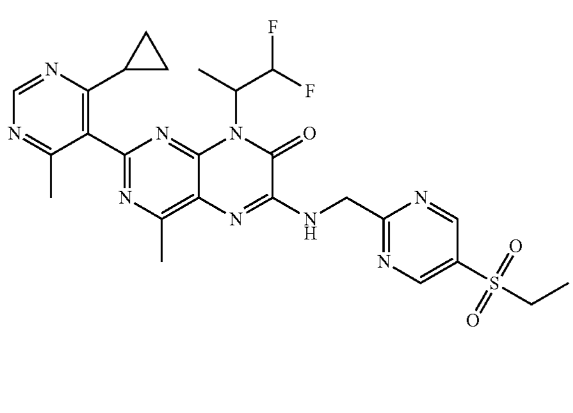 [SMILES: CCS(=O)(=O)c1cnc(CNc2nc3c(C)nc(-c4c(C)ncnc4C4CC4)nc3n(C(C)C(F)F)c2=O)nc1] | 0.93 | 572.1 | A |

TABLE 1-continued

| Example | Structure | RT | m/z [M + H]+ | HPLC Method |
|---|---|---|---|---|
| 90 | 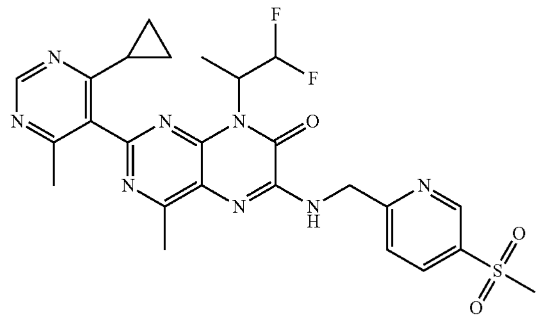 [SMILES: Cc1ncnc(C2CC2)c1-c1nc(C)c2nc(NCc3ccc(S(C)(=O)=O)cn3)c(=O)n(C(C)C(F)F)c2n1] | 0.89 | 557.3 | A |
| 91a | 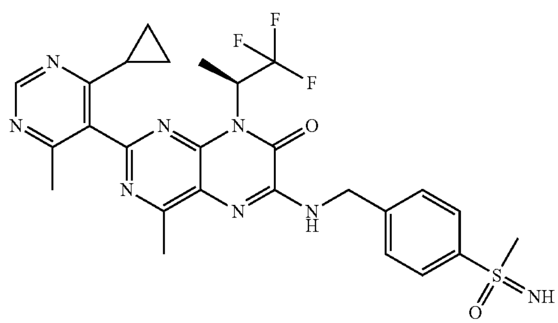 [SMILES: Cc1ncnc(C2CC2)c1-c1nc(C)c2nc(NCc3ccc(S(C)(=N)=O)cc3)c(=O)n([C@@H](C)C(F)(F)F)c2n1] | 0.91 | 573.2 | A |
| 91b | 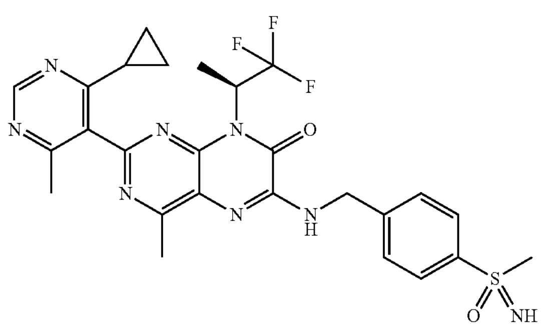 [SMILES: Cc1ncnc(C2CC2)c1-c1nc(C)c2nc(NCc3ccc(S(C)(=N)=O)cc3)c(=O)n([C@@H](C)C(F)(F)F)c2n1] | 0.91 | 573.2 | A |
| 93 | 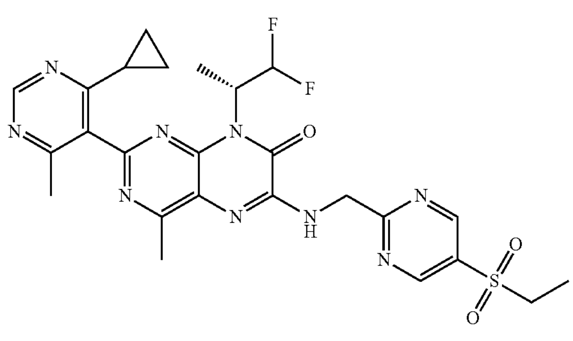 [SMILES: CCS(=O)(=O)c1cnc(CNc2nc3c(C)nc(-c4c(C)ncnc4C4CC4)nc3n([C@H](C)C(F)F)c2=O)nc1] | 0.94 | 572.2 | A |

TABLE 1-continued

| Example | Structure | RT | m/z [M + H]+ | HPLC Method |
|---|---|---|---|---|
| 94 | 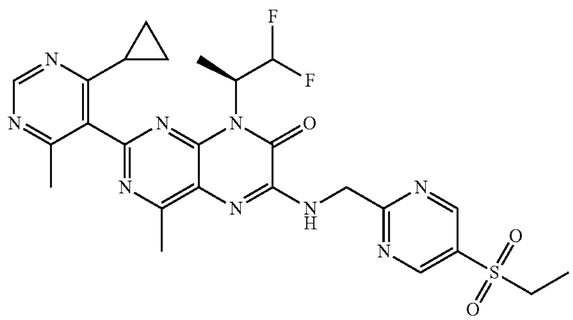 [SMILES: CCS(=O)(=O)c1cnc(CNc2nc3c(C)nc(-c4c(C)ncnc4C4CC4)nc3n([C@@H](C)C(F)F)c2=O)nc1] | 0.94 | 572.3 | A |
| 95 | 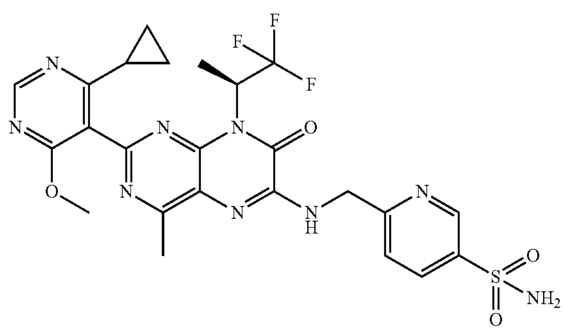 [SMILES: COc1ncnc(C2CC2)c1-c1nc(C)c2nc(NCc3ccc(S(N)(=O)=O)cn3)c(=O)n([C@@H](C)C(F)(F)F)c2n1] | 0.92 | 592.3 | A |
| 96 | 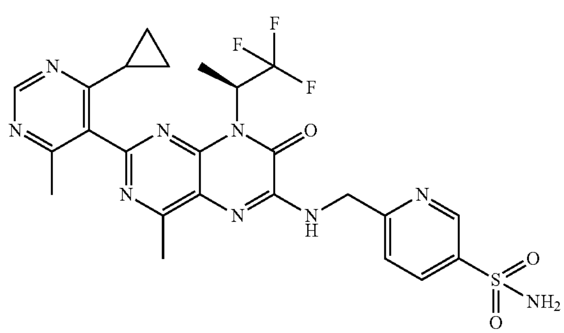 [SMILES: Cc1ncnc(C2CC2)c1-c1nc(C)c2nc(NCc3ccc(S(N)(=O)=O)cn3)c(=O)n([C@@H](C)C(F)(F)F)c2n1] | 0.86 | 576.3 | A |
| 97 | 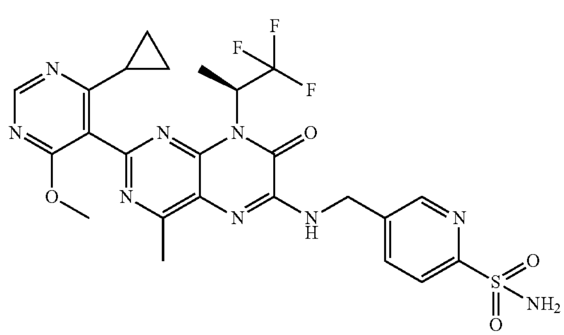 [SMILES: COc1ncnc(C2CC2)c1-c1nc(C)c2nc(NCc3ccc(S(N)(=O)=O)nc3)c(=O)n([C@@H](C)C(F)(F)F)c2n1] | 0.90 | 592.2 | A |

TABLE 1-continued

| Example | Structure | RT | m/z [M + H]+ | HPLC Method |
|---|---|---|---|---|
| 98 | 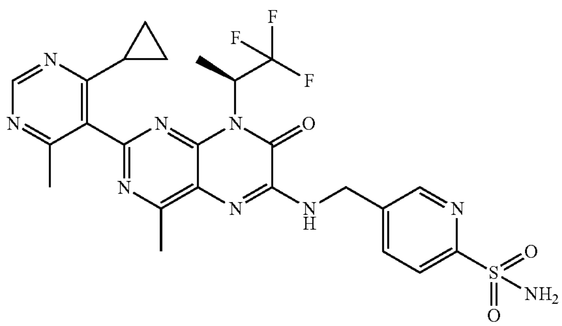 [SMILES: Cc1ncnc(C2CC2)c1-c1nc(C)c2nc(NCc3ccc(S(N)(=O)=O)nc3)c(=O)n([C@@H](C)C(F)(F)F)c2n1] | 0.85 | 576.3 | A |
| 99a | 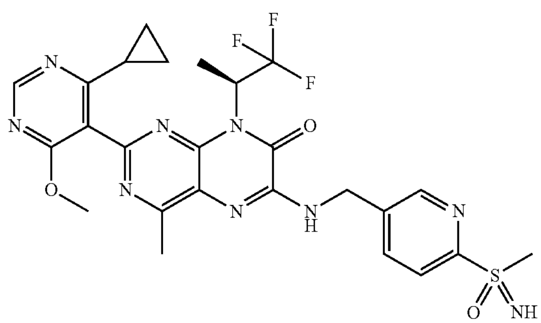 [SMILES: COc1ncnc(C2CC2)c1-c1nc(C)c2nc(NCc3ccc(S(C)(=N)=O)nc3)c(=O)n([C@@H](C)C(F)(F)F)c2n1] | 0.92 | 589.2 | A |
| 99b | 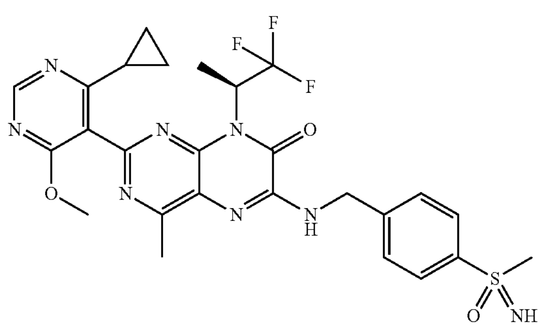 [SMILES: COc1ncnc(C2CC2)c1-c1nc(C)c2nc(NCc3ccc(S(C)(=N)=O)cc3)c(=O)n([C@@H](C)C(F)(F)F)c2n1] | 0.92 | 589.2 | A |
| 101a | 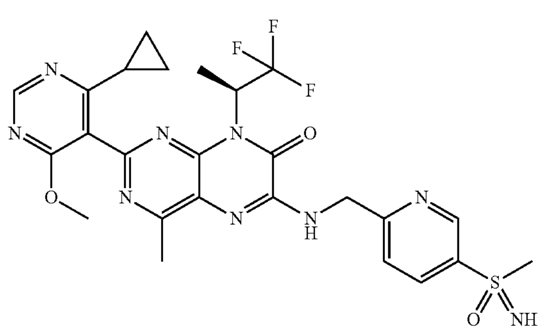 [SMILES: COc1ncnc(C2CC2)c1-c1nc(C)c2nc(NCc3ccc(S(C)(=N)=O)cn3)c(=O)n([C@@H](C)C(F)(F)F)c2n1] | 0.95 | 604.2 | A |

TABLE 1-continued

| Example | Structure | RT | m/z [M + H]+ | HPLC Method |
|---|---|---|---|---|
| 101b | 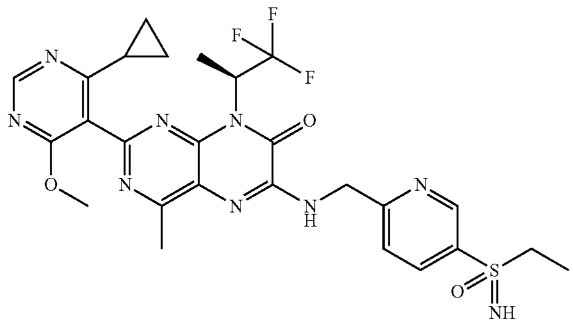 [SMILES: CCS(=N)(=O)c1ccc(CNc2nc3c(C)nc(-c4c(OC)ncnc4C4CC4)nc3n([C@@H](C)C(F)(F)F)c2=O)nc1] | 0.95 | 604.3 | A |
| 102a | 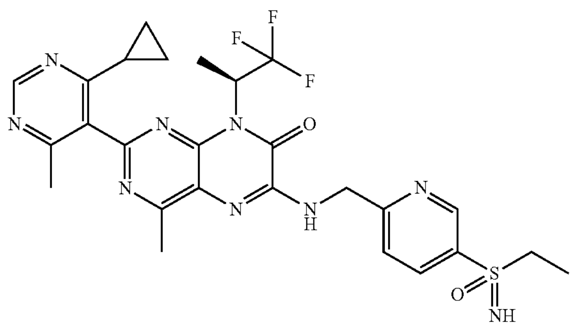 [SMILES: CCS(=N)(=O)c1ccc(CNc2nc3c(C)nc(-c4c(C)ncnc4C4CC4)nc3n([C@@H](C)C(F)(F)F)c2=O)nc1] | 0.89 | 588.3 | A |
| 102b | 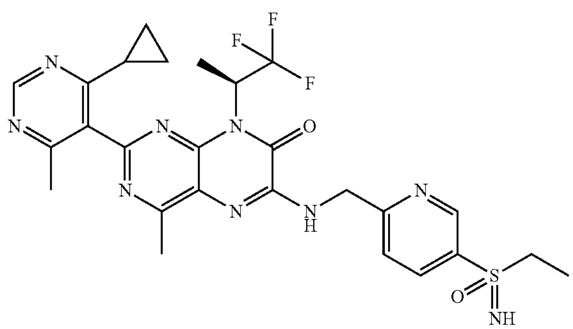 [SMILES: CCS(=N)(=O)c1ccc(CNc2nc3c(C)nc(-c4c(C)ncnc4C4CC4)nc3n([C@@H](C)C(F)(F)F)c2=O)nc1] | 0.89 | 588.2 | A |
| 105a | 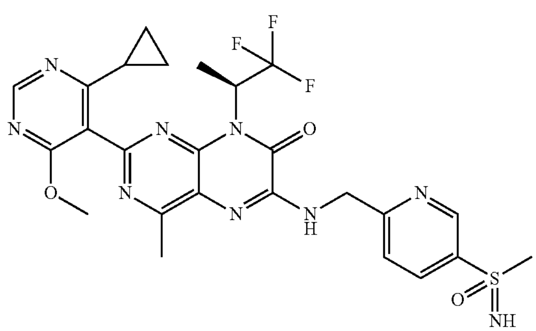 [SMILES: COc1ncnc(C2CC2)c1-c1nc(C)c2nc(NCc3ccc(S(C)(=N)=O)cn3)c(=O)n([C@@H](C)C(F)(F)F)c2n1] | 0.90 | 590.3 | A |

TABLE 1-continued

| Example | Structure | RT | m/z [M + H]+ | HPLC Method |
|---|---|---|---|---|
| 105b | 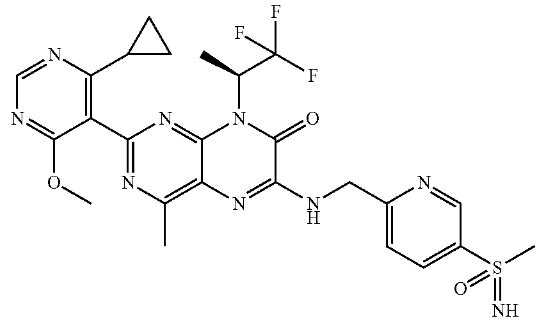 [SMILES: COc1ncnc(C2CC2)c1-c1nc(C)c2nc(NCc3ccc(S(C)(=N)=O)cn3)c(=O)n([C@@H](C)C(F)(F)F)c2n1] | 0.90 | 590.3 | A |
| 106a | 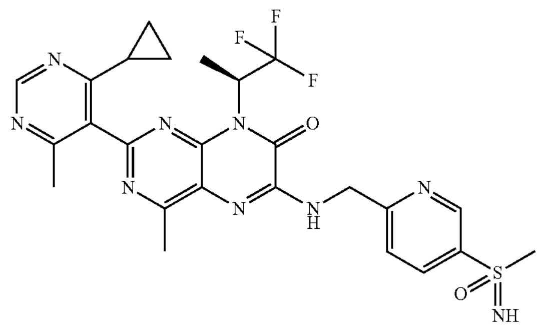 [SMILES: Cc1ncnc(C2CC2)c1-c1nc(C)c2nc(NCc3ccc(S(C)(=N)=O)cn3)c(=O)n([C@@H](C)C(F)(F)F)c2n1] | 0.84 | 574.2 | A |
| 106b | 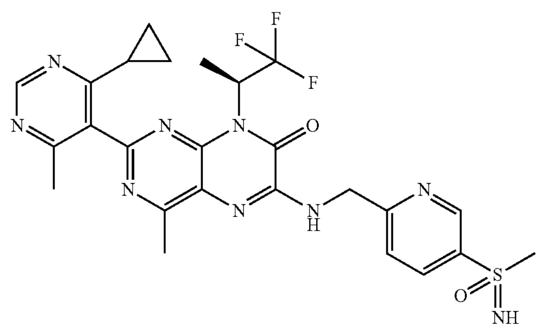 [SMILES: Cc1ncnc(C2CC2)c1-c1nc(C)c2nc(NCc3ccc(S(C)(=N)=O)cn3)c(=O)n([C@@H](C)C(F)(F)F)c2n1] | 0.84 | 574.2 | A |

In one embodiment, the invention relates to a compound selected from the group consisting of compounds 1-106b depicted in Table 1 above and the pharmaceutically acceptable salts thereof.

The present invention further relates to a pharmaceutically acceptable salt of a compound of the formula (I) with inorganic or organic acids or bases.

In another aspect, the invention relates to compounds of formula (I) or the pharmaceutically acceptable salts thereof as medicaments.

In another aspect, the invention relates to compounds of formula (I) or the pharmaceutically acceptable salts thereof for use in a method for treatment of a patient.

In another aspect, the invention relates to compounds of formula (I) or the pharmaceutically acceptable salts thereof for use in the treatment of autoimmune diseases and allergic disorders.

In another aspect, the invention relates to the use of compounds of formula (I) or the pharmaceutically acceptable salts thereof for preparing a pharmaceutical composition for the treatment of autoimmune diseases and allergic disorders.

In another aspect, the invention relates to a method for the treatment of autoimmune diseases and allergic disorders comprising administering a therapeutically effective amount of a compound of formula (I) or one of the pharmaceutically acceptable salts thereof to a patient.

In another aspect, the invention relates to a pharmaceutical composition containing as active substance one or more compounds of formula (I) or the pharmaceutically acceptable salts thereof optionally in combination with conventional excipients and/or carriers.

The compounds of formula (I) may be made using the general synthetic methods described below, which also constitute part of the invention.

General Synthetic Methods

The compounds according to the invention may be prepared by the methods of synthesis and synthetic examples below, methods known to those of ordinary skill in the art and methods reported in the chemical literature. In the methods of synthesis and examples described hereinafter, the substituents $R^1$, $R^2$, $R^3$, $R^4$, $R^5$, and W shall have the meanings defined hereinbefore in the detailed description of the compounds of formula I. The methods that are described here are intended as an illustration and for the enablement of the instant invention without restricting the scope of its subject matter, the claimed compounds, and the examples. Where the preparation of starting compounds is not described, they are commercially obtainable, may be prepared analogously to compounds or methods described herein, or are described in the chemical literature. Unless otherwise specified, solvents, temperatures, pressures, and other reaction conditions may be readily selected by one of ordinary skill in the art.

Compounds of formula (I) having $R^5$ being methyl may be prepared from intermediate A' according to Scheme I. The preparations of intermediates having other $R^5$ that are found in the embodiments are illustrated in Methods 16-19 in the Synthetic Examples section, below.

ture (e.g., about 120° C.) to provide a compound of formula B'. Alternatively, the said pyrimidine of formula A' wherein G is a suitable synthetic precursor for $NH_2$ (e.g., a nitro group) may be reacted with a suitable amine or amine salt (e.g., hydrochloride salt) of formula $R^4NH_2$ such as 1-methyl cyclopropylamine in the presence of a suitable reagent and solvent (e.g., i-$Pr_2$EtN and THF, respectively), and under a suitable reaction conditions such as an appropriate temperature (e.g., about −78° C. to about 25° C.) to afford an intermediate, which may be converted to a compound of formula B' upon further reaction with suitable reagents (e.g., a $NO_2$ group that may be reduced with a suitable reagent such as $SnCl_2$). The selection of a suitable amine of formula $R^4NH_2$ and pyrimidine of formula A' for the aforementioned reaction by a person skilled in the art

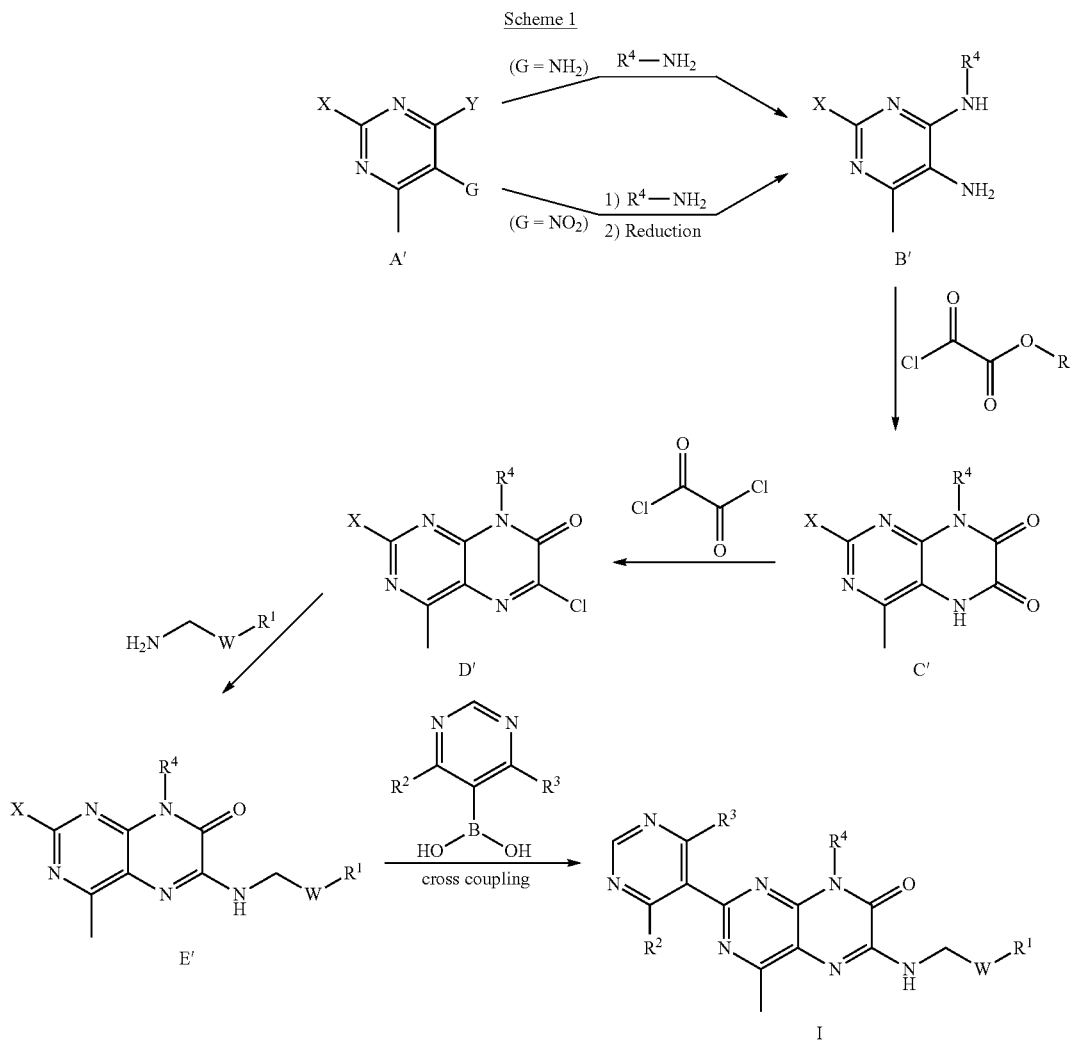

Scheme 1

As illustrated in Scheme I, a suitable pyrimidine of formula A', wherein G is $NH_2$, X is a suitable group for palladium-mediated cross coupling reactions (e.g., I, Br, Cl, or $OSO_2CF_3$), and Y is a suitable leaving group (e.g., Cl), may be reacted with a suitable amine or amine salt (e.g., hydrochloride salt) of formula $R^4NH_2$ such as isopropyl amine in the presence of a suitable base (e.g., i-$Pr_2$EtN, or $Et_3$N) in a suitable solvent (e.g., n-butanol) and under a suitable reaction conditions such as an appropriate temperamay be based on criteria such as steric and electronic nature of the amine and the pyrimidine. A diaminopyrimidine of formula B' may be reacted with a suitable reagent such as chloro-oxo-acetic acid ethyl ester in a suitable solvent (e.g., acetone) and in the presence of a suitable base (e.g., $K_2CO_3$) to furnish a compound of formula C'. A dicarbonyl compound of formula C' may be reacted with a suitable dehydrochlorinating reagent such as oxalyl chloride in the presence of a suitable additive (e.g., a catalytic amount of DMF)

in a suitable solvent (e.g., CH$_2$Cl$_2$), and under a suitable reaction conditions such as an appropriate temperature (e.g., about ambient temperature) to provide a compound of formula D'. A chloro-pteridinone of formula D' may be reacted with a suitable amine or amine salt of formula R$^1$—W—CH$_2$—NH$_2$ such as 4-ethanesulfonyl benzyl amine in the presence of a suitable base (e.g., Et$_3$N) in a suitable solvent (e.g., THF) and under a suitable reaction conditions such as an appropriate temperature (e.g., about ambient temperature) to yields a compound of formula E'. Intermediate E' may be heated with a suitable cross-coupling pyrimidine partner (e.g., a boronic acid) and a suitable base (e.g., K$_3$PO$_4$), in a suitable solvent (e.g., 1,4-dioxane), in the presence of a suitable cross-coupling catalyst (e.g., Pd(dppf)Cl$_2$), under suitable reaction conditions such as a suitable atmosphere (e.g., argon) and at a suitable temperature (e.g., about 100° C.) to provide a compound of formula (I).

Synthetic Examples

Non-limiting examples demonstrating the preparation of the compounds of the invention are provided below. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC (RP-HPLC). Discrete enantiomers may be obtained by resolution of racemic products using chiral HPLC. RP-HPLC purification methods used anywhere from 0-100% acetonitrile in water containing 0.1% formic acid or 0.1% TFA and used one of the following columns:
  a) Waters Sunfire OBD C18 5 μM 30×150 mm column
  b) Waters XBridge OBD C18 5 μM 30×150 mm column
  c) Waters ODB C8 5 μM 19×150 mm column
  d) Waters Atlantis ODB C18 5 μM 19×50 mm column
  e) Waters Atlantis T3 OBD 5 μM 30×100 mm column
  f) Phenomenex Gemini Axia C18 5 μM 30×100 mm column
UPLC/MS Methods:
  Analytical UPLC/MS Analysis Method A:
  Column: Waters CSH 2.1×50 mm C18 1.7 um column
  Gradient:

| Time (min) | 0.05% Formic Acid in Water | 0.05% Formic Acid in ACN | Flow (mL/min) |
|---|---|---|---|
| 0 | 90 | 10 | 0.8 |
| 1.19 | 0 | 100 | 0.8 |
| 1.77 | 0 | 100 | 0.8 |

LIST OF ABBREVIATIONS USED IN SYNTHETIC EXAMPLES

| Ac | Acetyl |
|---|---|
| ACN | Acetonitrile |
| AcOH | Acetic acid |
| aq | Aqueous |
| Bu | Butyl |
| Boc$_2$O | Di-tert-butyl dicarbonate |
| DCM | Dichloromethane |

-continued

| DIEA | N,N-diisopropylethylamine |
|---|---|
| DMAP | 4-Dimethylaminopyridine |
| DMF | N,N-Dimethylformamide |
| dppf | 1.1'-bis(diphenylphosphino)ferrocene |
| ES+ | Electron spray positive ionization |
| Et | Ethyl |
| EtOAc | Ethyl acetate |
| EtOH | Ethanol |
| h | hour(s) |
| HPLC | High performance liquid chromatography |
| i | Iso |
| LC | Liquid chromatography |
| Me | Methyl |
| MeOH | Methanol |
| min | Minutes |
| MS | Mass spectrometry |
| NMP | N-Methylpyrrolidinone |
| Pd/C | Palladium on carbon |
| Ph | Phenyl |
| PPh3 | Triphenylphosphine |
| Pr | Propyl |
| RaNi | Raney Nickel |
| RT | Retention time (HPLC) |
| rt | Ambient temperature |
| SFC | Supercritical Fluid Chromatography |
| t | Tertiary |
| tert | Tertiary |
| Tf | Triflate |
| TEA | Triethylamine |
| TFA | Trifluoroacetic acid |
| THF | Tetrahydrofuran |
| UPLC | Ultra Performance Liquid Chromatography |

Method 1

Synthesis of Intermediate B

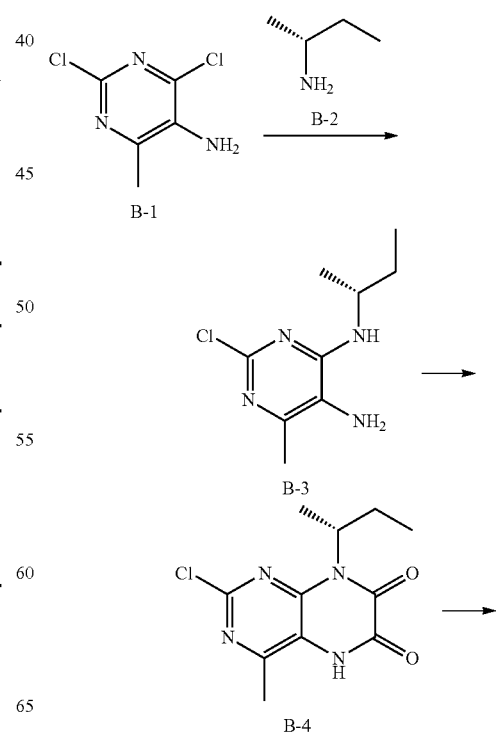

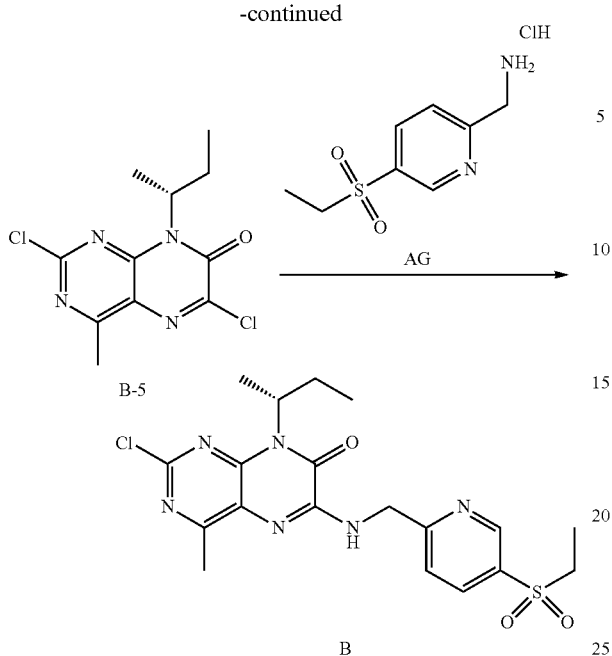

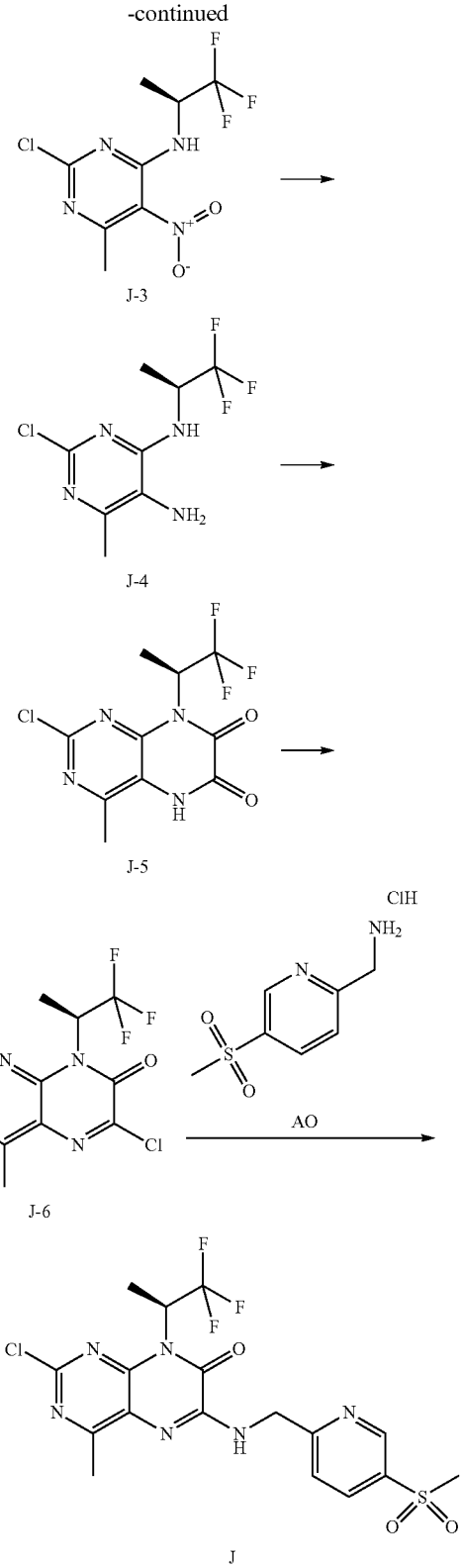

To a stirred suspension of B-1 (5.00 g, 28 mmol) in n-butanol (25 mL) is added B-2 (2.05 g, 28 mmol) followed by DIEA (9.93 mL, 56.2 mmol). The mixture is stirred for 15 h at 120° C. The reaction is cooled to rt and quenched by the addition of saturated aqueous NH$_4$Cl solution. The reaction is then diluted with EtOAc. The organic layer is separated and washed with water, followed by brine. The organic layer is dried (Na$_2$SO$_4$), decanted and concentrated. The resulting residue is purified by SiO$_2$ flash chromatography to yield B-3.

To a stirred suspension of B-3 (1.7 g, 8 mmol) in acetone (30 mL) is added ethyl chlorooxoacetate (0.97 mL, 8.7 mmol) followed by K$_2$CO$_3$ (3.39 g, 24.5 mmol). The mixture is stirred at rt for 18 h and the solid precipitate is isolated to yield B-4.

To a stirred suspension of B-4 (1.0 g, 3.72 mmol) in CH$_2$Cl$_2$ (20 mL) is added oxalyl chloride (0.64 mL) followed by 10 drops of DMF. The mixture is stirred for 5 h at rt. The mixture is then concentrated at reduced pressure to yield B-5.

To a stirred suspension of B-5 (400 mg, 1.0 mmol) in DMF (4 mL) is added DIEA (450 mg, 2.5 mmol) (or TEA), followed by AG (330 mg, 1.0 mmol). The reaction is allowed to stir for 6 h at rt. The reaction is quenched by the addition of cold water and the precipitate is filtered to yield intermediate B. MS (ES+): m/z 451.1 [M+H]$^+$.

Method 2

Synthesis of Intermediate J

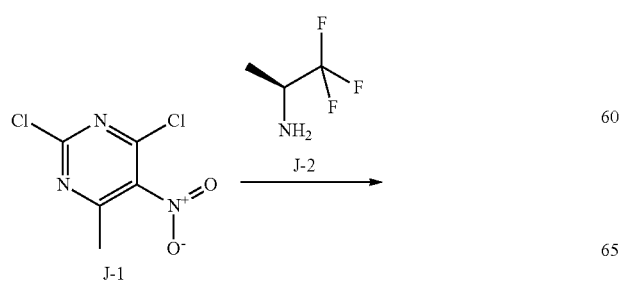

To a stirred suspension of J-1 (10.0 g, 48.0 mmol) and J-2 (8.94 g, 48.0 mmol) in DCM (150 mL) at 5° C. is added triethylamine (14.6 g, 144 mmol). The reaction is stirred at that temperature for 5 h. The solution is poured into water (200 mL), extracted with DCM (3×250 mL). The combined organic phase is dried (Na$_2$SO$_4$), decanted and concentrated. The resulting residue is purified by SiO$_2$ flash chromatography to yield J-3.

To a solution of J-3 (20.0 g, 48 mmol) in EtOH (180 mL) at 5° C. is added a solution of NH$_4$Cl (2.56 g, 48 mmol) in water (80 mL) and Fe (8.00 g, 143 mmol). The mixture is heated to 50° C. for 3 h. The reaction mixture is then poured into water (50 mL) and extracted with EtOAc (3×50 mL). The combined organic phase is dried (Na$_2$SO$_4$), decanted and concentrated. The crude product is purified by SiO$_2$ flash chromatography to yield J-4.

As an alternative procedure for the reduction of nitropyrimidine to the corresponding amino pyrimidine the following general procedure is utilized for analogous intermediates: To a solution of the nitropyrimidine in EtOH is added catalytic RaNi. The reaction vessel is evacuated and purged with N$_2$(g), then evacuated and filled with H$_2$(g). The reaction is maintained under H$_2$(g) atmosphere for 15 h. The vessel is evacuated and purged with N$_2$(g).

The reaction is filtered through a pad of diatomaceous earth to remove the Ni catalyst and the filtrate is concentrated. The resulting residue is purified by SiO$_2$ flash chromatography to afford the corresponding aminopyrimidine.

To a stirred solution of J-4 (6.05 g, 21.1 mmol) in DCM (100 mL) at 8° C. is added ethyl chlorooxoacetate (2.41 mL, 21.1 mmol). The reaction is stirred at 5-10° C. for 2 h. The reaction is then filtered, washed with DCM and redissolved in EtOH (100 mL). Triethylamine (5.94 mL, 42.3 mmol) is added and the mixture is heated to 90° C. for 1 h. The mixture is then cooled to rt and the pH of is adjusted to 5 with acetic acid. The reaction is then concentrated in vacuo and the residue is dissolved in DCM, washed with water, brine and concentrated. The residue is triturated in EtOAc/Heptanes to yield J-5.

To a solution of J-5 (1.00 g, 3.24 mmol) in CH$_2$Cl$_2$ (50 mL) is added oxalyl chloride (0.55 mL, 6.48 mmol) followed by 10 drops of DMF. The reaction is allowed to stir at rt for 18 h. The volatiles are removed in vacuo. The crude is redissolved in DCM and reconcentrated. The resulting residue yields J-6.

To a stirred solution of J-6 (550 mg, 1.68 mmol) in DMF (10 mL) is added AO (374 mg, 1.68 mmol) followed by DIEA (0.75 mL, 4.20 mmol). The reaction is stirred at rt and monitored by LC-MS until complete (~1 h). The reaction mixture is quenched with enough cold water to precipitate a solid. The mixture is stirred for 15 min and the solid is filtered to yield intermediate J. MS (ES+): m/z 477.2 [M+H]$^+$.

Method 3

Synthesis of Intermediate AB

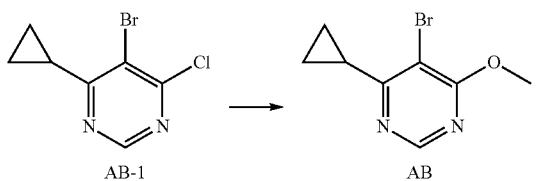

To a solution of AB-1 (300 mg, 1.29 mmol) in anhydrous MeOH (15 mL) is added NaOMe (208 mg, 3.86 mmol). The mixture is stirred at rt for 1 h. The solution is filtered and concentrated. The residue is purified by SiO$_2$ flash chromatography to yield intermediate AB. MS (ES+): m/z 230.8 [M+H]$^+$.

Method 4

Synthesis of Intermediate AC

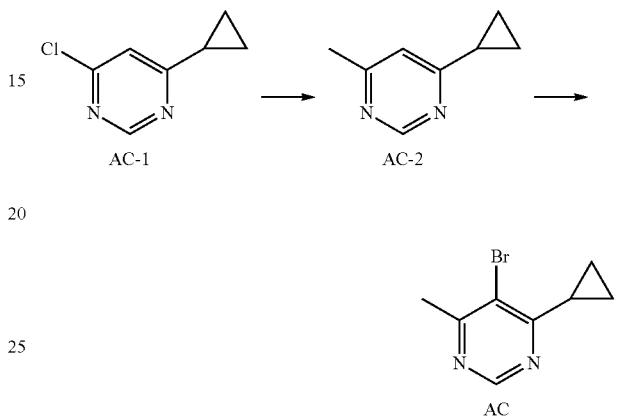

To a solution of AC-1 (320 mg, 2.07 mmol), 2,4,6-trimethyl-1,3,5,2,4,6-trioxatriborinane (520 mg, 4.14 mmol), and aq Na$_2$CO$_3$ (2M, 3.1 mL, 6.21 mmol) in dioxane (10 mL) is added dichloropalladium 4-di-tert-butylphosphanyl-N,N-dimethyl-aniline (73 mg, 0.10 mmol). The mixture is heated to 130° C. for 40 min in a microwave reactor. The mixture is diluted with MeOH (5 mL), filtered and concentrated. The residue is purified by SiO$_2$ flash chromatography to yield AC-2.

To a solution of AC-2 (363 mg, 2.71 mmol) in EtOH (10 mL) at −10° C. is added Br$_2$ (432 mg, 2.71 mmol). The reaction mixture is stirred at rt for 18 h. The solution is concentrated and the residue is purified by SiO$_2$ flash chromatography to yield intermediate AC. MS (ES+): m/z 214.3 [M+H]$^+$.

Method 5

A. Synthesis of Intermediate AD

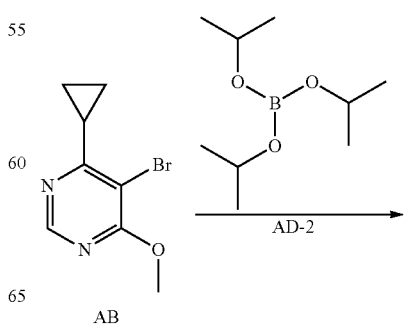

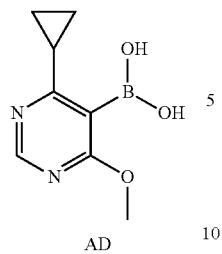

AD

To a solution of AB (6.00 g, 26.2 mmol) and AD-2 (7.86 mL, 34.1 mmol) in toluene (60 mL) and THF (18 mL) at −78° C. is added n-butyl lithium (12.6 mL, 31.4 mmol), dropwise, over 30 min. The solution is the stirred at −78° C. for 30 min and is then slowly warmed to −20° C. The solution is then quenched with 1 N HCl (40 mL). The layers are then separated and the aqueous layer is adjusted to pH ~8 with 2M NaOH. A white solid begins to precipitate and the mixture is cooled in the refrigerator for 1 h. The solids are filtered to yield intermediate AD. The aqueous layer is extracted with MeTHF and concentrated to give additional intermediate AD. MS (ES+): m/z 195.1 [M+H]$^+$.

B. Synthesis of Intermediate AE

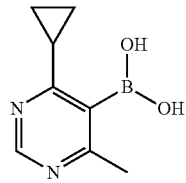

AE

To a solution of AC (see Method 4) (20 g, 93.86 mmol) in toluene (200 mL) and THF (50 mL) under Ar is added triisopropyl borate (28.2 mL, 122.02 mmol) and the resulting mixture is cooled to −74° C. n-BuLi (2.7 M in hexanes, 56.7 mL, 150.18 mmol) is added dropwise through additional funnel over 1 hour. After the addition, the reaction mixture is stirred at −74° C. for 5 min then quenched with 1N HCl aqueous solution (85 mL, 255.31 mmol). The mixture is slowly warmed up to room temperature then the layers are separated. To the stirring aqueous solution is added NaHCO$_3$ solid (10 g, 119.03 mmol). The product is collected by filtration.

Method 6

Synthesis of Intermediate AF

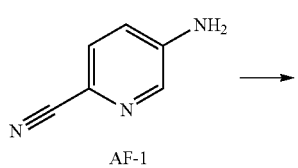

AF-1

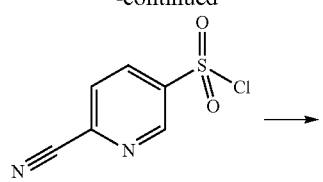

AF-2

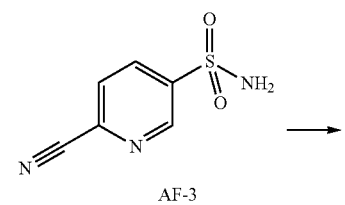

AF-3

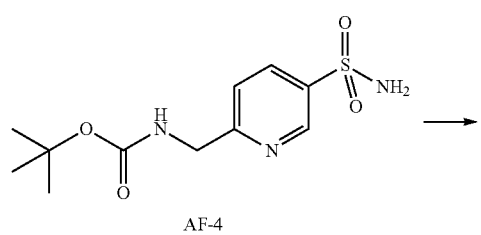

AF-4

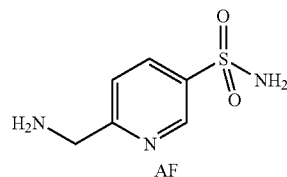

AF

AF-1 (20.0 g, 168 mmol) is added to conc. HCl (200 mL) at 0° C. followed by dropwise addition of aq NaNO$_2$ (25.5 g in 25 mL H$_2$O) maintaining an internal temperature of <5° C. The solution is allowed to stir at 0° C. for 15 min and then is slowly added to a mixture of SO$_2$ (108 g) and CuCl (84 mg) in AcOH (200 mL, >5 eq) at 5° C. The solution is stirred 90 min at 5° C. The reaction mixture is extracted with DCM (2×500 mL), dried (Na$_2$SO$_4$), and the organic solution of AF-2 used directly in the next step.

To a solution of AF-2 (20.0 g, 99 mmol) in DCM (200 mL) is added a solution of ammonia in MeOH (100 mL) at 0° C. and stirred at rt for 30 min. The mixture is concentrated to dryness and the resulting residue is purified by SiO$_2$ flash chromatography to yield AF-3.

To a solution of AF-3 (15.0 g, 82 mmol) in MeOH (200 mL) is added RaNi (10.0 g), TEA (34.4 mL) and Boc$_2$O (17.8 g). The mixture is stirred at rt under H$_2$ (50 psi) for 12 h. The vessel is purged with N$_2$, filtered and the filtrate concentrated. The residue is purified by SiO$_2$ flash chromatography to yield AF-4.

A solution of AF-4 (30.0 g, 105 mmol) in HCl in MeOH (500 mL) is stirred at rt for 12 h. The mixture is concentrated and recrystallized to yield intermediate AF. MS (ES+): m/z 188.1 [M+H]$^+$.

Method 7

Synthesis of Intermediate AG

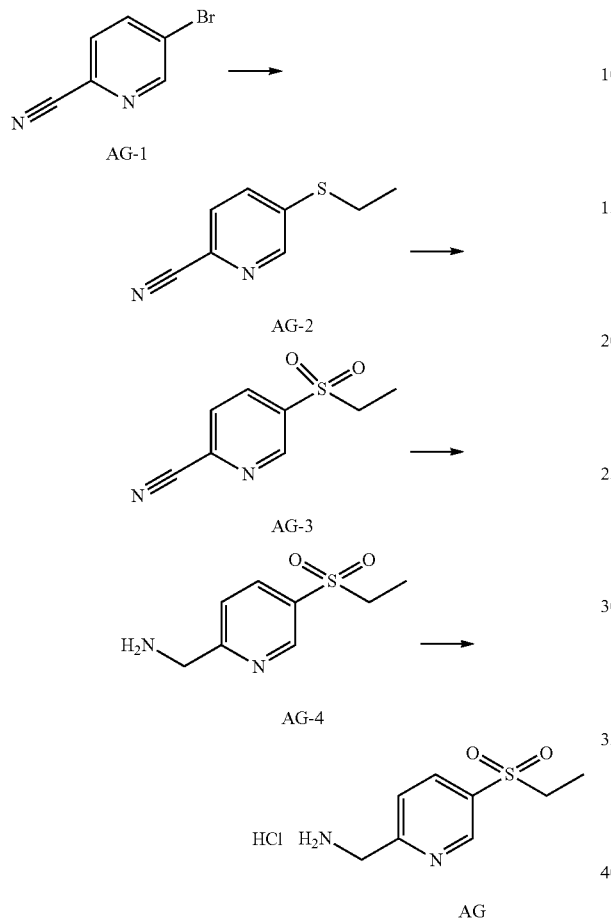

A mixture of AG-1 (8.0 g, 43.96 mmol), K$_2$CO$_3$ (7.88 g, 57.1 mmol) and sodium ethanethiolate (4.06 g, 48.3 mmol) in NMP (60.0 mL) under N$_2$ is stirred at rt for 18 h. The reaction mixture is poured into H$_2$O and filtered. The solids are washed with H$_2$O and dried under vacuum to yield AG-2.

To a suspension of AG-2 (6.0 g, 36.6 mmol) in AcOH (2.63 g, 43.8 mmol) is added a solution of KMnO$_4$ (5.78 g, 36.6 mmol) in H$_2$O (20.0 mL) dropwise. The reaction mixture is stirred at rt for 15 h. The mixture is diluted with water and extracted with EtOAc. The organic layer is dried (Na$_2$SO$_4$), decanted and concentrated. The resulting residue is purified by SiO$_2$ flash chromatography to yield AG-3.

A solution of AG-3 (3.3 g, 16.8 mmol) and Pd/C (500 mg, 10% on carbon catalyst) in MeOH (30 mL) is stirred at rt under H$_2$ (50 psi) for 8 h. The vessel is purged with N$_2$, filtered and the filtrate concentrated to yield AG-4.

To a stirred solution of AG-4 (2.5 g, 12.5 mmol) in EtOAc (30 mL) is added HCl in EtOAc (2N, 20.0 mL). The solution is stirred at rt for 5 h and then filtered to yield intermediate AG. MS (ES+): m/z 201.2 [M+H]$^+$.

Method 8

Synthesis of Intermediate AH

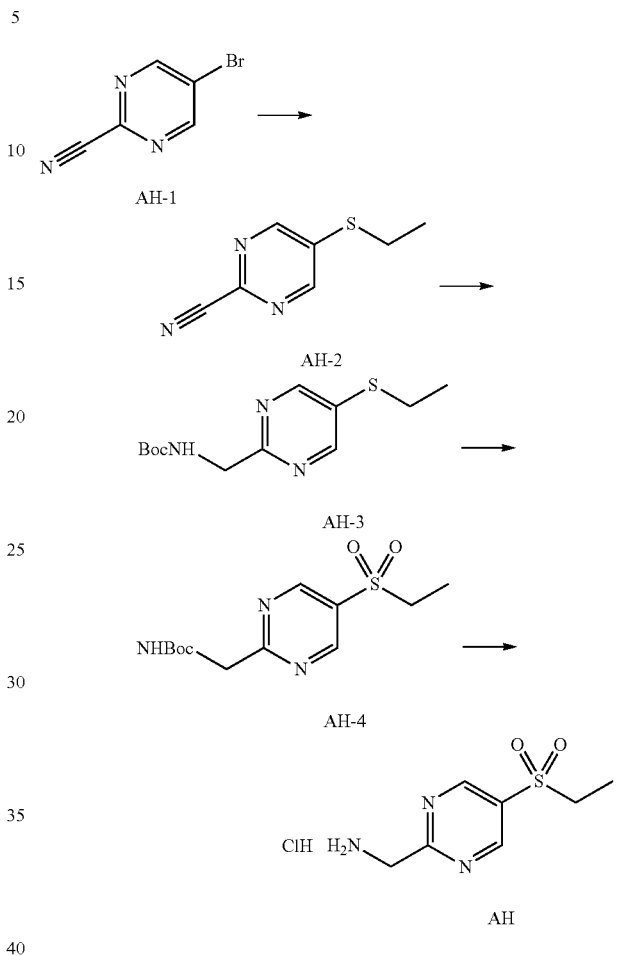

A mixture of AH-1 (113 g, 0.62 mol), K$_2$CO$_3$ (171 g, 1.24 mol) and sodium ethanethiolate (67 g, 0.80 mol) in DMF (2 L) is stirred at rt under N$_2$ for 18 h. The mixture is diluted with H$_2$O and extracted with EtOAc. The organic layers are dried (Na$_2$SO$_4$), decanted and concentrated. The resulting residue is purified by SiO$_2$ flash chromatography to yield AH-2.

A solution of AH-2 (20.0 g, 0.12 mol), RaNi (40 g), Boc$_2$O (31.7 g, 0.14 mol) and TEA (24.5 g, 0.24 mol) in THF (600 mL) is stirred at rt under H$_2$ (50 psi) for 12 h. The mixture is filtered and the filtrate concentrated under reduced pressure. The resulting residue is purified by SiO$_2$ flash chromatography to yield AH-3.

To a suspension of AH-3 (65 g, 0.24 mol) in AcOH (200 mL) at −10° C. is added dropwise a solution of KMnO$_4$ (45.8 g, 0.29 mol) in water (500 mL). Following complete addition, the reaction mixture is stirred at rt for 30 min. The mixture is diluted with H$_2$O and basified by addition of aqueous Na$_2$CO$_3$ to ~pH 8 and extracted with EtOAc. The combined organic layers are dried (Na$_2$SO$_4$), decanted, and concentrated. The resulting residue is purified by crystallization to yield AH-4.

To a stirred solution of compound AH-4 (46.5 g, 0.15 mol) in MeOH (300 mL) is added 4M HCl in MeOH (300 mL) at rt and stirred for 15 h. The mixture is concentrated under reduced pressure. The resulting residue is purified by crystallization to yield intermediate AH. MS (ES+): m/z 202.1 [M+H]$^+$.

Intermediate AI and Intermediate AJ are synthesized in a fashion analogous to Intermediate AH.

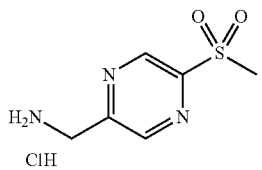

AI

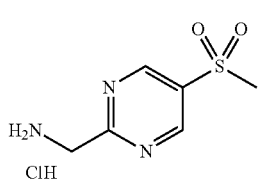

AJ

Method 9

Synthesis of Intermediate AK

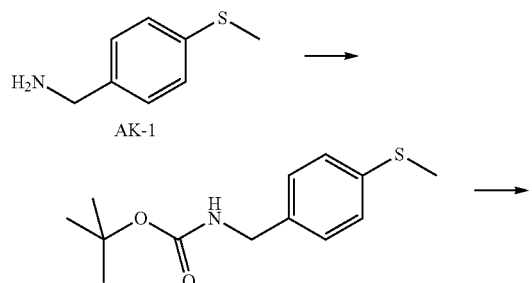

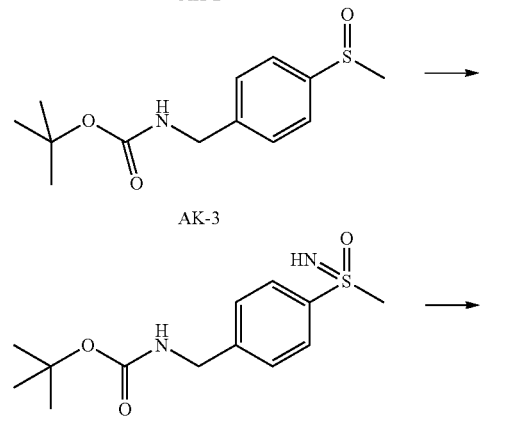

To a solution of AK-1 (2.00 g, 13.1 mmol) in THF (25 mL) is added Boc$_2$O (3.45 mL, 15.0 mmol) and TEA (3.64 mL, 26.1 mmol). The reaction mixture is stirred at rt for 18 h and then diluted with H$_2$O and extracted with EtOAc. The organic layers are concentrated to yield AK-2.

To solution of AK-2 (3.3 g, 13.1 mmol) in AcOH (10 mL) is slowly added H$_2$O$_2$ (1.37 mL, 13.7 mmol). The reaction mixture is stirred at rt for 3 h and is then quenched with saturated Na$_2$SO$_3$ solution and neutralized with 1N NaOH. The mixture is extracted with EtOAc and concentrated to yield AK-3.

A mixture of AK-3 (1.0 g, 3.7 mmol), MgO (600 mg, 14.9 mmol), trifluoroacetamide (839 mg, 7.4 mmol), and Rh(II) acetate dimer (115 mg, 0.26 mmol) in DCM (10 mL) is added (diacetoxyiodo)benzene (1.79 g, 5.6 mmol). The mixture is stirred at rt for 18 h and then concentrated under reduced pressure. The resulting residue is dissolved in MeOH, filtered through a pad of diatomaceous earth and, K$_2$CO$_3$ (2.55 g, 18.6 mmol) is added to the filtrate. The mixture is stirred at rt for 18 h and is concentrated under reduced pressure. The resulting residue is purified by SiO$_2$ flash chromatography to yield AK-4.

To a stirred solution of compound AK-4 (585 mg, 2.1 mmol) in DCM (2 mL) is added HCl in dioxane (4N, 2 mL). The reaction mixture is stirred at rt for 15 h and then concentrated under reduced pressure to yield intermediate AK. MS (ES+): m/z 185.0 [M+H]$^+$.

Method 10

Synthesis of Intermediate AL

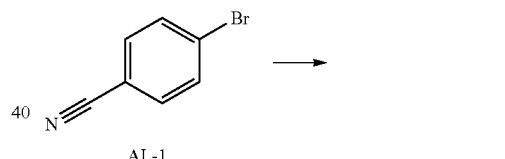

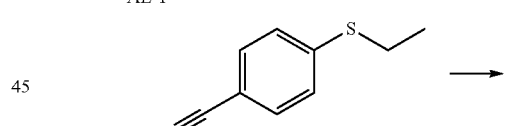

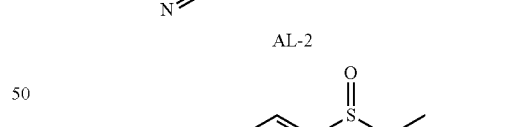

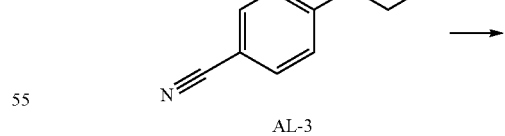

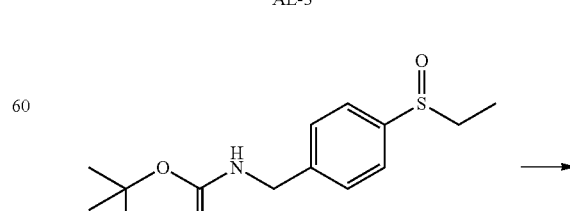

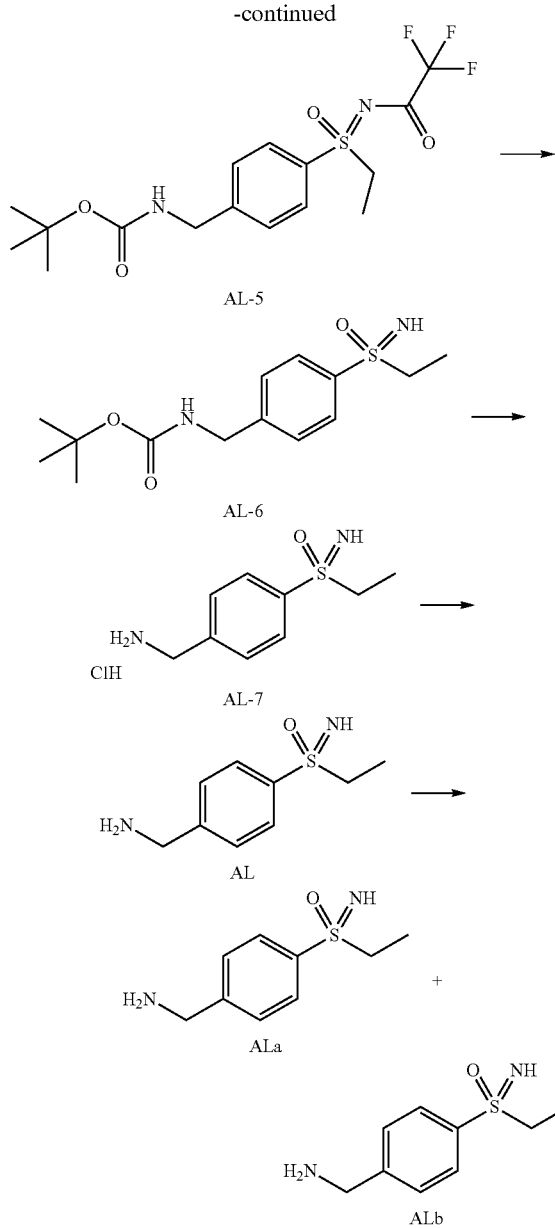

RaNi (10 g) in MeOH (150 mL) is stirred at 40° C. under $H_2$ (50 psi) for 12 h. The mixture is filtrated through celite. The filtrate is concentrated. The residue is purified by silica gel chromatography (Petroleum ether:EtOAc=20:1 to 1:1) to afford AL-4.

A mixture of compound AL-4 (15 g, 0.053 mol), 2,2,2-Trifluoro-acetamide (6.6 g, 0.058 mol), MgO (4.3 g, 0.106 mol), PhI(OAc)$_2$ (17.1 g, 0.053 mol) and Rh catalyst (1.5 g) in DCM (150 mL) is stirred at 20° C. for 12 h. The mixture is filtrated. The filtrate is concentrated to yield crude AL-5. The crude product is used directly in the next step.

A mixture of compound AL-5 (20 g, 0.030 mol) and $K_2CO_3$ (8.4 g, 0.061 mol) in MeOH (200 mL) is stirred at 20° C. for 12 h. The mixture is filtrated. The filtrate is concentrated. The residue is purified by silica gel chromatography (Petroleum ether:EtOAc=3:1 to 1:1) to afford AL-6.

A solution of compound AL-6 (18 g, 0.030 mol) in HCl-MeOH (200 mL) is stirred at 20° C. for 3 h. The reaction mixture is concentrated. The residue is washed with DCM (50 mL×2) to afford AL-7.

To a mixture of compound AL-7 (13 g) in MeOH (300 mL) is added ion exchange resin until pH≥8. Then the mixture is stirred at room temperature for 1 h. The mixture is filtrated. The filtrate is concentrated to yield AL.

AL-8 is separated by SFC to give ALa and ALb.

Intermediate AM and Intermediate AN (as the HCl salt. MS (ES+): m/z 202.1 [M+H]$^+$) are synthesized in a fashion analogous to intermediate AL, with the exception of the SFC separation is carried out at the Boc stage (after step 5).

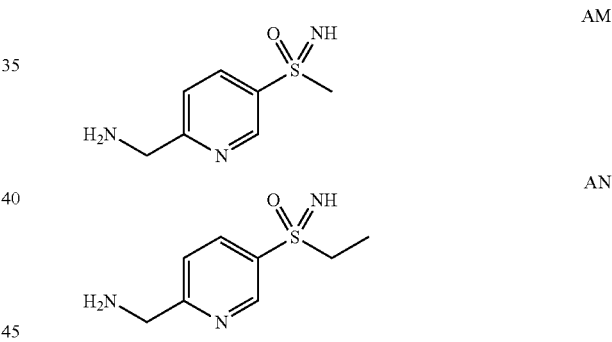

To a mixture of ethanethiol (49.2 g, 0.79 mol) in ACN (2 L) is added NaOtBu (126.5 g, 1.32 mol) at 0° C. under $N_2$. The mixture is stirred at 0° C. for 0.5 h. Then AL-1 (40 g, 0.66 mol) is added into the mixture. The reaction mixture is warmed to 50° C. and stirred for 11.5 h. The reaction is quenched by ice-water (500 mL) slowly and then extracted with EtOAc (IL×2). The combined organic phase is washed with brine (500 mL), dried over Na$_2$SO$_4$, filtered and concentrated to dryness. The residue is purified by column chromatography (Petroleum Ether:EtOAc=40:1 to 10:1) to yield AL-2.

A mixture of AL-2 (22 g, 0.135 mol) and $H_2O_2$ (15.4 mL) in ACN (220 mL) is stirred at 70° C. for 36 h. The mixture is quenched by $H_2O$ (200 mL), extracted with EtOAc (300 mL×2). The organic layer is dried with anhydrous Na$_2$SO$_4$, filterated and concentrated. The residue is purified by silica gel chromatography (Petroleum ether:EtOAc=20:1 to 5:1) to afford AL-3.

A mixture of compound AL-3 (10.4 g, 0.058 mol), Boc$_2$O (13.9 g; 1.1 eq.; 0.064 mol), TEA (19.5 mL; 2.5 eq.) and SFC Conditions for Separation of Sulfoximine Enantiomers
Racemic sulfoximine intermediates AK. AL, AM and AN were separated by SFC using one of the following conditions A, B, C or D:
A. Separation of AK
Instrument: Thar SFC80 preparative SFC
Column: Chiralpak AD-H 250*30 mm i.d. 5u
Mobile phase: A for $C_{O2}$ and B for MeOH (0.1% NH3H2O)
Gradient: B %=35%
Flow rate: 62 g/min
Wavelength: 220 nm
Column temperature: 40° C.
System back pressure: 100 bar
B. Separation of AN
Instrument: Thar SFC80 preparative SFC
Column: Chiralpak AD-H 250*30 mm i.d. 5u
Mobile phase: A for CO$_2$ and B for EtOH (0.1% NH$_3$H$_2$O)
Gradient: B %=40%
Flow rate: 65 g/min
Wavelength: 220 nm
Column temperature: 40° C.

System back pressure: 100 bar
C. Separation of AL
Instrument: Thar SFC80 preparative SFC
Column: Chiralpak AD-H 250*30 mm i.d. 5u
Mobile phase: A for CO$_2$ and B for MeOH (0.1% NH$_3$H$_2$O)
Gradient: B %=40%
Flow rate: 65 g/min
Wavelength: 220 nm
Column temperature: 40° C.
System back pressure: 100 bar
D. Separation of AM
Instrument: Thar SFC80 preparative SFC
Column: Chiralpak AD-H 250*30 mm i.d. 5u
Mobile phase: A for CO$_2$ and B for MeOH (0.1% NH$_3$H$_2$O)
Gradient: B %=35%
Flow rate: 60 g/min
Wavelength: 220 nm
Column temperature: 40° C.
System back pressure: 100 bar Chiral sulfoximine final compounds and intermediates derived from the first eluting enantiomer of AK, AL, AM or AN are labeled in the tables with an A or a. Those derived from the second eluting enantiomer are labeled with a B or b, for example, 26a and 26b.

Method 11

Synthesis of Intermediate AO

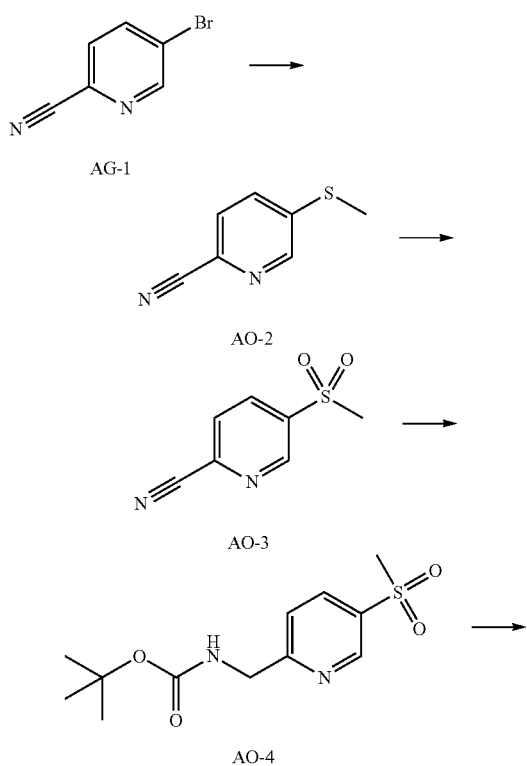

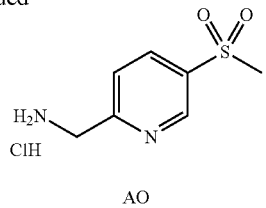

To a solution of AG-1 (82.0 g, 448 mmol) in ACN (1.0 L) is added sodium t-butoxide (64.5 g). The mixture is cooled to 0° C. and sodium methanethiolate (172.5 g, 20% in H$_2$O) is added dropwise. The reaction mixture is then allowed to stir at rt for 16 h. Water (800 mL) is added and the mixture is extracted with DCM. The combined organic phases are washed with brine, dried (Na$_2$SO$_4$) and concentrated. The residue is purified by SiO$_2$ flash chromatography to yield AO-2.

To a suspension of AO-2 (51.5 g, 343 mmol) in AcOH (500 mL) is added a solution of KMnO$_4$ (59.7 g, 36.6 mmol) in H$_2$O (500.0 mL) dropwise at 5° C. The reaction mixture is then stirred at rt for 1 h. The mixture is extracted with EtOAc, washed with aq. NaHCO$_3$, dried (Na$_2$SO$_4$) and concentrated. The resulting residue is purified by recrystallization to yield AO-3.

To a solution of AO-3 (15.0 g, 82 mmol) in MeOH (200 mL) is added RaNi (10.0 g), TEA (34.4 mL) and Boc$_2$O (17.8 g). The mixture is stirred at rt under H$_2$ (50 psi) for 12 h. The vessel is purged with N$_2$, filtered and the filtrate concentrated. The residue is purified by SiO$_2$ flash chromatography to yield AO-4.

A solution of AO-4 (30.0 g, 105 mmol) in HCl in MeOH (500 mL) is stirred at rt for 12 h. The mixture is concentrated and recrystallized to yield intermediate AO. MS (ES+): m/z 187 [M+H]$^+$.

Intermediate AP and Intermediate AQ (as the HCl salt. MS (ES+): m/z 202.1 [M+H]$^+$) are synthesized in a fashion analogous to intermediate AO.

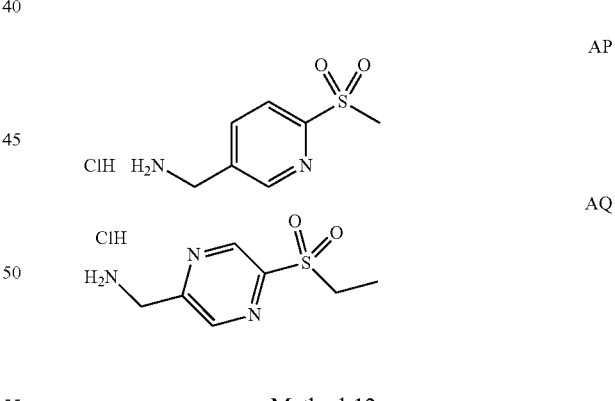

Method 12

Synthesis of Intermediate AR

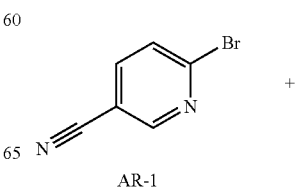

-continued

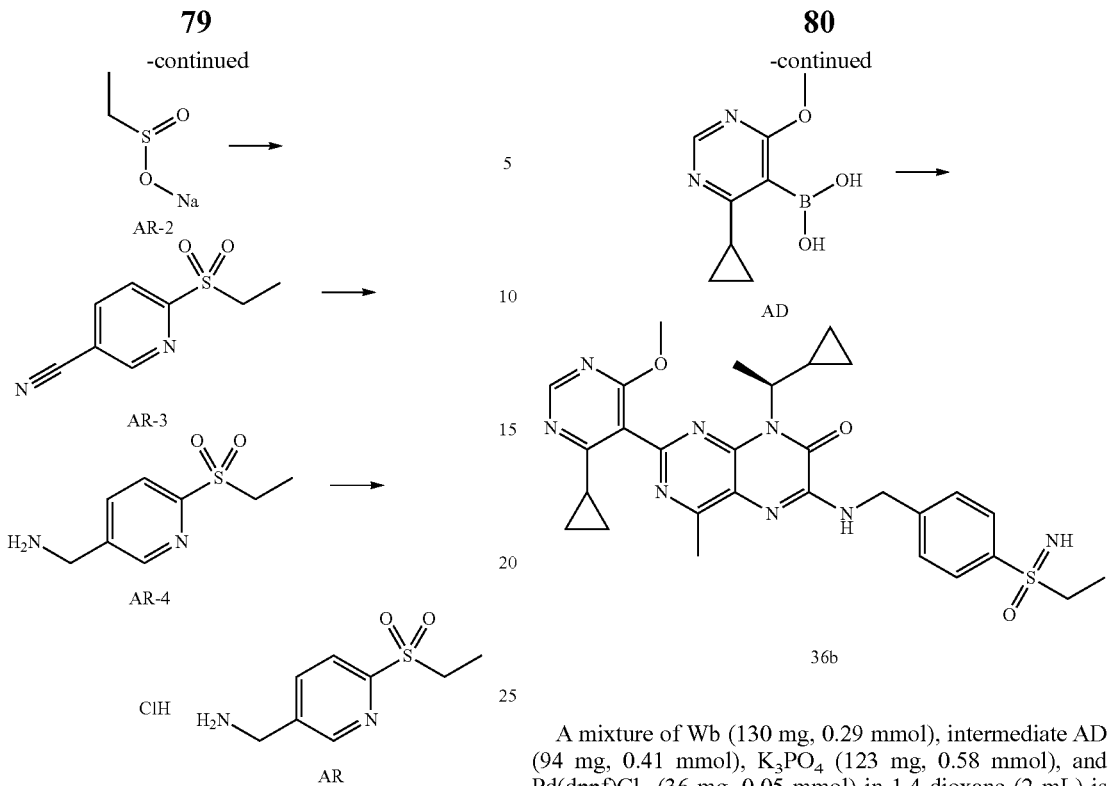

To a mixture of AR-1 (10.0 g, 55 mmol), N,N-dimethyl-ethane-1,2-diamine (0.96 g, 11 mmol) and Copper(II) trifluoromethanesulfonate (1.98, 5 mmol) in DMSO (100 mL) is added AR-2 (8.27 g, 98 mmol) at rt. The mixture is then heated to 120° C. for 30 min, quenched with H₂O and extracted with EtOAc. The organic layer is dried, concentrated and purified by SiO₂ flash chromatography to yield AR-3.

A mixture of AR-3 (32.3 g, 165 mmol) and Pd (3.50 g, 33 mmol) in NH₄OH (30 mL)/EtOH (200 mL) is stirred at rt under H₂ (15 psi) for 15 h. The mixture is filtered, concentrated and purified by SiO₂ flash chromatography to yield AR-4.

To a stirred solution of AR-4 (17.5 g, 87 mmol) in EtOH (100 mL) is added HCl in EtOH (100 mL). The solution is stirred at rt for 3 h and then concentrated and recrystallized to yield intermediate AR. MS (ES+): m/z 201 [M+H]⁺.

Method 13

Synthesis of Example 36b

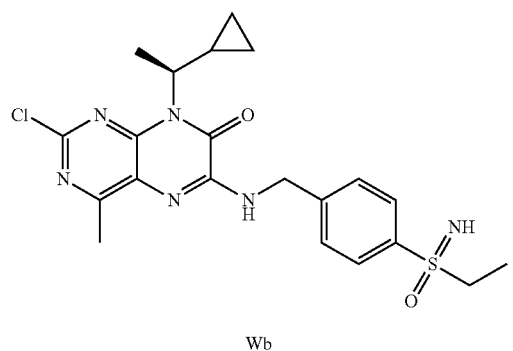

A mixture of Wb (130 mg, 0.29 mmol), intermediate AD (94 mg, 0.41 mmol), K₃PO₄ (123 mg, 0.58 mmol), and Pd(dppf)Cl₂ (36 mg, 0.05 mmol) in 1,4-dioxane (2 mL) is purged with argon, and then H₂O (0.5 mL) is added. The mixture is stirred at 100° C. for 18 h. After cooling to rt, the mixture is diluted with water (2 mL) and extracted with EtOAc (2×5 mL). The combined organic phase is dried (Na₂SO₄), decanted and concentrated. The resulting residue is purified by SiO₂ flash chromatography followed by reverse phase HPLC to yield Example 36b. MS (ES+): m/z 561.2 [M+H]+.

Method 14

Synthesis of Example 18

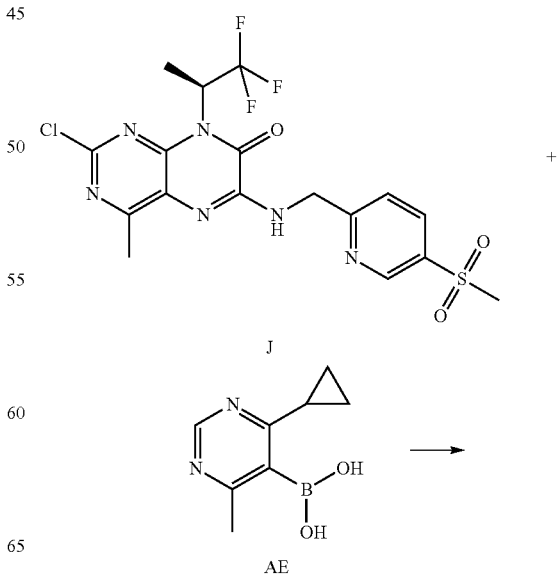

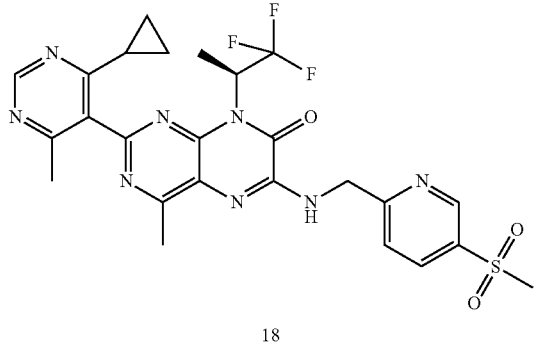

18

A mixture of J (5.0 g, 10.5 mmol), intermediate AE (3.0 g, 16.8 mmol), K₃PO₄ (5.6 g, 23.0 mmol), and Pd(dppf)Cl₂ (1.7 g, 2.1 mmol) in 1,4-dioxane (150 mL) and water (25 mL) is purged with argon. The mixture is stirred at 120° C. for 3 h. After cooling to rt, the aqueous layer is separated and the organic layer is concentrated. The residue is the dissolved in DCM and loaded onto KP—NH silica and eluted with DCM (500 mL). The organic phase is again concentrated and the residue is purified by purified by SiO₂ flash chromatography to yield Example 18. MS (ES+): m/z 575.4 [M+H]⁺.

Method 15

Synthesis of Example 23

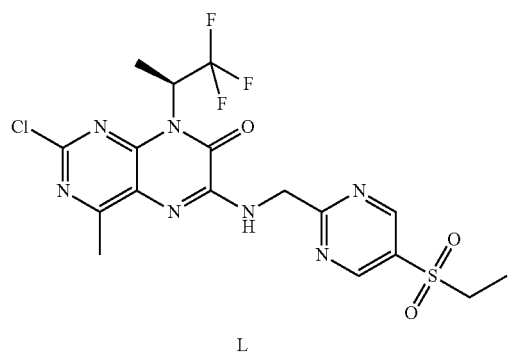

L

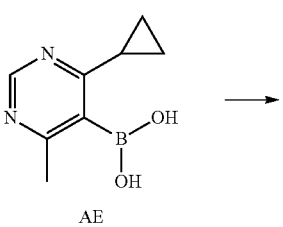

AE

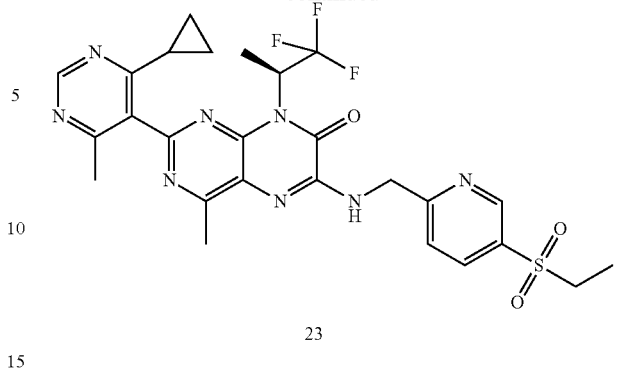

23

A mixture of L (1.7 g, 3.45 mmol), intermediate AE (1.23 g, 6.91 mmol), K₃PO₄ (1.47 g, 6.91 mmol), and Pd(dppf)Cl₂ (423 mg, 0.52 mmol) in 1,4-dioxane (40 mL) and water (10 mL) is purged with argon. The mixture is stirred at 120° C. for 3 h. After cooling to rt, the aqueous layer is separated and the organic layer is concentrated. The residue is the dissolved in DCM and loaded onto KP—NH silica and eluted with DCM (300 mL). The organic phase is again concentrated and the residue is purified by purified by SiO₂ flash chromatography to yield Example 23. MS (ES+): m/z 590.4 [M+H]⁺.

Method 16

Synthesis of Example 1

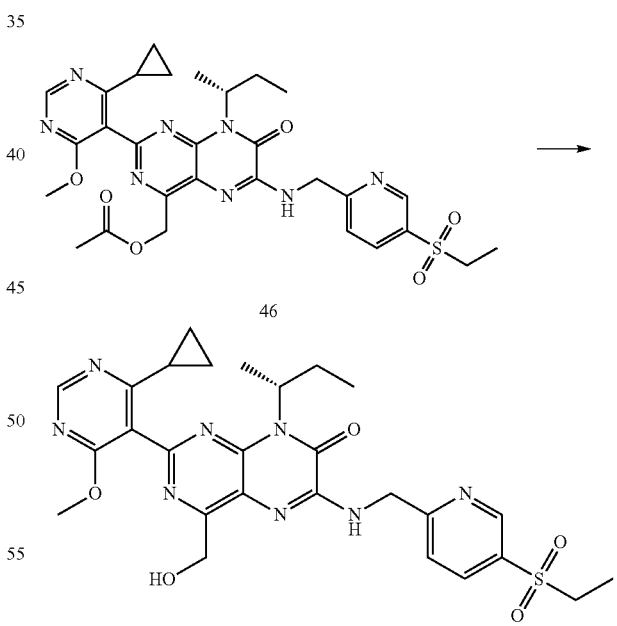

To a solution of 46 (30 mg, 0.48 mmol) in MeOH (1 mL) is added 4 M HCl in dioxane (0.5 mL, 2.00 mmol). The reaction is stirred at rt for 2 h. The mixture is concentrated and is purified by reverse phase HPLC (41-61% ACN/H2O) to give 1. MS (ES+): m/z 581.5 [M+H]⁺. Example 51 and 52 synthesized in an analogous fashion to Example 1.

Method 17

Synthesis of Intermediate K

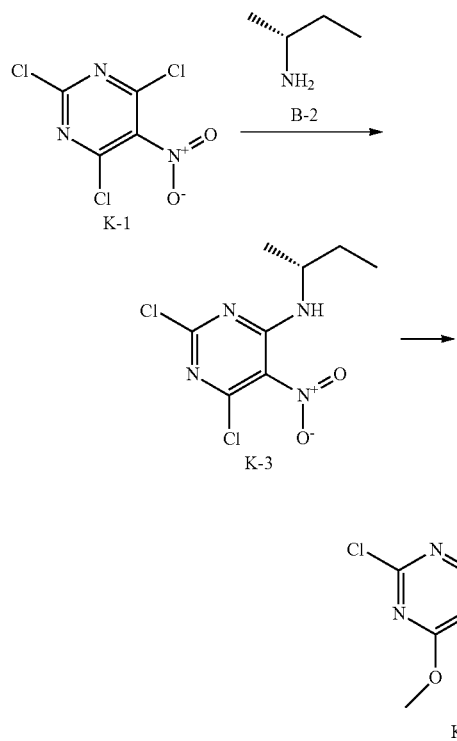

To a stirred suspension of K-1 (1.00 g, 4.38 mmol) and DIEA (1.83 mL, 10.51 mmol) in DCM (15 mL) at 0° C. is slowly added K-2 (1.00 g, 9.30 mmol) and the reaction is allowed to slowly warm to 25° C. and stirred for 4 h. The volatiles are removed under reduced pressure and the resulting residue is purified by SiO₂ flash chromatography to yield K-3.

To a solution of K-3 (1.00 g, 3.77 mmol) in THF (20 mL) at 0° C. is added a solution of sodium methoxide in MeOH (8.29 mL, 4.15 mmol). The reaction mixture is allowed to warm to rt and stir overnight. The volatiles are removed under reduced pressure and the resulting residue is purified by SiO₂ flash chromatography to yield K-4.

The remainder of the synthesis is analogous to Method 2.

Method 18

Synthesis of Intermediate GG

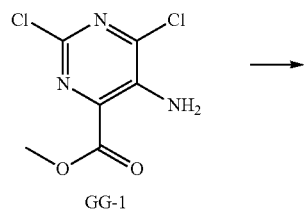

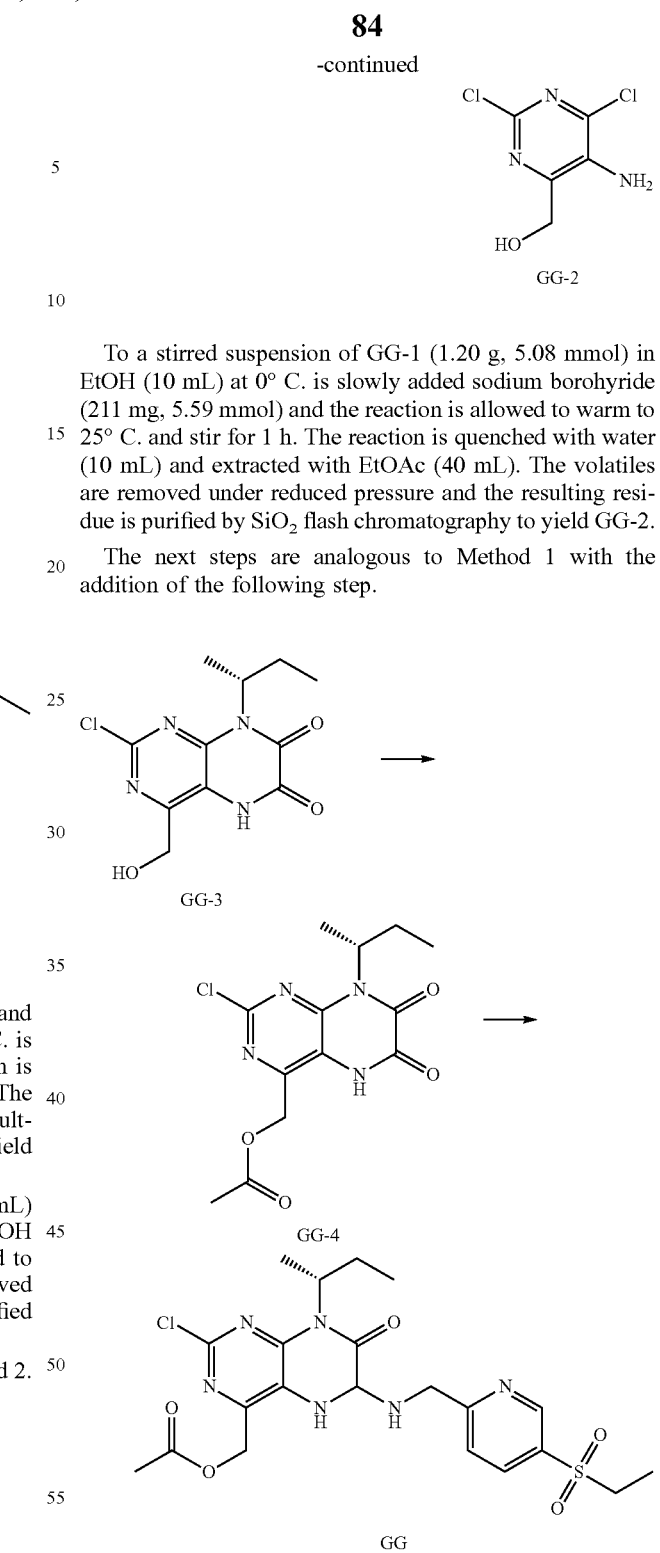

To a stirred suspension of GG-1 (1.20 g, 5.08 mmol) in EtOH (10 mL) at 0° C. is slowly added sodium borohyride (211 mg, 5.59 mmol) and the reaction is allowed to warm to 25° C. and stir for 1 h. The reaction is quenched with water (10 mL) and extracted with EtOAc (40 mL). The volatiles are removed under reduced pressure and the resulting residue is purified by SiO₂ flash chromatography to yield GG-2.

The next steps are analogous to Method 1 with the addition of the following step.

To a slurry of GG-3 (1.48 g, 5.20 mmol) and DMAP (140 mg, 1.14 mmol) is added acetic anhydride (4 mL) and Et3N (2.26 mL, 16.1 mmol). The suspension is allowed to stir at rt for 20 min. The reaction is diluted with water (25 mL) and extracted with EtOAc (40 mL). The volatiles are removed under reduced pressure and the resulting residue is purified by SiO₂ flash chromatography to yield GG4. GG-4 is converted to intermediate GG as in Method 1

Intermediate HH is prepared in an analogous fashion to Intermediate GG.

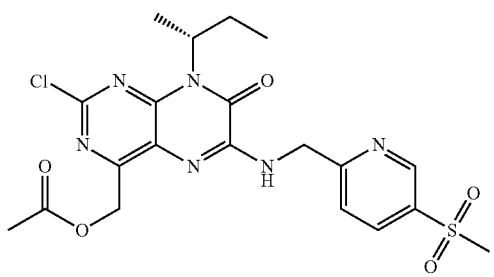

HH

Method 19

Synthesis of Example 53

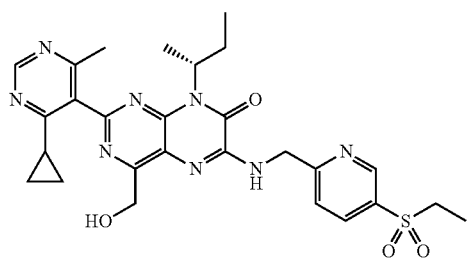

51

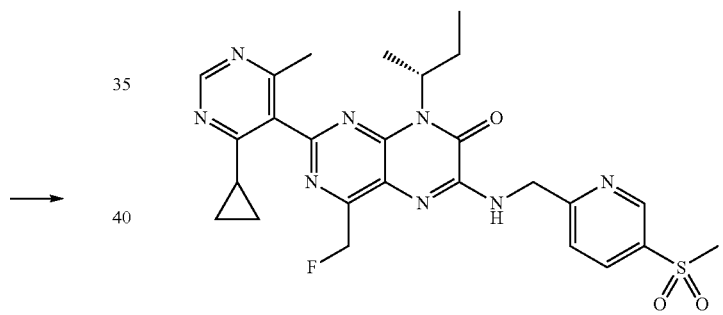

53

To a stirring solution of DAST, 1M in DCM (0.14 mL, 0.14 mmol) in DCM (5 mL) @-78 C is added dropwise over 1 min 51 (27 mg, 0.048 mmol) as a solution in DCM (2 mL). The reaction is stirred at −78 C for 10 min then rt for 1 h. The reaction is quenched with sat. $NaHCO_3$ (8 mL) with vigorous stirring for 15 min. The mixture is extracted with DCM (2×8 mL) and the organics dried ($Na_2SO_4$) and concentrated. The crude is purified by silica gel chromatography (MeOH/DCM) and product fractions are concentrated to a solid. Trituration in EtOAc/heptane yields product 53. LCMS (ESI+) m/z=567.2.

Example 54 is synthesized from intermediate 52 in an analogous manner as Example 53. LCMS (ESI+) m/z=553.2.

54

Table 2 summarizes the synthetic method used to prepare intermediates A-QQQb and the m/z found for each intermediate.

TABLE 2

| Intermediate | Structure | Synthetic Method | m/z [M + H]+ |
|---|---|---|---|
| A | 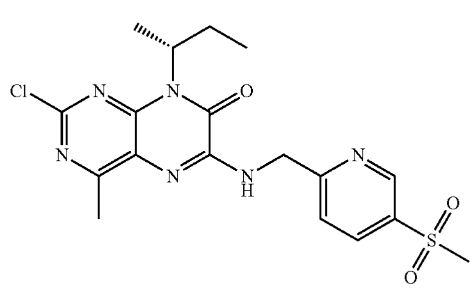 [SMILES: CC[C@@H](C)n1c(=O)c(NCc2ccc(S(C)(=O)=O)cn2)nc2c(C)nc(Cl)nc21] | 1 | 437.3 |

TABLE 2-continued

| Intermediate | Structure | Synthetic Method | m/z [M + H]+ |
| --- | --- | --- | --- |
| B | *structure* | 1 | 451.3 |
| C | *structure* | 1 | 452.2 |
| D | *structure* | 2 | 449.2 |
| E | *structure* | 2 | 464.3 |
| F | *structure* | 2 | 449.2 |

TABLE 2-continued

| Intermediate | Structure | Synthetic Method | m/z [M + H]+ |
|---|---|---|---|
| G | 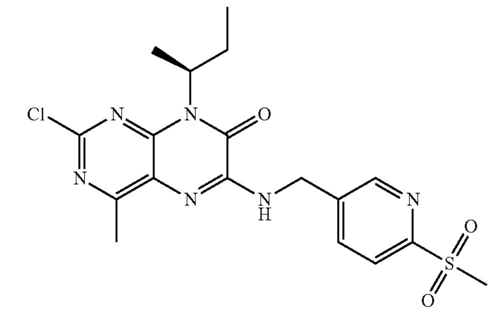 [SMILES: CC[C@H](C)n1c(=O)c(NCc2ccc(S(C)(=O)=O)nc2)nc2c(C)nc(Cl)nc21] | 2 | 437.3 |
| H | 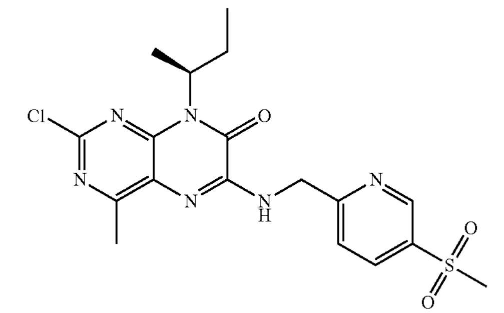 [SMILES: CC[C@H](C)n1c(=O)c(NCc2ccc(S(C)(=O)=O)cn2)nc2c(C)nc(Cl)nc21] | 2 | 437.3 |
| I | 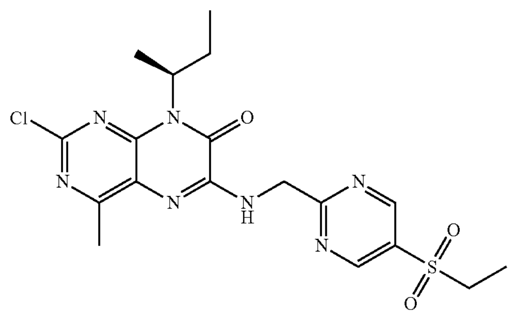 [SMILES: CC[C@H](C)n1c(=O)c(NCc2ncc(S(=O)(=O)CC)cn2)nc2c(C)nc(Cl)nc21] | 2 | 452.3 |
| J | 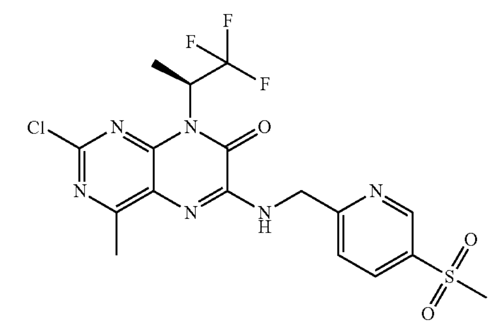 [SMILES: Cc1nc(Cl)nc2c1nc(NCc1ccc(S(C)(=O)=O)cn1)c(=O)n2[C@@H](C)C(F)(F)F] | 2 | 477.2 |
| K | 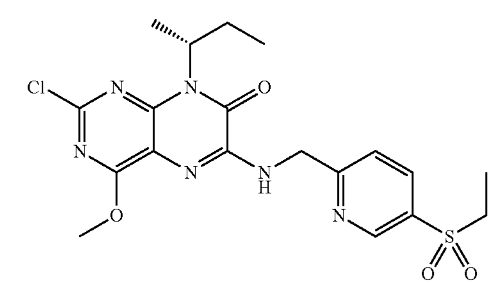 [SMILES: CC[C@@H](C)n1c(=O)c(NCc2ccc(S(=O)(=O)CC)cn2)nc2c(OC)nc(Cl)nc21] | 17 | 467.3 |

TABLE 2-continued

| Intermediate | Structure | Synthetic Method | m/z [M + H]+ |
|---|---|---|---|
| L | 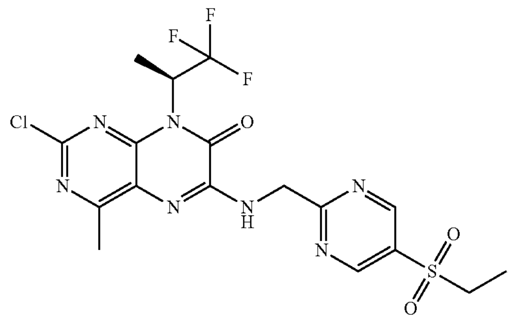 | 2 | 492.2 |
| M | 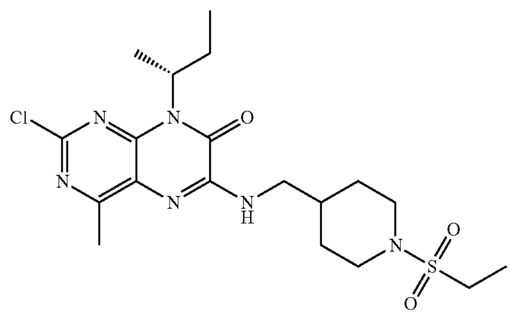 [SMILES: CC[C@@H](C)n1c(=O)c(NCC2CCN(S(=O)(=O)CC)CC2)nc2c(C)nc(Cl)nc21] | 1 | 457.1 |
| N | 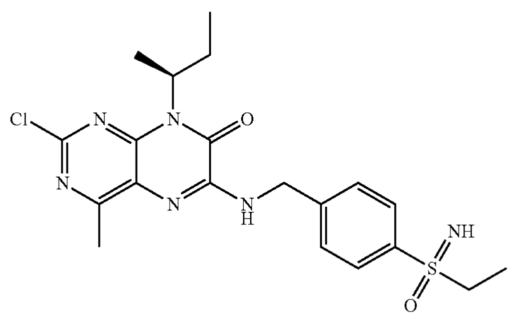 [SMILES: CC[C@H](C)n1c(=O)c(NCc2ccc(S(=N)(=O)CC)cc2)nc2c(C)nc(Cl)nc21] | 2 | 449.1 |
| Oa | 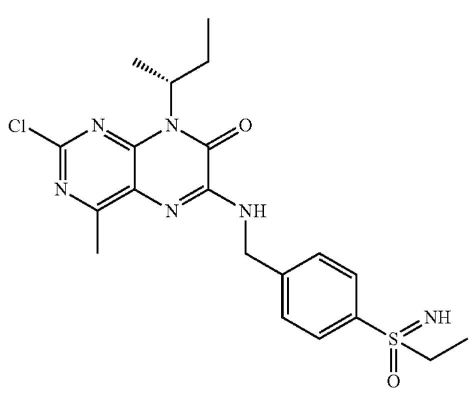 [SMILES: CC[C@@H](C)n1c(=O)c(NCc2ccc(S(=N)(=O)CC)cc2)nc2c(C)nc(Cl)nc21] | 1 | 449.1 |

TABLE 2-continued

| Intermediate | Structure | Synthetic Method | m/z [M + H]⁺ |
|---|---|---|---|
| Ob | 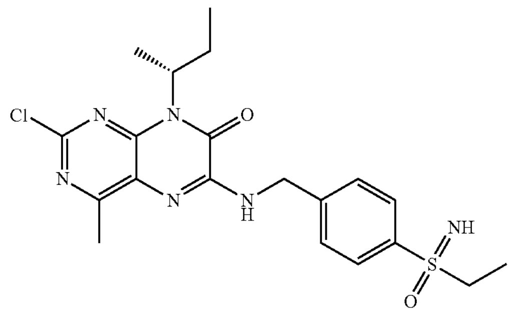 [SMILES: CC[C@@H](C)n1c(=O)c(NCc2ccc(S(=N)(=O)CC)cc2)nc2c(C)nc(Cl)nc21] | 1 | 449.1 |
| Pa | 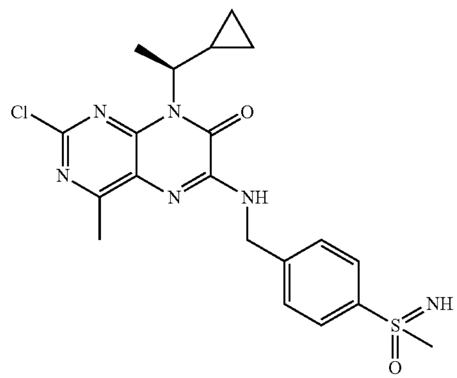 [SMILES: Cc1nc(Cl)nc2c1nc(NCc1ccc(S(C)(=N)=O)cc1)c(=O)n2[C@@H](C)C1CC1] | 2 | 447.2 |
| Pb | 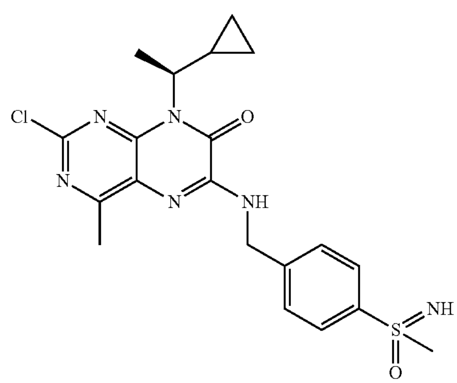 [SMILES: Cc1nc(Cl)nc2c1nc(NCc1ccc(S(C)(=N)=O)cc1)c(=O)n2[C@@H](C)C1CC1] | 2 | 435.1 |
| R | 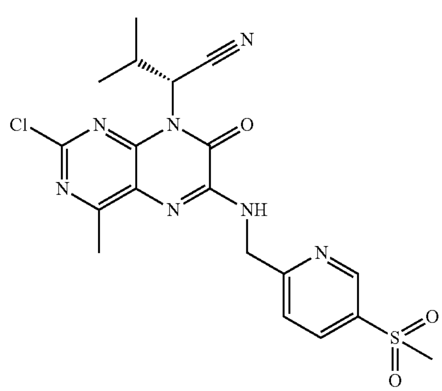 | 2 | 462.3 |

TABLE 2-continued

| Intermediate | Structure | Synthetic Method | m/z [M + H]+ |
|---|---|---|---|
| T | 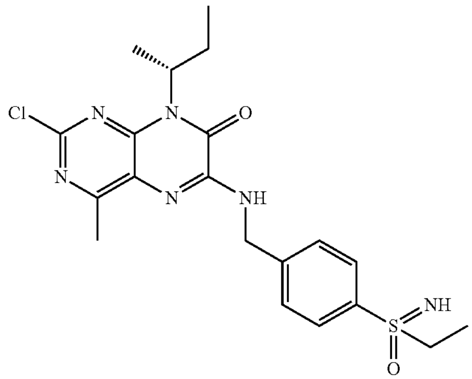 [SMILES: CC[C@@H](C)n1c(=O)c(NCc2ccc(S(=N)(=O)CC)cc2)nc2c(C)nc(Cl)nc21] | 1 | 449.1 |
| Ua | 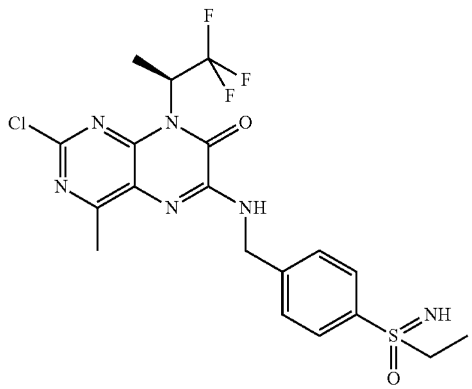 [SMILES: CCS(=N)(=O)c1ccc(CNc2nc3c(C)nc(Cl)nc3n([C@@H](C)C(F)(F)F)c2=O)cc1] | 2 | 489.2 |
| Ub | 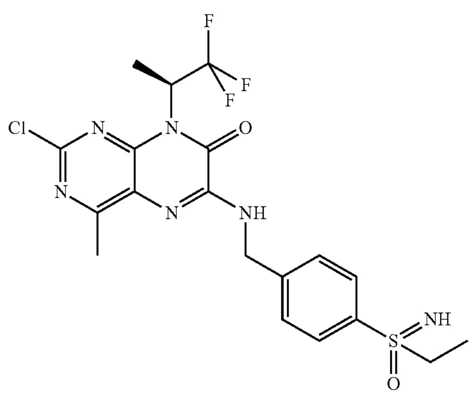 [SMILES: CCS(=N)(=O)c1ccc(CNc2nc3c(C)nc(Cl)nc3n([C@@H](C)C(F)(F)F)c2=O)cc1] | 2 | 489.3 |
| Wa | 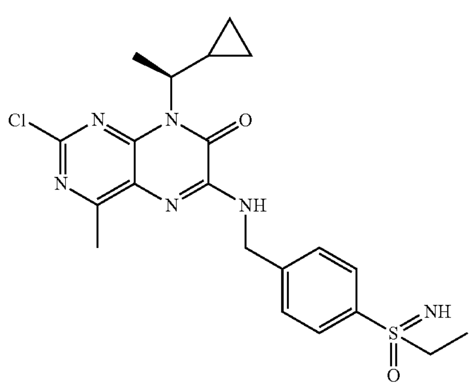 [SMILES: CCS(=N)(=O)c1ccc(CNc2nc3c(C)nc(Cl)nc3n([C@@H](C)C3CC3)c2=O)cc1] | 2 | 461.1 |

TABLE 2-continued

| Intermediate | Structure | Synthetic Method | m/z [M + H]+ |
|---|---|---|---|
| Wb | 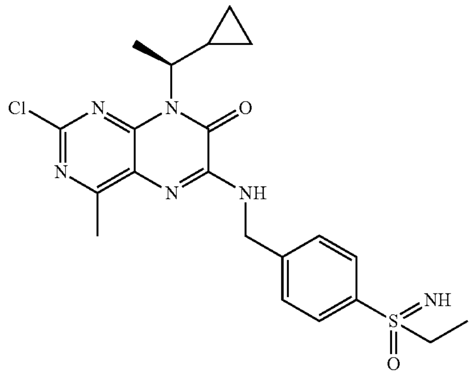 [SMILES: CCS(=N)(=O)c1ccc(CNc2nc3c(C)nc(Cl)nc3n([C@@H](C)C3CC3)c2=O)cc1] | 2 | 461.1 |
| X | 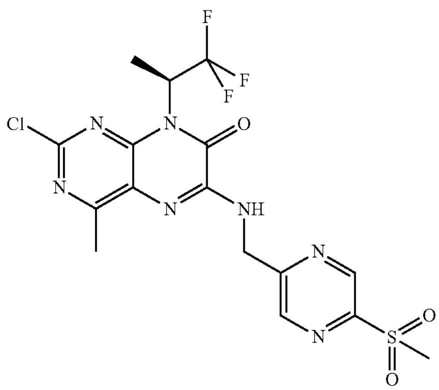 [SMILES: Cc1nc(Cl)nc2c1nc(NCc1cnc(S(C)(=O)=O)cn1)c(=O)n2[C@@H](C)C(F)(F)F] | 2 | 478.1 |
| Ya | 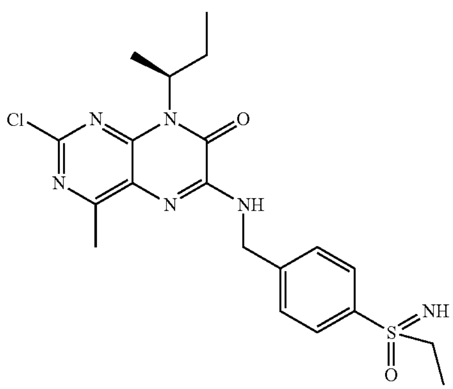 [SMILES: CC[C@H](C)n1c(=O)c(NCc2ccc(S(=N)(=O)CC)cc2)nc2c(C)nc(Cl)nc21] | 2 | 449.1 |
| Yb | 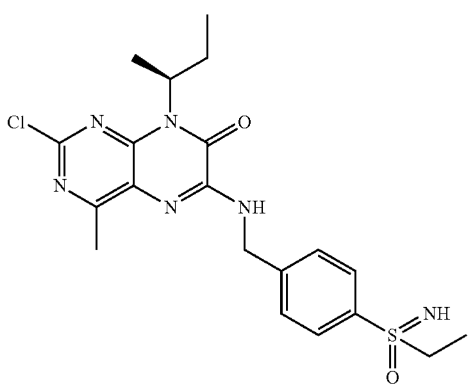 [SMILES: CC[C@H](C)n1c(=O)c(NCc2ccc(S(=N)(=O)CC)cc2)nc2c(C)nc(Cl)nc21] | 2 | 449.1 |

TABLE 2-continued

| Intermediate | Structure | Synthetic Method | m/z [M + H]+ |
|---|---|---|---|
| BB | 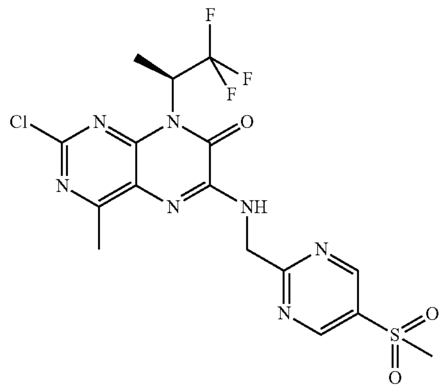 [SMILES: Cc1nc(Cl)nc2c1nc(NCc1ncc(S(C)(=O)=O)cn1)c(=O)n2[C@@H](C)C(F)(F)F] | 2 | 478.1 |
| CCa | 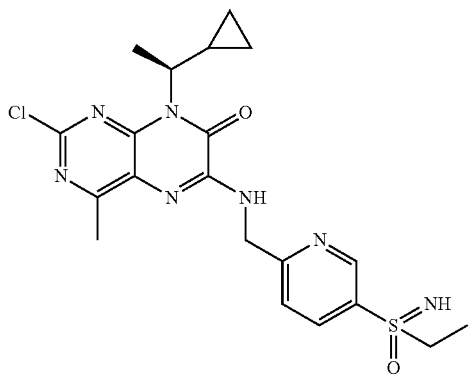 [SMILES: CCS(=N)(=O)c1ccc(CNc2nc3c(C)nc(Cl)nc3n([C@@H](C)C3CC3)c2=O)nc1] | 2 | 462.3 |
| CCb | 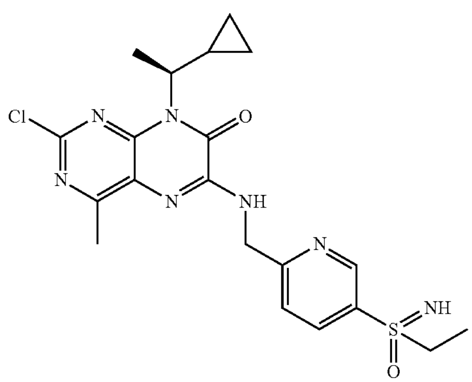 [SMILES: CCS(=N)(=O)c1ccc(CNc2nc3c(C)nc(Cl)nc3n([C@@H](C)C3CC3)c2=O)nc1] | 2 | 462.3 |
| DDa | 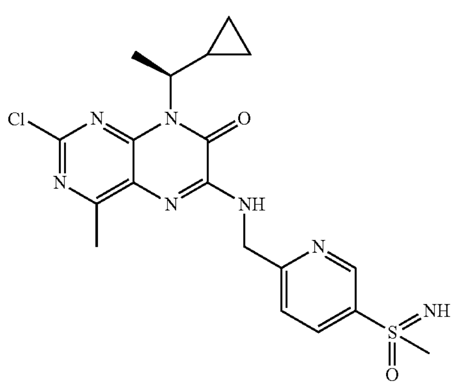 [SMILES: Cc1nc(Cl)nc2c1nc(NCc1ccc(S(C)(=N)=O)cn1)c(=O)n2[C@@H](C)C1CC1] | 2 | 448.2 |

TABLE 2-continued
| Intermediate | Structure | Synthetic Method | m/z [M + H]+ |
|---|---|---|---|
| DDb | 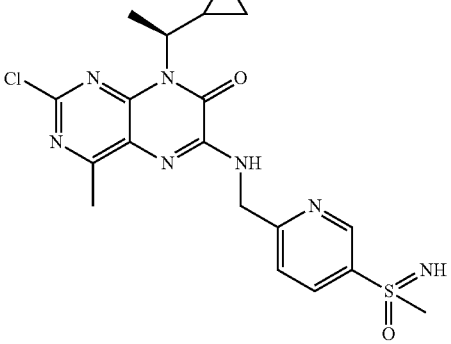 | 2 | 448.2 |
| GG | 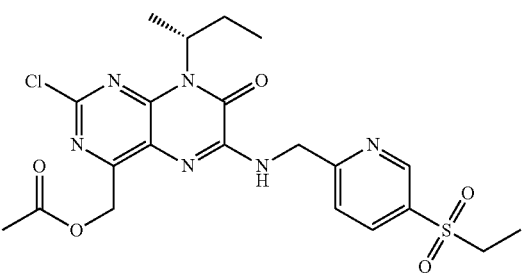 [SMILES: CC[C@@H](C)n1c(=O)c(NCc2ccc(S(=O)(=O)CC)cn2)nc2c(COC(C)=O)nc(Cl)nc21] | 18 | 509.2 |
| HH | 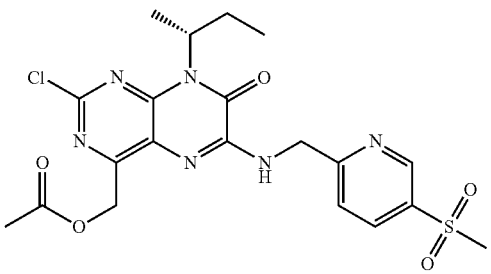 [SMILES: CC[C@@H](C)n1c(=O)c(NCc2ccc(S(C)(=O)=O)cn2)nc2c(COC(C)=O)nc(Cl)nc21] | 18 | 495.3 |
| II | 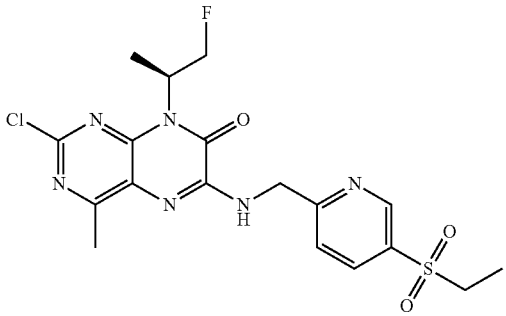 [SMILES: CCS(=O)(=O)c1ccc(CNc2nc3c(C)nc(Cl)nc3n([C@@H](C)CF)c2=O)nc1] | 2 | 455.5 |
| JJ | 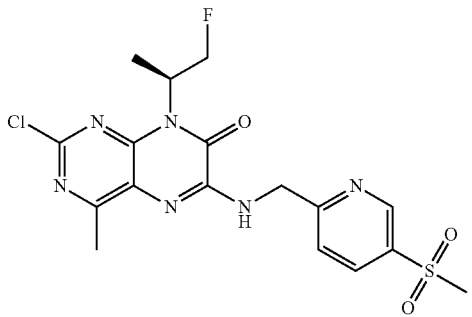 [SMILES: Cc1nc(Cl)nc2c1nc(NCc1ccc(S(C)(=O)=O)cn1)c(=O)n2[C@@H](C)CF] | 2 | 441.6 |

TABLE 2-continued

| Intermediate | Structure | Synthetic Method | m/z [M + H]+ |
|---|---|---|---|
| KK | 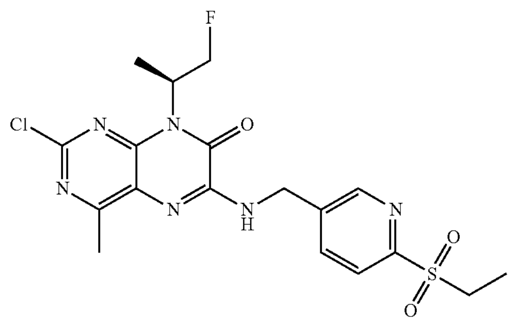 [SMILES: CCS(=O)(=O)c1ccc(CNc2nc3c(C)nc(Cl)nc3n([C@@H](C)CF)c2=O)cn1] | 2 | 455.6 |
| LL | 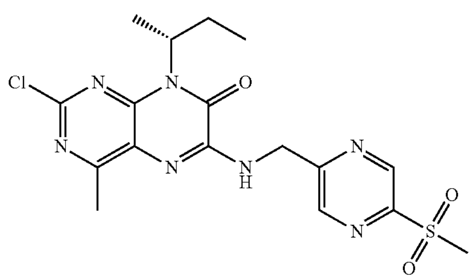 [SMILES: CC[C@@H](C)n1c(=O)c(NCc2cnc(S(C)(=O)=O)cn2)nc2c(C)nc(Cl)nc21] | 1 | 438.1 |
| MM | 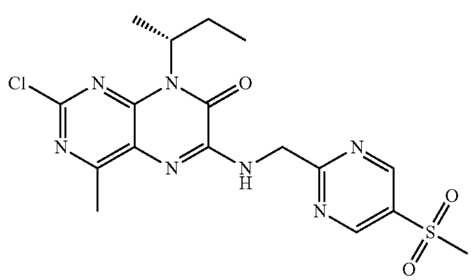 [SMILES: CC[C@@H](C)n1c(=O)c(NCc2ncc(S(C)(=O)=O)cn2)nc2c(C)nc(Cl)nc21] | 1 | 438.1 |
| NN | 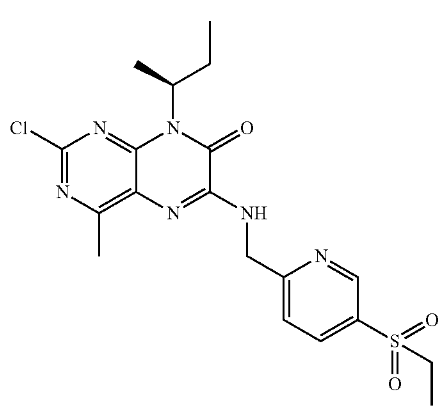 [SMILES: CC[C@H](C)n1c(=O)c(NCc2ccc(S(=O)(=O)CC)cn2)nc2c(C)nc(Cl)nc21] | 2 | 451.1 |

TABLE 2-continued

| Intermediate | Structure | Synthetic Method | m/z [M + H]+ |
|---|---|---|---|
| OO | 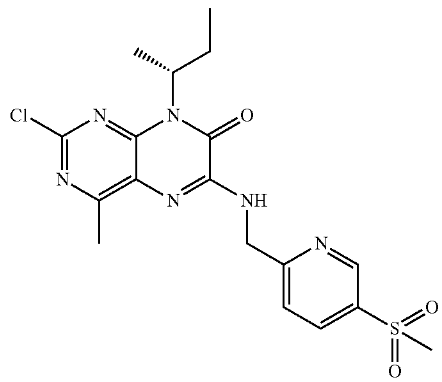 [SMILES: CC[C@@H](C)n1c(=O)c(NCc2ccc(S(C)(=O)=O)cn2)nc2c(C)nc(Cl)nc21] | 1 | 443.1 |
| PP | 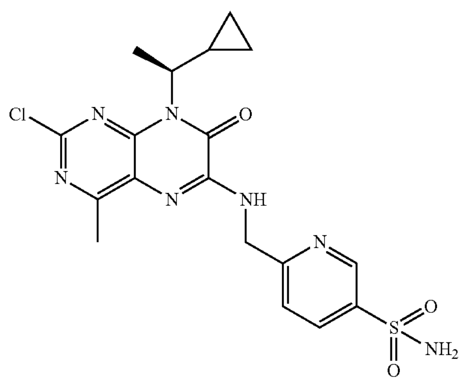 [SMILES: Cc1nc(Cl)nc2c1nc(NCc1ccc(S(N)(=O)=O)cn1)c(=O)n2[C@@H](C)C1CC1] | 2 | 450.2 |
| QQ | 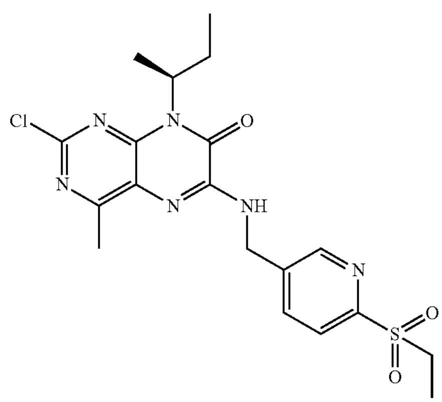 [SMILES: CC[C@H](C)n1c(=O)c(NCc2ccc(S(=O)(=O)CC)nc2)nc2c(C)nc(Cl)nc21] | 2 | 451.1 |
| RR | 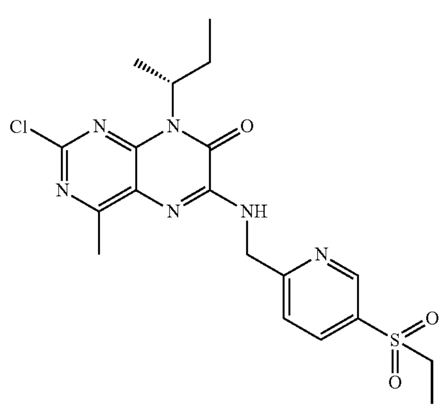 | 1 | 451.1 |

TABLE 2-continued

| Intermediate | Structure | Synthetic Method | m/z [M + H]+ |
|---|---|---|---|
| SS | 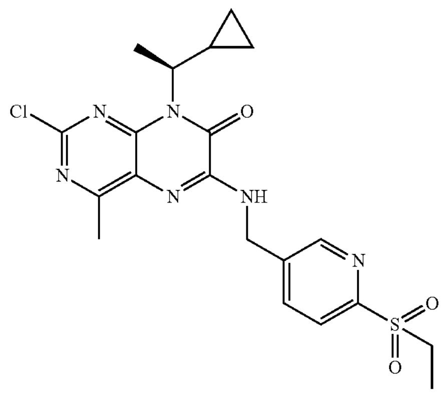 [SMILES: CCS(=O)(=O)c1ccc(CNc2nc3c(C)nc(Cl)nc3n([C@@H](C)C3CC3)c2=O)cn1] | 2 | 463.1 |
| TT | 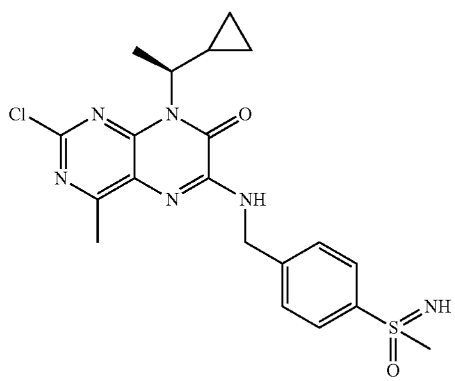 [SMILES: Cc1nc(Cl)nc2c1nc(NCc1ccc(S(C)(=N)=O)cc1)c(=O)n2[C@@H](C)C1CC1] | 2 | 447.2 |
| UU | 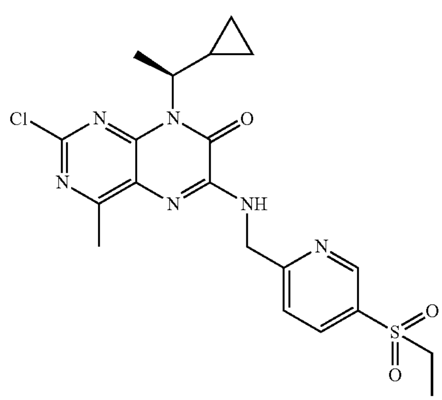 [SMILES: CCS(=O)(=O)c1ccc(CNc2nc3c(C)nc(Cl)nc3n([C@@H](C)C3CC3)c2=O)nc1] | 2 | 463.1 |
| VV | 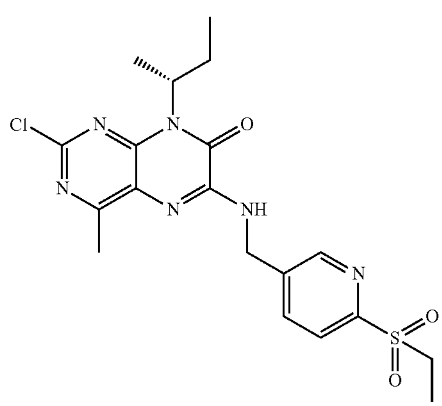 [SMILES: CC[C@@H](C)n1c(=O)c(NCc2ccc(S(=O)(=O)CC)nc2)nc2c(C)nc(Cl)nc21] | 1 | 451.2 |

TABLE 2-continued

| Intermediate | Structure | Synthetic Method | m/z [M + H]+ |
|---|---|---|---|
| WW | 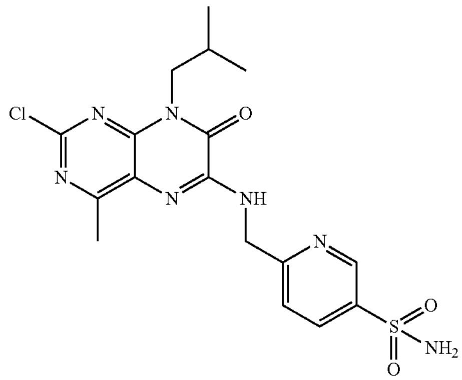 [SMILES: Cc1nc(Cl)nc2c1nc(NCc1ccc(S(N)(=O)=O)cn1)c(=O)n2CC(C)C] | 1 | 437.2 |
| XX | 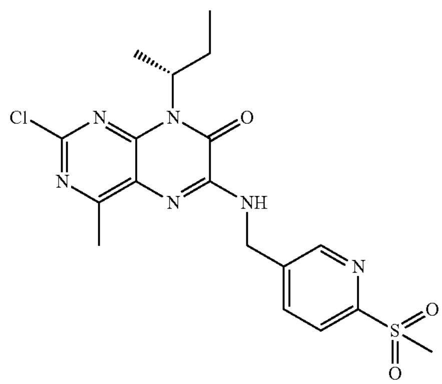 [SMILES: CC[C@@H](C)n1c(=O)c(NCc2ccc(S(C)(=O)=O)nc2)nc2c(C)nc(Cl)nc21] | 1 | 437.1 |
| YY | 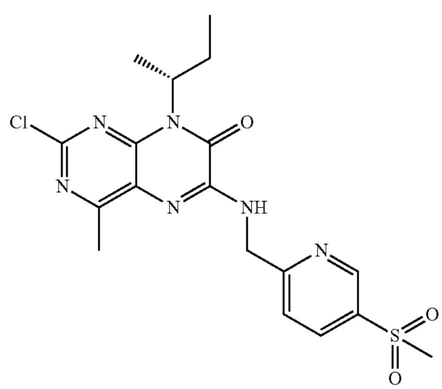 [SMILES: CC[C@@H](C)n1c(=O)c(NCc2ccc(S(C)(=O)=O)cn2)nc2c(C)nc(Cl)nc21] | 1 | 437.1 |
| ZZ | 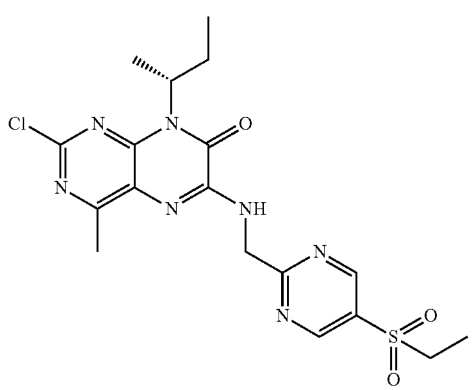 [SMILES: CC[C@@H](C)n1c(=O)c(NCc2ncc(S(=O)(=O)CC)cn2)nc2c(C)nc(Cl)nc21] | 1 | 452.2 |

TABLE 2-continued

| Intermediate | Structure | Synthetic Method | m/z [M + H]+ |
|---|---|---|---|
| AAA | 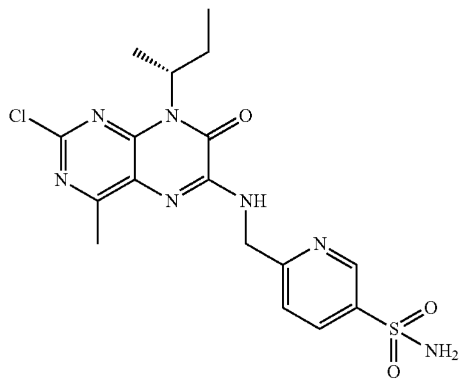 [SMILES: CC[C@@H](C)n1c(=O)c(NCc2ccc(S(N)(=O)=O)cn2)nc2c(C)nc(Cl)nc21] | 1 | 438.1 |
| BBB | 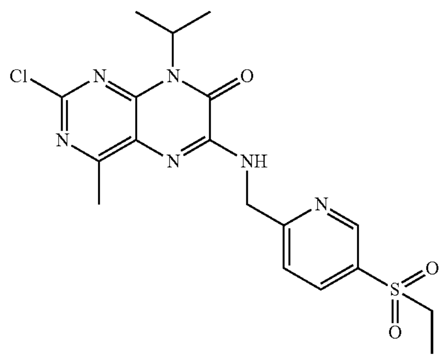 [SMILES: CCS(=O)(=O)c1ccc(CNc2nc3c(C)nc(Cl)nc3n(C(C)C)c2=O)nc1] | 2 | 437.2 |
| CCC | 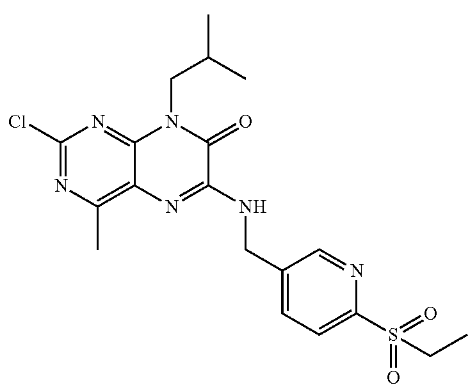 [SMILES: CCS(=O)(=O)c1ccc(CNc2nc3c(C)nc(Cl)nc3n(CC(C)C)c2=O)cn1] | 1 | 451.2 |
| DDD | 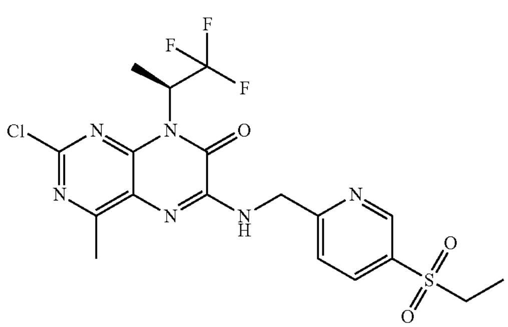 [SMILES: CCS(=O)(=O)c1ccc(CNc2nc3c(C)nc(Cl)nc3n([C@@H](C)C(F)(F)F)c2=O)nc1] | 2 | 491.1 |

TABLE 2-continued

| Intermediate | Structure | Synthetic Method | m/z [M + H]+ |
|---|---|---|---|
| EEE | 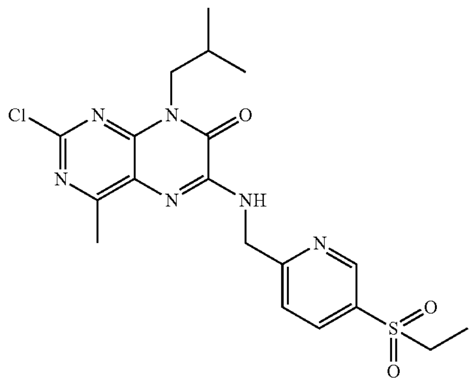 [SMILES: CCS(=O)(=O)c1ccc(CNc2nc3c(C)nc(Cl)nc3n(CC(C)C)c2=O)nc1] | 1 | 451.2 |
| FFF | 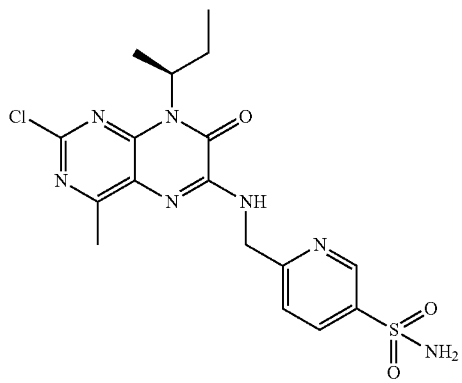 [SMILES: CC[C@H](C)n1c(=O)c(NCc2ccc(S(N)(=O)=O)cn2)nc2c(C)nc(Cl)nc21] | 2 | 438.1 |
| GGG | 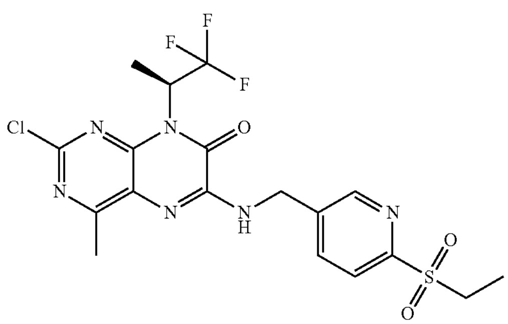 [SMILES: CCS(=O)(=O)c1ccc(CNc2nc3c(C)nc(Cl)nc3n([C@@H](C)C(F)(F)F)c2=O)cn1] | 2 | 491.1 |
| HHH | 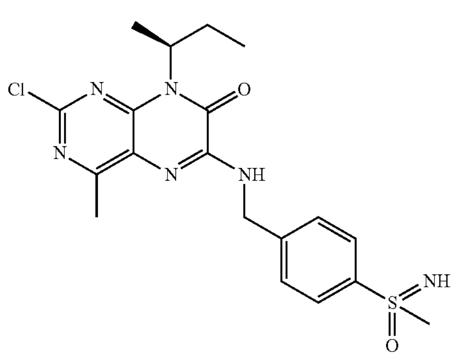 [SMILES: CC[C@H](C)n1c(=O)c(NCc2ccc(S(C)(=N)=O)cc2)nc2c(C)nc(Cl)nc21] | 2 | 434.9 |

TABLE 2-continued

| Intermediate | Structure | Synthetic Method | m/z [M + H]+ |
|---|---|---|---|
| III | 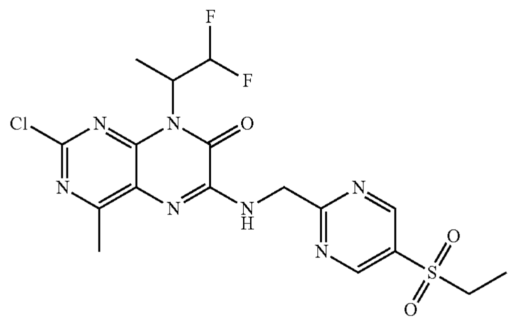 [SMILES: CCS(=O)(=O)c1cnc(CNc2nc3c(C)nc(Cl)nc3n(C(C)C(F)F)c2=O)nc1] | 2 | 474.2 |
| JJJ | 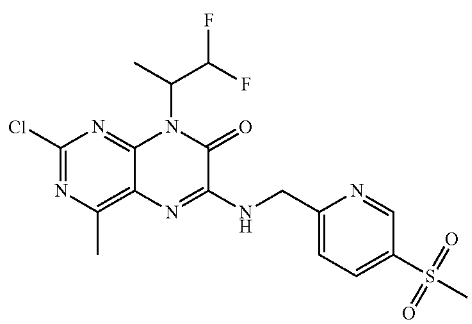 [SMILES: Cc1nc(Cl)nc2c1nc(NCc1ccc(S(C)(=O)=O)cn1)c(=O)n2C(C)C(F)F] | 2 | 459.2 |
| KKKa | 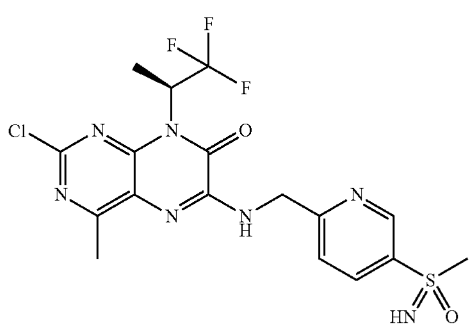 [SMILES: Cc1nc(Cl)nc2c1nc(NCc1ccc(S(C)(=N)=O)cn1)c(=O)n2[C@@H](C)C(F)(F)F] | 2 | 475.1 |
| KKKb | 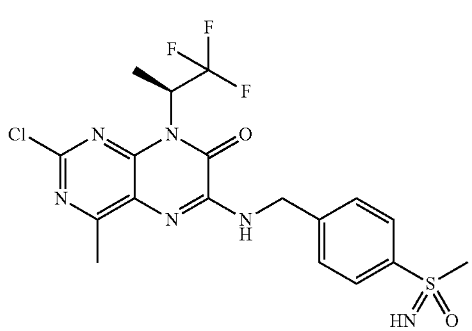 [SMILES: Cc1nc(Cl)nc2c1nc(NCc1ccc(S(C)(=N)=O)cc1)c(=O)n2[C@@H](C)C(F)(F)F] | 2 | 475.1 |

TABLE 2-continued
| Intermediate | Structure | Synthetic Method | m/z [M + H]+ |
|---|---|---|---|
| MMM | 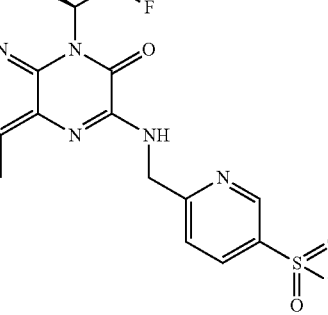 | 2 | 478.1 |
| NNN | 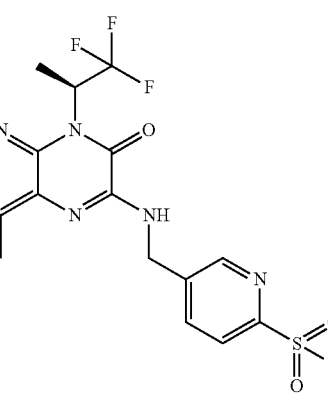 | 2 | 478.1 |
| OOOa | 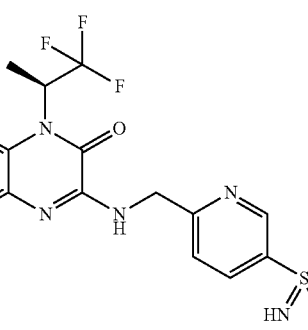 | 2 | 490.1 |
| OOOb | 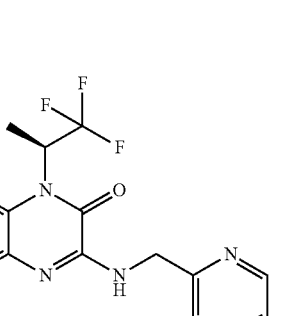 | 2 | 490.2 |

TABLE 2-continued

| Intermediate | Structure | Synthetic Method | m/z [M + H]+ |
|---|---|---|---|
| QQQa | (structure) | 2 | 476.1 |
| QQQb | (structure) | 2 | 476.2 |

Final compounds 1-106b are prepared from the appropriate intermediate, above by coupling with the appropriate pyrimidine boronic acid intermediate, as described in Methods 13-15 or by modification of $R^5$ on another final product as illustrated by Methods 16 and 19.

Biological Activity

The compounds of the present invention have activity as modulators of RORγ (retinoid acid receptor-related orphan receptor γ).

Reporter Gene Assay (RGA)

A nuclear receptor transactivation assay is performed to quantitate the ability of test compounds to inhibit RORγ transactivation of a luciferase reporter. A similar assay is described in: Khan et al., Bioorganic & Medicinal Chemistry Letters 23 (2013), 532-536. The system uses transiently transfected HEK 293 cells cotransfected with two plasmids (pGL4.3, luc2P/GAL4UAS/Hygro, and pBIND, Gal4DBD hRORC LBD1-3). The positive control is co-transiently transfected with both plasmids, and the negative control contains the pGL4.3 promoter sequence. Assays are assembled in 384 well plates where transiently transfected cells and test compound at varying concentrations are incubated for 20-24 h. The next day, assays plates are taken out and equilibrated at RT for 20-30 minutes. Bright-Glo™ Luciferase Assay System is used to detect Luciferase production. After addition of Bright GLO detection reagent, the plates are incubated at RT for 20 minutes. The plates are read on an Envision plate reader to measure luminescence signal. The RLU signal is converted to POC relative to control and blank wells.

Cell Seeding Media:
RPMI 1640-Invitrogen #11875135), 2.5% FBS-Invitrogen #26140, IxPenicillin-Streptomycin-Gibco #15140

Compound Dilution Buffer:
1×HBSS-Invitrogen #14025126
Assay Plates: Greiner #781080-020
Bright Glo Luciferase Assay System: Promega #E2620
Thaw lysis buffer provided in kit, add 100 mL lysis buffer to substrate powder.

Table 3 presents the results obtained when the compounds of the present invention were tested in the above assay, demonstrating their activity as modulators of RORγ. Table 3 also shows data from the metabolic stability assay in human liver microsomes, described below.

Assessment of Metabolic Stability

The 5 time point, high-throughput human liver microsome (HLM) metabolic stability assay is designed to determine in vitro compound metabolism. Compounds are incubated with HLMs at a concentration of 1 uM, at 37° C., for a total of 60 min. The percent of compound remaining at 5, 15, 30, and 60 min is used to calculate the t1/2 (min), $CL_{int}$ (mL/min/kg), $CL_h$ (mL/min/kg), and % $Q_h$. The assay is based on a 96-well format and can accommodate up to 92 compounds per plate (n=1).

Using the 96-well multi-channel head, the Biomek FX, equipped with a Peltier heating block/shaker, is programmed to accomplish the following steps:
1. Pipette 175 uL of 1.15 mg/mL microsomes into each of the 96 conical inserts (Analytical Sales and Products, catalog number 96PL05) that fit into the plate of the Peltier heating block/shaker (the incubation plate)
2. Add 5 uL of compounds from the assay plate to the microsomes and shake the mixture at 600 rpm at 42.1° C. for 10 min (a setting of 42.1° C. on the Peltier is required for the samples to incubate at 37° C.)
3. After 10 min, prompt the user to add the NADPH plate to the deck and add 20 uL from the NADPH plate to the incubation plate to start the reaction 4. Add 215 uL of 100%, cold acetonitrile containing an internal standard(s) to a 0 minute, 5 minute, 15 minute, 30 minute, and 60 minute "quench" plate
5. At 0 min, 5 min, 15 min, 30 min, and 60 min into the incubation, aspirate 12 uL from the incubation mixture and add it to the quench solution to stop the reaction
6. Add 185 uL HPLC grade water to each well of the 0, 5, 15, 30 and 60 minute quench plates to dilute compounds to the appropriate concentration for the mass spectrometer After all time points are collected, the quench plates are sealed with 96-well pierceable plate mats or heat sealing foil and centrifuged at 3000 rpm for 15 min to pellet the microsomes.

The plates are analyzed using LC/MS/MS with electron spray ionization (ESI) and the previously determined MRM transitions. The LC method includes the following parameters:

Injection volume: 5 uL
Mobile Phases: 0.1% Formic Acid in Water (A) and 0.1% Formic Acid in Acetonitrile (B) (HPLC grade)
Left and Right Temperature: 35° C.
Run Time: 4.0 min
Column: Thermo Scientific, Aquasil C18, 50×2.1 mm, 5a, part number 77505-052130, or equivalent
LC Pump Gradient:

| Total Time (min) | Flow Rate (uL/min) | % A | % B |
|---|---|---|---|
| 0 | 500 | 90.0 | 10.0 |
| 0.5 | 500 | 90.0 | 10.0 |
| 1.5 | 500 | 1.0 | 99.0 |
| 2.5 | 500 | 1.0 | 99.0 |
| 3.3 | 500 | 90.0 | 10.0 |
| 4.0 | 500 | 90.0 | 10.0 |

If peak shape is poor and cannot be integrated properly, the following LC method can be used:

Injection volume: 5 uL
Mobile Phases: 2.5 mM Ammonium Bicarbonate (A) and 100% Acetonitrile (B) (HPLC grade)
Aqueous Wash: 90% Water, 10% Acetonitrile (HPLC grade)
Organic Wash: 90% Acetonitrile, 10% Water (HPLC grade)
Left and Right Temperature: 35° C.
Run Time: 4.5 min
Column: Phenomex Luna 3u C18(2) 100A, 50×2.00 mm
LC Pump Gradient:

| Total Time (min) | Flow Rate (uL/min) | % A | % B |
|---|---|---|---|
| 0 | 500 | 90.0 | 10.0 |
| 0.5 | 500 | 90.0 | 10.0 |
| 1.5 | 500 | 1.0 | 99.0 |
| 2.5 | 500 | 1.0 | 99.0 |
| 3.30 | 500 | 90.0 | 10.0 |
| 4.50 | 500 | 90.0 | 10.0 |

Using an Excel template in Activitybase, the peak areas corresponding to 5, 15, 30 and 60 min are compared to the peak area at 0 min to calculate the percent of remaining compound using the following equation:

Percent compound remaining=(AUC at Time t min/AUC at Time 0 min)×100 where t=0, 5, 15, 30 or 60 min.

Time (min) is plotted against the natural logarithm (Ln) of the percent compound remaining to determine the slope. The slope is used to calculate t1/2 (min) using the equation, t1/2=0.693/slope.

Clint, Intrinsic Clearance
 0.693/t1/2*Avg liver wt in g/avg body wt in kg*f(u)/ protein concentration in incubation in mg/mL*mg microsomal protein/g liver
 0.693/t1/2*26 g/kg*1/1.0 mg/mL*45 mg/g
Clh, Hepatic Clearance
 Hepatic flow*f(u)*Clint/(hepatic flow+f(u)*Clint)
Qh, % Hepatic Blood Flow
 (Clh/Hepatic flow)*100

$IC_{50}$ data in RORγ Reporter Gene Assay (RGA) and Metabolic stability data (% Qh) for compounds from Table 1 are shown in Table 3 below. Preferred compounds have % Qh values of less than 24.

TABLE 3

| Example | RGA $IC_{50}$ (nM) | HLM (% Qh) |
|---|---|---|
| 1 | 200 | <24 |
| 2 | 110 | <24 |
| 3 | 88 | <24 |
| 4 | 180 | <24 |
| 5 | 73 | 28 |
| 6 | 87 | <24 |
| 7 | 70 | 33 |
| 8 | 75 | <24 |
| 9 | 70 | <24 |
| 10 | 97 | 27 |
| 11 | 135 | 26 |
| 12 | 140 | <24 |
| 13 | 99 | <24 |
| 14 | 115 | <24 |
| 15 | 150 | <24 |
| 16 | 113 | <24 |
| 17 | 130 | 39 |
| 18 | 175 | 55 |
| 19 | 165 | 62 |
| 20 | 175 | 29 |
| 21 | 1900 | <24 |
| 22 | 140 | <24 |
| 23 | 178 | <24 |
| 24 | 120 | 69 |
| 25 | 155 | 26 |
| 26b | 170 | 25 |
| 27b | 265 | <24 |
| 26a | 109 | 25 |
| 29a | 235 | 73 |
| 29b | 170 | 48 |
| 31 | 850 | 55 |
| 27a | 210 | <24 |
| 33 | 100 | 41 |
| 34a | 210 | 25 |
| 34b | 170 | <24 |
| 36b | 245 | <24 |
| 37 | 455 | <24 |
| 38a | 160 | <24 |
| 38b | 110 | <24 |
| 36a | 260 | <24 |
| 41 | 1250 | <24 |
| 42b | 390 | <24 |
| 43a | 730 | <24 |
| 43b | 400 | <24 |
| 42a | 270 | <24 |
| 46 | 1050 | 66 |
| 47 | 1050 | 56 |
| 48 | 1205 | <24 |
| 49 | 4200 | <24 |
| 50 | 2700 | <24 |
| 51 | 230 | <24 |
| 52 | 335 | <24 |
| 53 | 160 | 33 |
| 54 | 225 | 41 |
| 55 | 265 | <24 |
| 56 | 1100 | <24 |
| 57 | 500 | <24 |
| 58 | 71 | <24 |
| 59 | 98 | 78 |

TABLE 3-continued

| Example | RGA IC$_{50}$ (nM) | HLM (% Qh) |
|---|---|---|
| 60 | 80 | <24 |
| 61 | 185 | <24 |
| 62 | 125 | 27 |
| 63 | 100 | <24 |
| 64 | 95 | <24 |
| 65 | 135 | <24 |
| 66 | 64 | 25 |
| 67 | 110 | <24 |
| 68 | 60 | <24 |
| 69 | 116 | <24 |
| 70 | 1300 | <24 |
| 71 | 65 | 35 |
| 72 | 205 | <24 |
| 73 | 155 | <24 |
| 74 | 77 | <24 |
| 75 | | |
| 76 | 275 | 34 |
| 77 | 680 | <24 |
| 78 | 275 | <24 |
| 79 | 130 | <24 |
| 80 | 255 | <24 |
| 81 | 185 | <24 |
| 82 | 225 | <24 |
| 83 | 250 | 32 |
| 84 | 195 | 33 |
| 85 | 270 | <24 |
| 86 | 73 | <24 |
| 87 | 97 | 37 |
| 88 | 102 | 38 |
| 89 | 225 | <24 |
| 90 | 235 | <24 |
| 91a | 295 | <24 |
| 91b | 255 | <24 |
| 93 | 185 | <24 |
| 94 | 205 | <24 |
| 95 | 150 | 40 |
| 96 | 280 | <24 |
| 97 | 320 | 46 |
| 98 | 1100 | <24 |
| 99a | 230 | 41 |
| 99b | 260 | 41 |
| 101a | 365 | <24 |
| 102a | 535 | <24 |
| 101b | 315 | <24 |
| 102b | 640 | <24 |
| 105a | 890 | <24 |
| 106a | 1300 | <24 |
| 105b | 510 | 27 |
| 106b | 840 | 28 |

Methods of Therapeutic Use

On the basis of their biological properties the compounds of formula (I) according to the invention, or their tautomers, racemates, enantiomers, diastereomers, mixtures thereof and the salts of all the above-mentioned forms are suitable for treating autoimmune and allergic disorders in that they exhibit good modulatory effect upon RORγ.

The present invention is therefore directed to compounds of general formula (I), and the pharmaceutically acceptable salts thereof, and all tautomers, racemates, enantiomers, diastereomers, mixtures thereof, which are useful in the treatment of a disease and/or condition wherein the activity of RORγ modulators is of therapeutic benefit, including but not limited to the treatment of autoimmune or allergic disorders.

Such disorders that may be treated by the compounds of the invention include for example: rheumatoid arthritis, psoriasis, systemic lupus erythromatosis, lupus nephritis, systemic sclerosis, vasculitis, scleroderma, asthma, allergic rhinitis, allergic eczema, multiple sclerosis, juvenile rheumatoid arthritis, juvenile idiopathic arthritis, type I diabetes, Crohn's disease, ulcerative colitis, graft versus host disease, psoriatic arthritis, reactive arthritis, ankylosing spondylitis, atherosclerosis, uveitis and non-radiographic spondyloarthropathy.

For treatment of the above-described diseases and conditions, a therapeutically effective dose will generally be in the range of approximately 0.01 mg to about 10 mg/kg of body weight per dosage of a compound of the invention; preferably, from about 0.1 mg to about 5 mg/kg of body weight per dosage. For example, for administration to a 70 kg person, the dosage range would be approximately 0.7 mg to about 750 mg per dosage of a compound of the invention, preferably from about 7.0 mg to about 350 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and generally comprise at least one compound of the invention and at least one pharmaceutically acceptable carrier. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art. As one of skill in the art would expect, the forms of the

What is claimed is:

1. A compound of formula (I)

(I)

[chemical structure]

wherein:
R¹ is selected from —S(O)$_n$R⁶, —S(O)$_n$NR⁷R⁸, and —S(O)(NH)R⁶;
  wherein:
  R⁶ is:
  $C_{1-3}$ alkyl
  R⁷ and R⁸ are each H; and
  n is 1 or 2;
R² and R³ are independently selected from
$C_{1-3}$ alkyl;
cyclopropyl; and
methoxy;
R⁴ is $C_{1-6}$ alkyl, optionally substituted with one or two groups independently selected from
$C_{3-6}$ cycloalkyl;
halogen;
—CF₃; and
—CN;
R⁵ is selected from
$C_{1-3}$ alkyl, optionally substituted with 1 to 3 fluoro groups;
—CH₂OH;
—CH₂OC(O)$C_{1-3}$ alkyl; and
—O$C_{1-3}$ alkyl;
W is selected from
pyridinyl;
pyrimidinyl;
pyrizinyl;
phenyl; and
piperidinyl;
and the pharmaceutically acceptable salts thereof.

2. The compound of formula (I) according to claim 1, wherein
R¹ is selected from —S(O)$_n$R⁶, —S(O)$_n$NR⁷R⁸, and —S(O)(NH)R⁶;
  wherein:
  R⁶ is $C_{1-3}$ alkyl;
  R⁷ and R⁸ are each H; and
  n is 2;
R² and R³ are independently selected from
methyl;
cyclopropyl; and
methoxy;
R⁴ is $C_{1-4}$alkyl, optionally substituted with one or two groups independently selected from
cyclopropyl;
—F;
—CF₃; and
—CN;
R⁵ is selected from
—CH₃;
—CH₂F;
—CH₂OH;
—CH₂OC(O)CH₃; and
—OCH₃;
W is selected from
2-pyridinyl, 3-pyridinyl, 2-pyrimidinyl, 2-pyrizinyl and phenyl;
and the pharmaceutically acceptable salts thereof.

3. The compound of formula (I) according to claim 1, wherein
R¹ is selected from —S(O)$_n$R⁶, —S(O)$_n$NR⁷R⁸, and —S(O)(NH)R⁶;
  wherein:
  R⁶ is $C_{1-2}$ alkyl;
  R⁷ and R⁸ are each —H; and
  n is 2;
R² and R³ are independently selected from
methyl;
cyclopropyl; and
methoxy;
R⁴ is $C_{1-4}$alkyl, optionally substituted with one or two groups independently selected from
cyclopropyl;
—F;
—CF₃; and
—CN;
R⁵ is selected from
—CH₃;
—CH₂F;
—CH₂OH;
—CH₂OC(O)CH₃; and
—OCH₃;
W is selected from
2-pyridinyl, 3-pyridinyl, 2-pyrimidinyl, 2-pyrizinyl and phenyl;
and the pharmaceutically acceptable salts thereof.

4. The compound of formula (I) according to claim 1, wherein
R¹ is selected from —S(O)$_n$R⁶, —S(O)$_n$NR⁷R⁸, and —S(O)(NH)R⁶;
  wherein:
  R⁶ is $C_{1-2}$ alkyl;
  R⁷ and R⁸ are each —H; and
  n is 2;
R² is methyl or methoxy;
R³ is cyclopropyl;
R⁴ is $C_{1-4}$alkyl, optionally substituted with a group selected from
cyclopropyl and —CF₃;
R⁵ is selected from
—CH₃;
—CH₂F; and
—CH₂OH;
W is selected from
2-pyridinyl, 3-pyridinyl, 2-pyrimidinyl, and phenyl;
and the pharmaceutically acceptable salts thereof.

5. The compound of formula (I) according to claim 1, wherein
R² is methyl or methoxy;
R³ is cyclopropyl;

$R^4$ is $C_{1-4}$alkyl, optionally substituted with a group selected from
cyclopropyl and —$CF_3$;

$R^5$ is —$CH_3$;

W is selected from 2-pyridinyl, 3-pyridinyl, 2-pyrimidinyl, and phenyl;

and the pharmaceutically acceptable salts thereof.

6. The compound of formula (I) according to claim 1, wherein

W is selected from 2-pyridinyl and, 3-pyridinyl;

and the pharmaceutically acceptable salts thereof.

7. The compound according to claim 1 selected from the group consisting of:

1
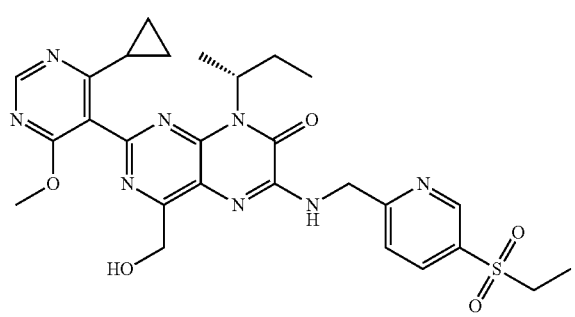

2
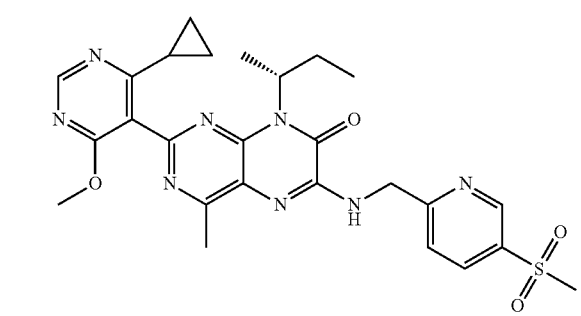

3
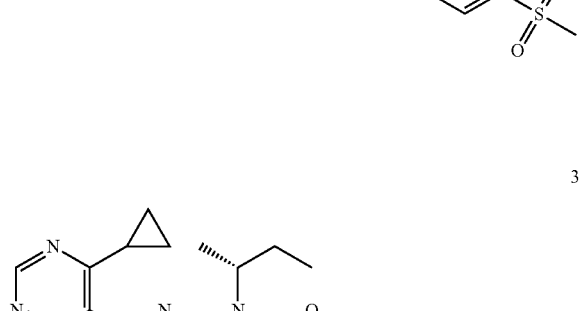

4
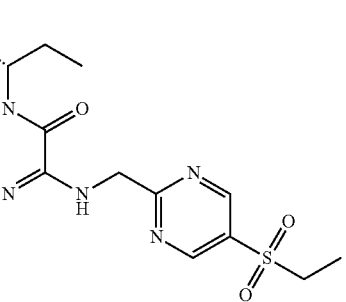

5
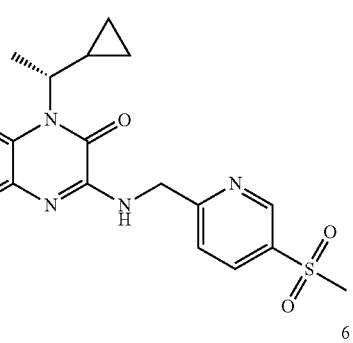

6
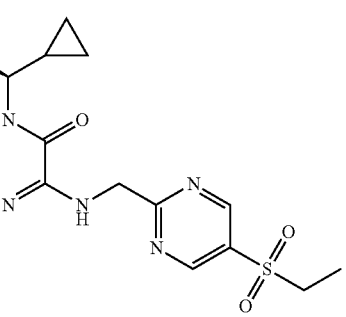

7
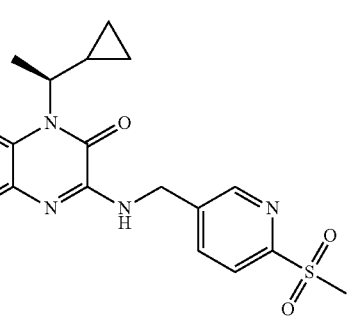

8
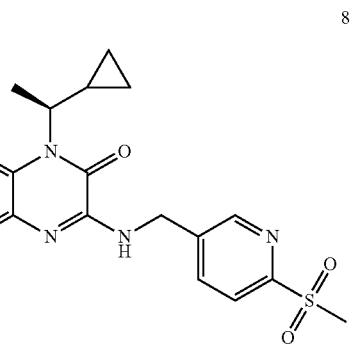

-continued
9
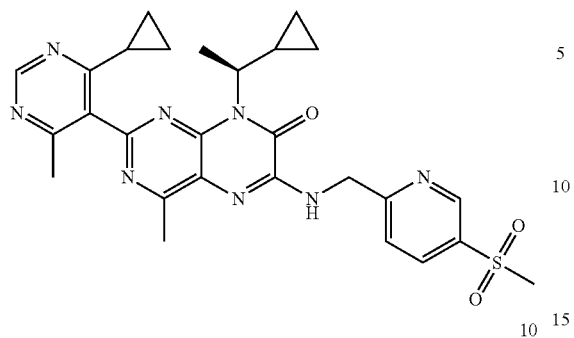
10
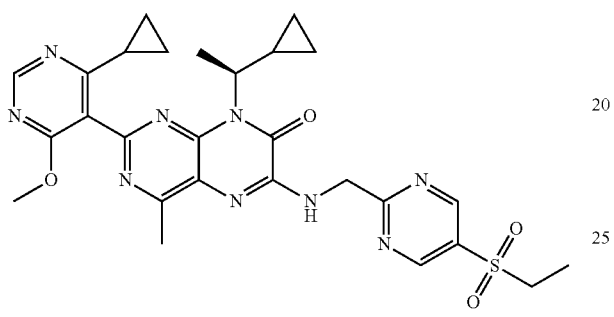
11
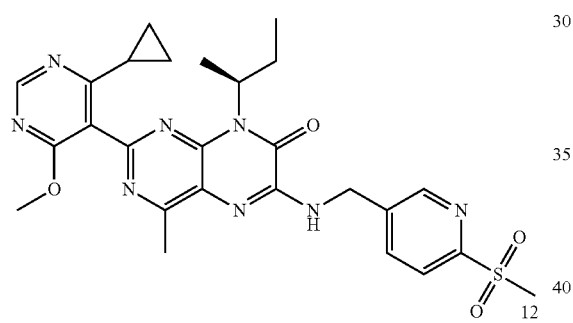
12
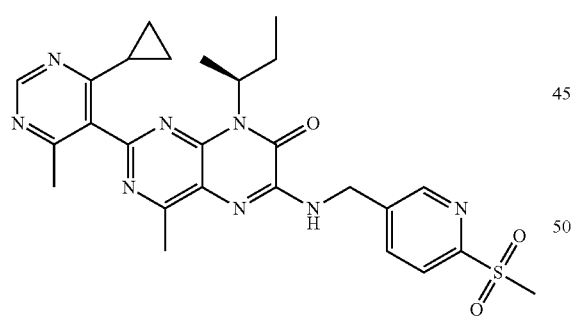
13
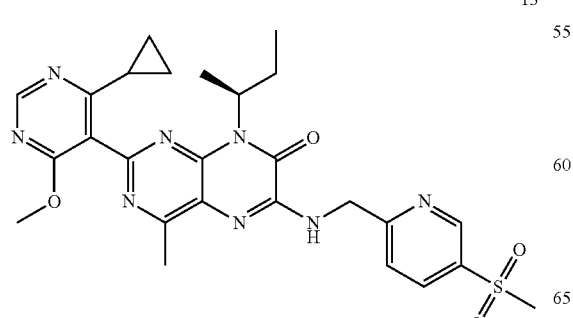
-continued
14
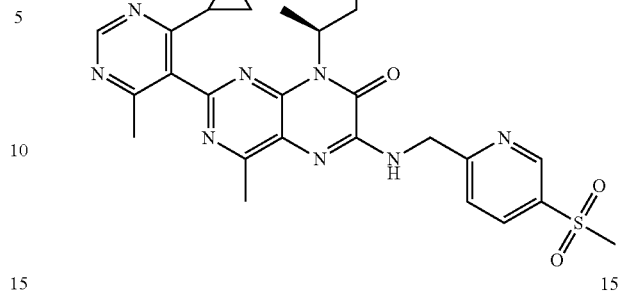
15
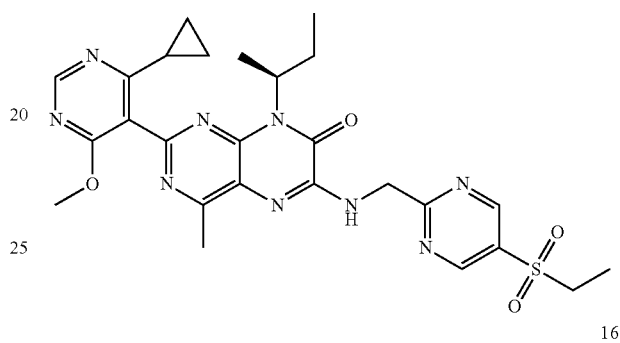
16
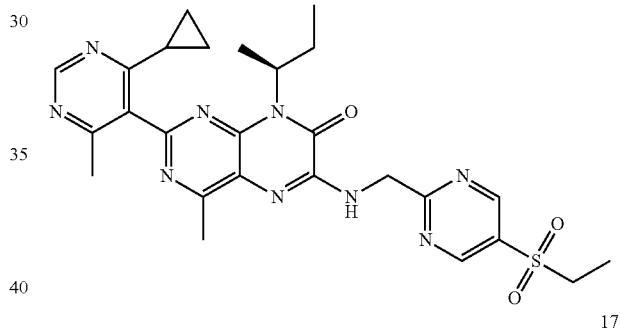
17
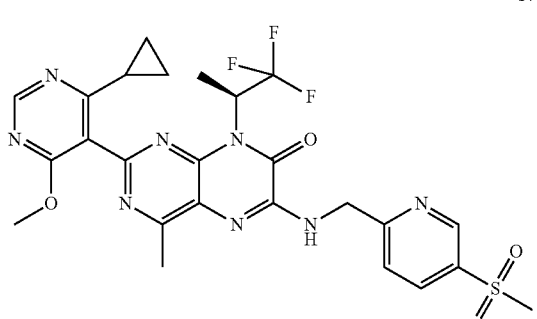
18
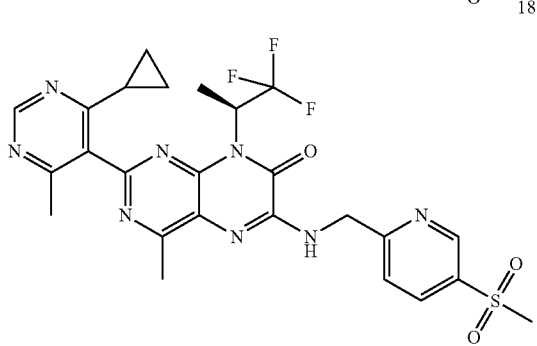

19
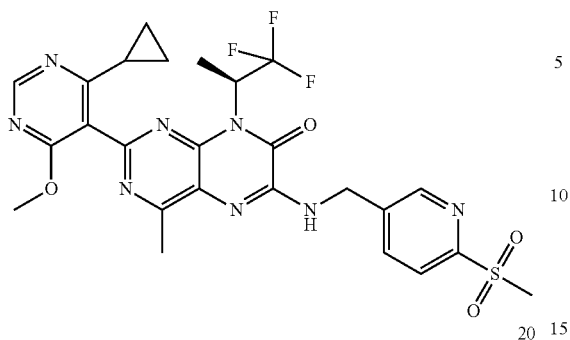
20
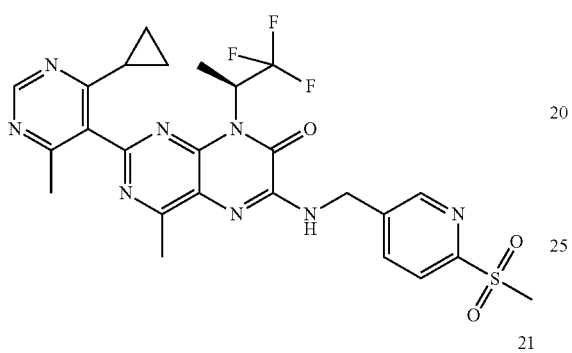
21
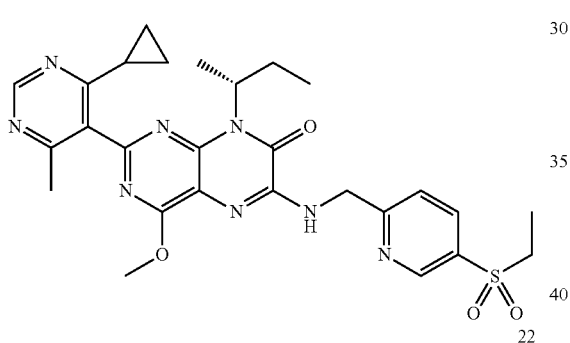
22
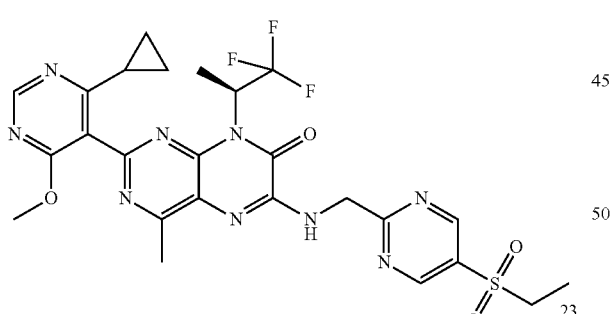
23
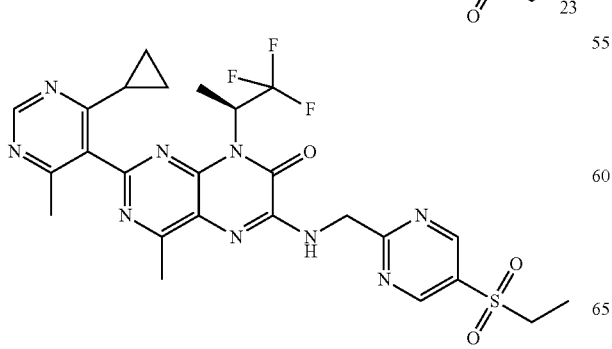
24
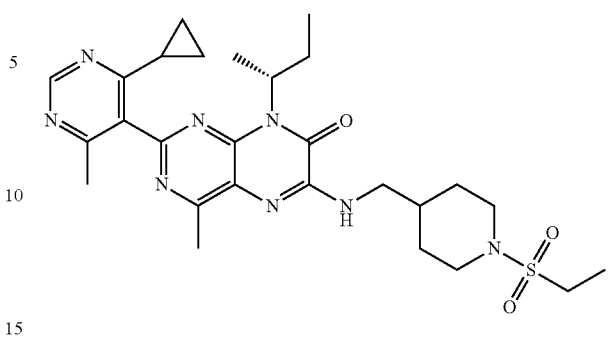
25
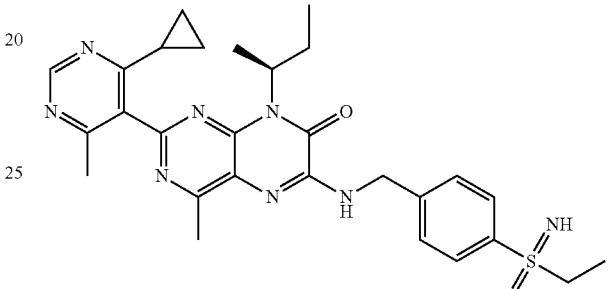
26
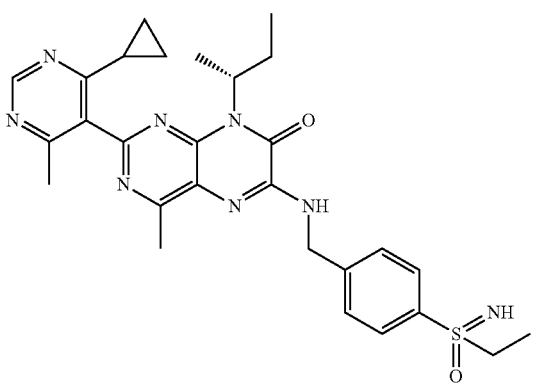
27
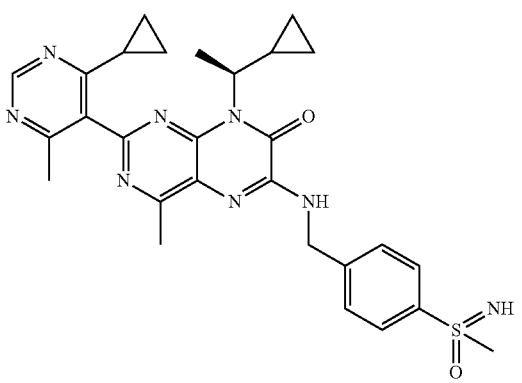

29
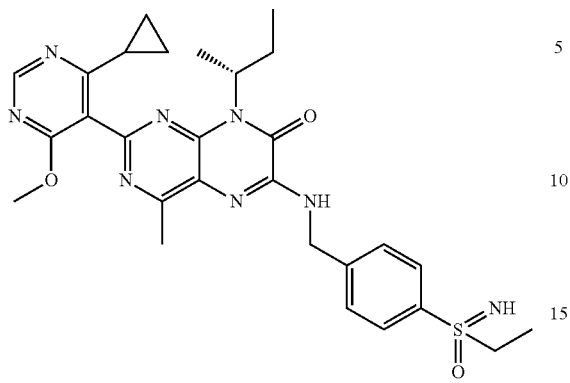
31
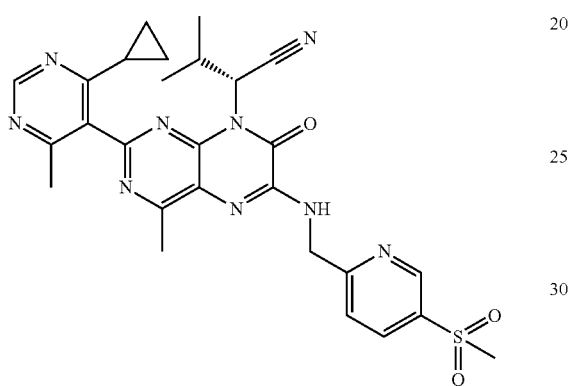
33
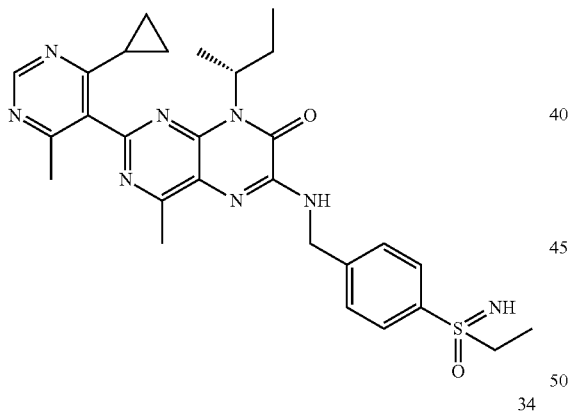
34
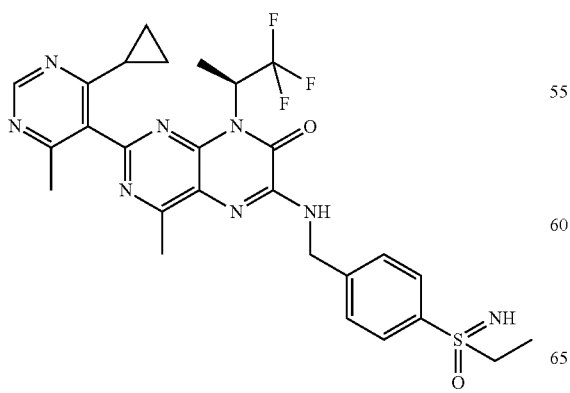
36
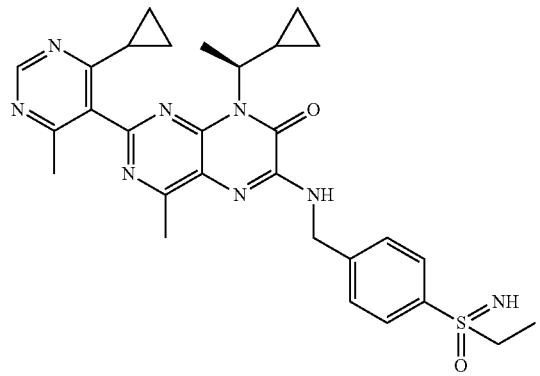
37
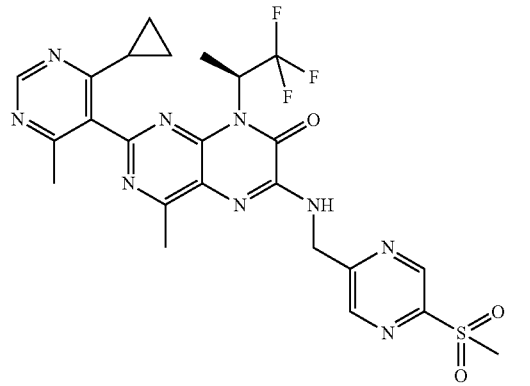
38
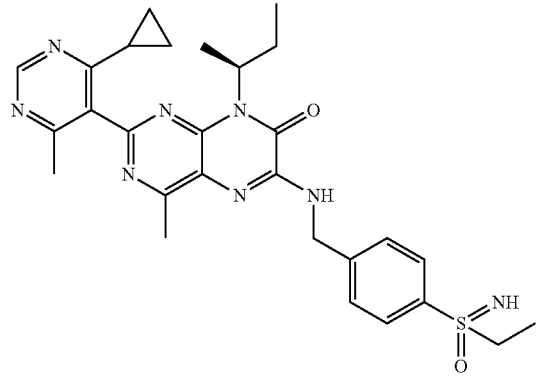
41
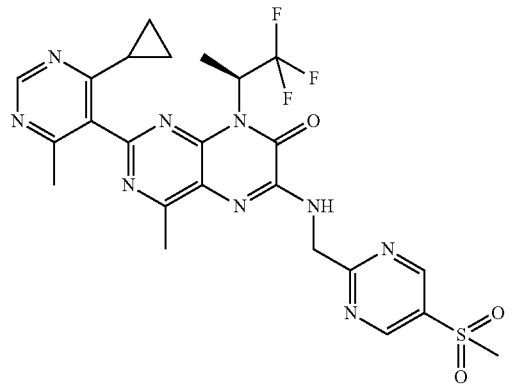

42
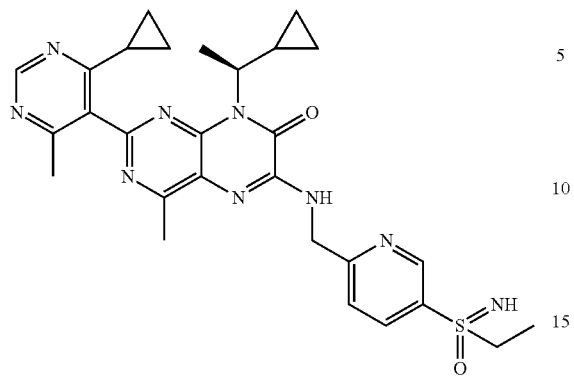
43
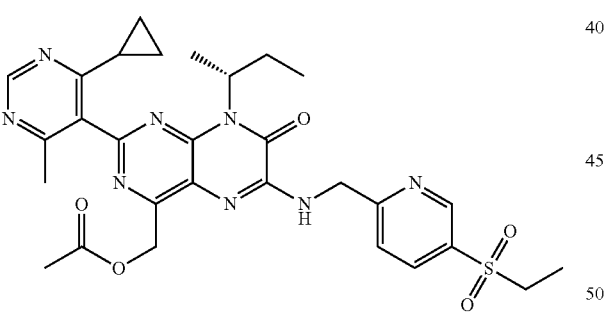
46
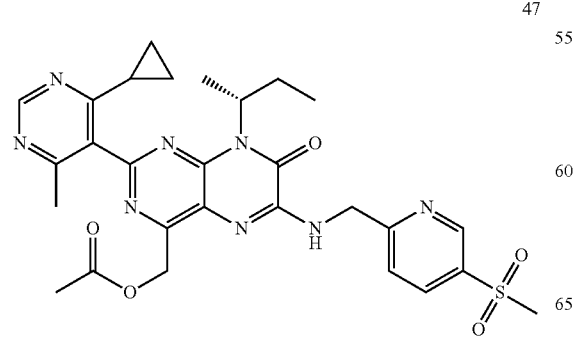
47
48
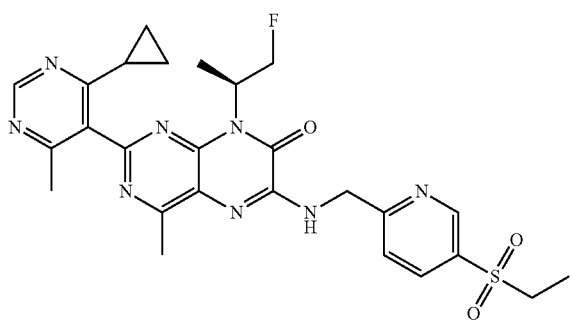
49
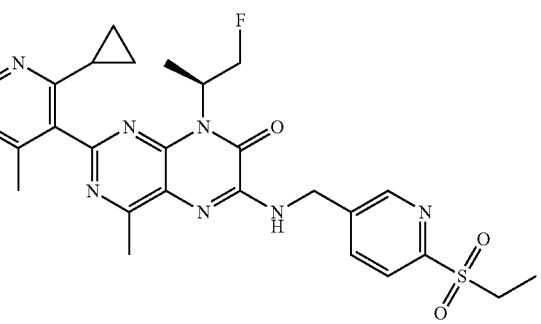
50
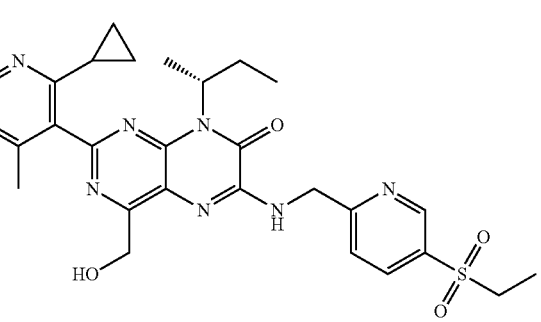
51

52
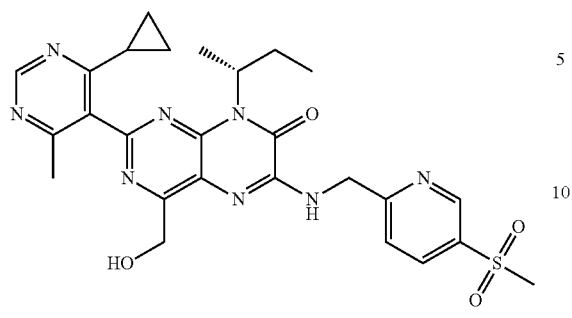
53
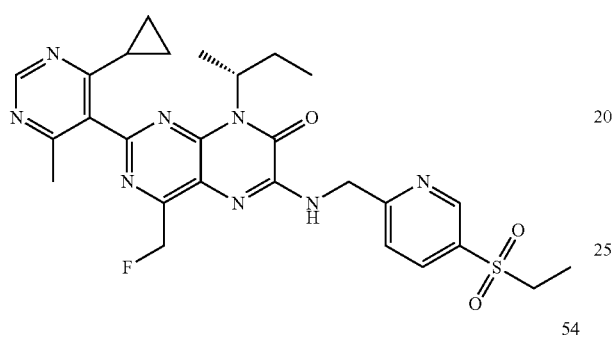
54
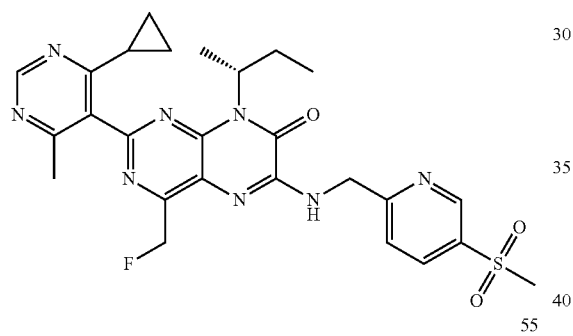
55
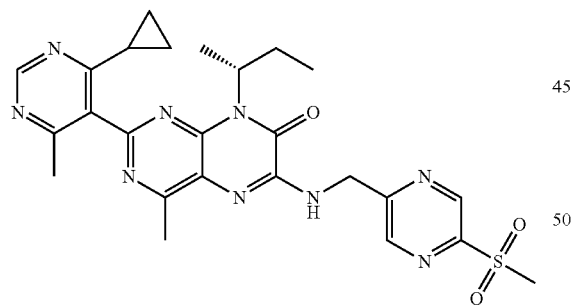
56
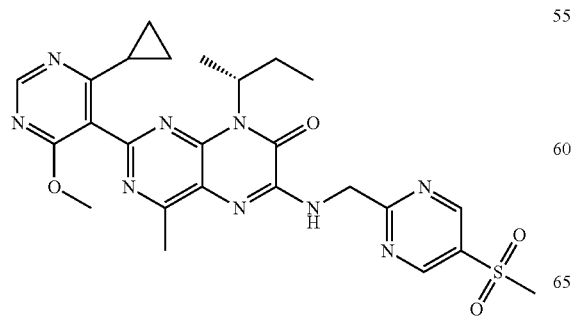
57
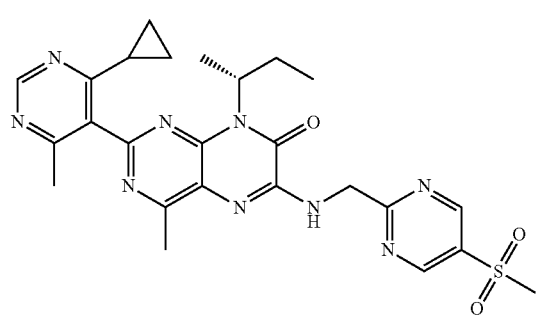
58
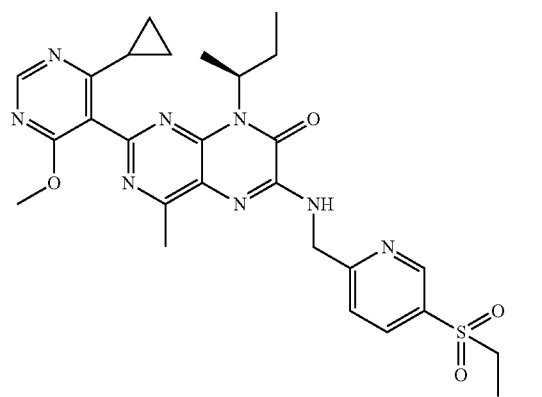
59
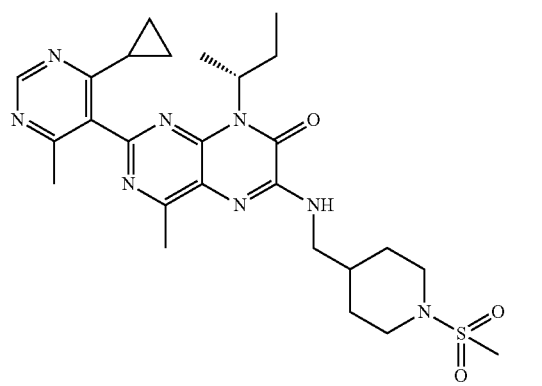
60
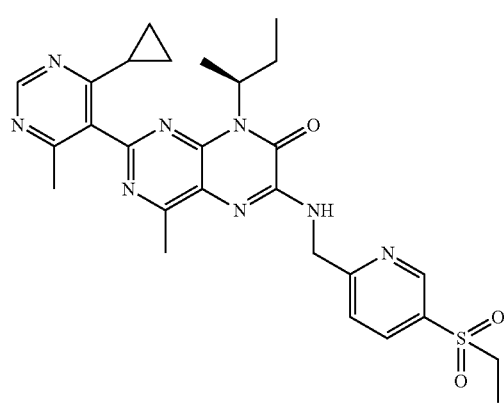

61
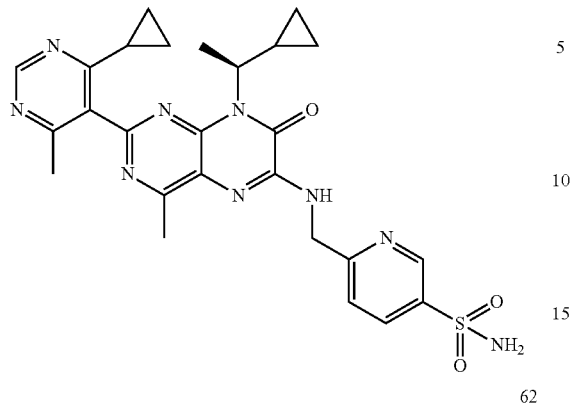
62
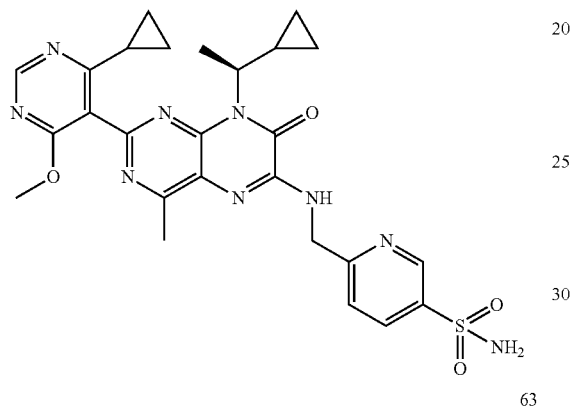
63
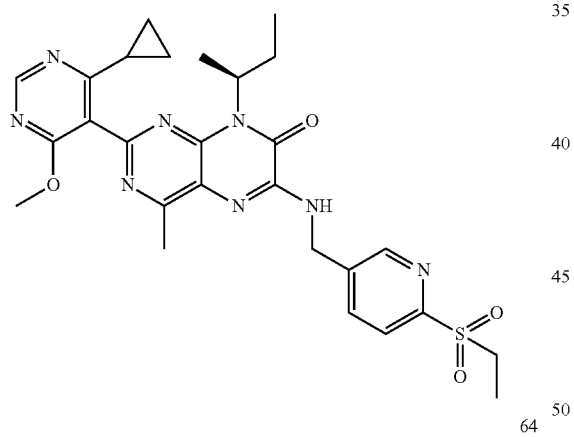
64
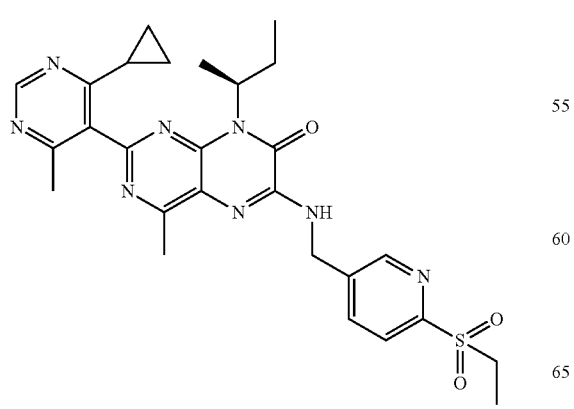
65
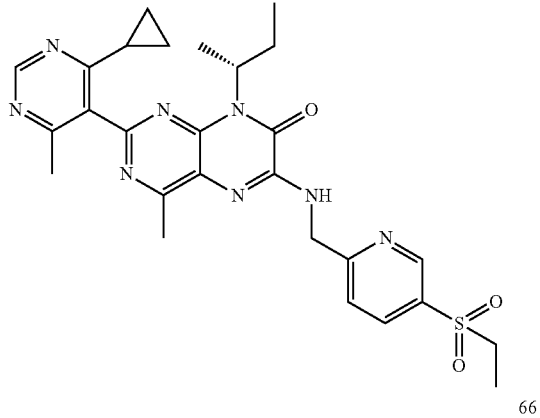
66
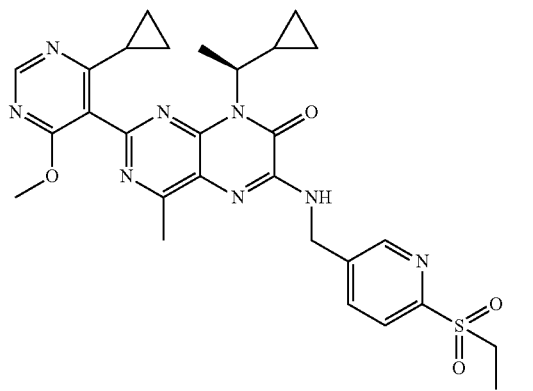
67
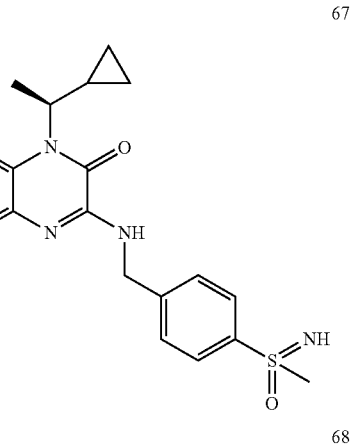
68
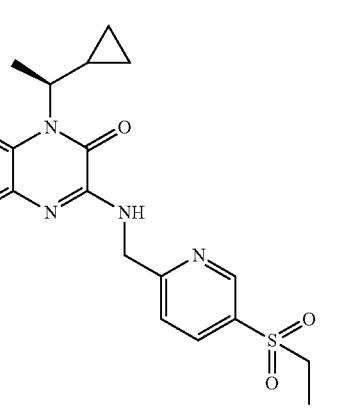

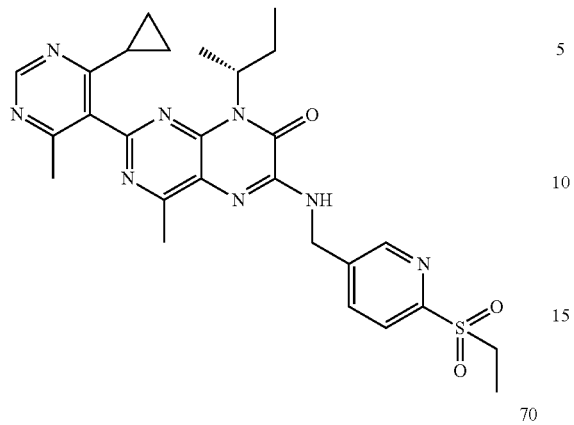
69
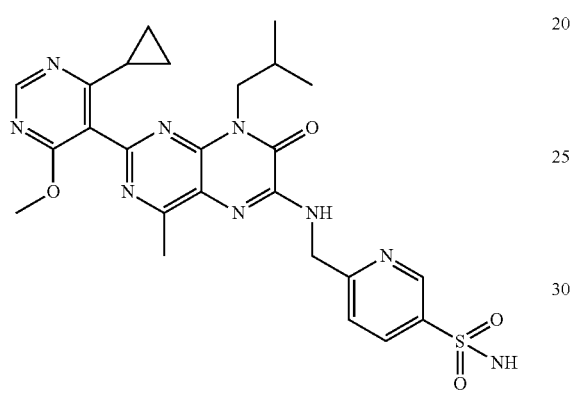
70
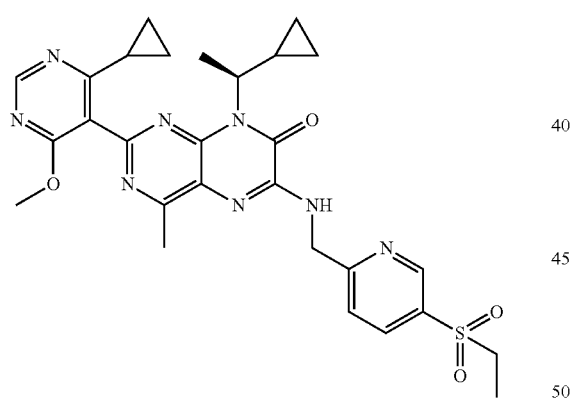
71
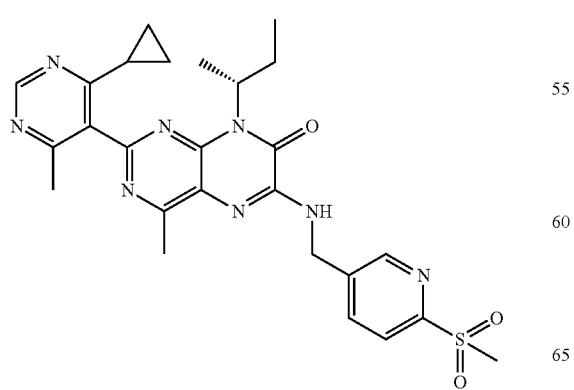
72
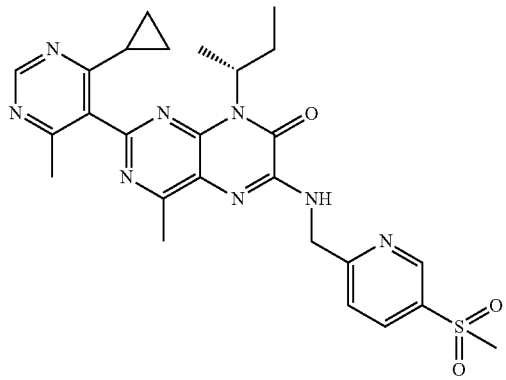
73
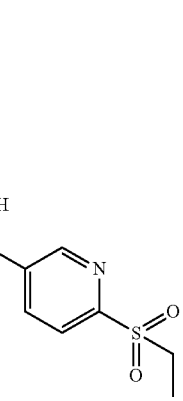
74
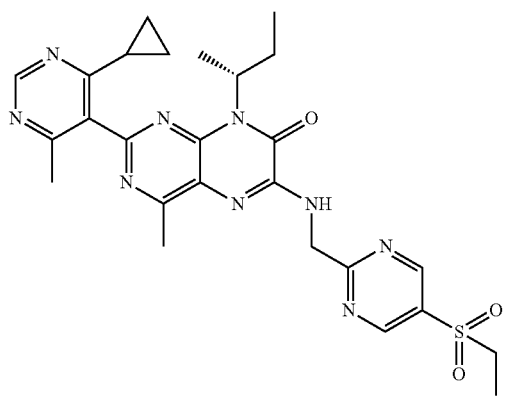
75
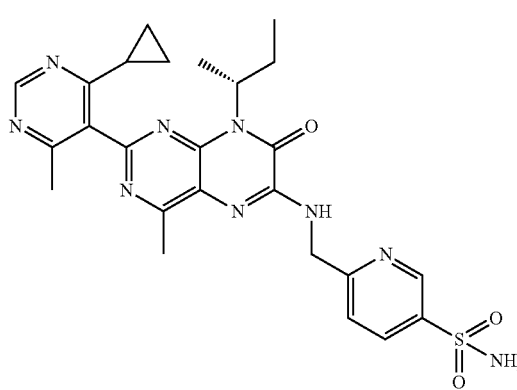
76

-continued

85
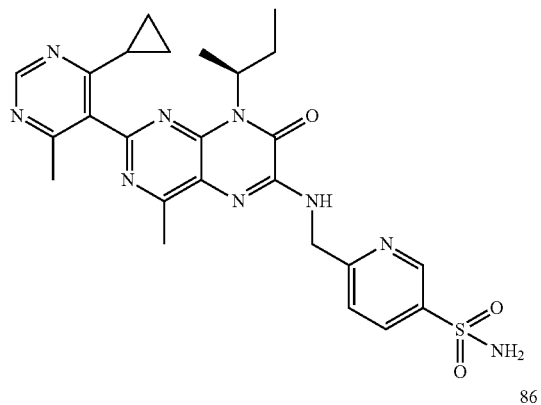
86
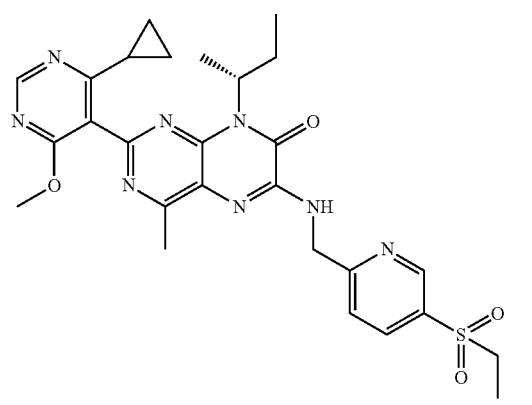
87
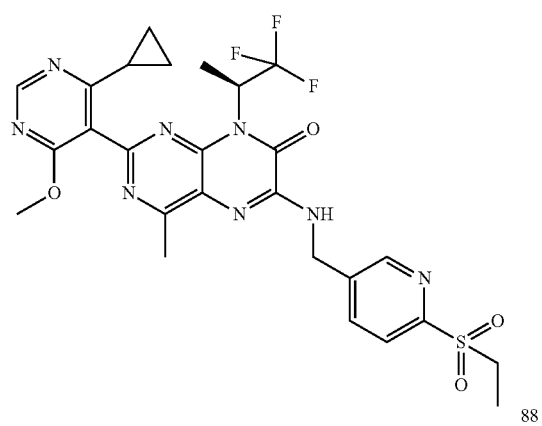
88
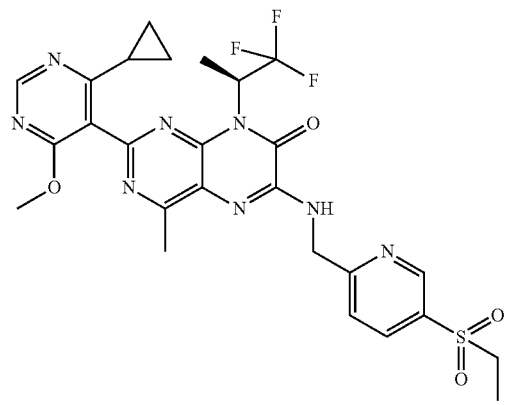
89
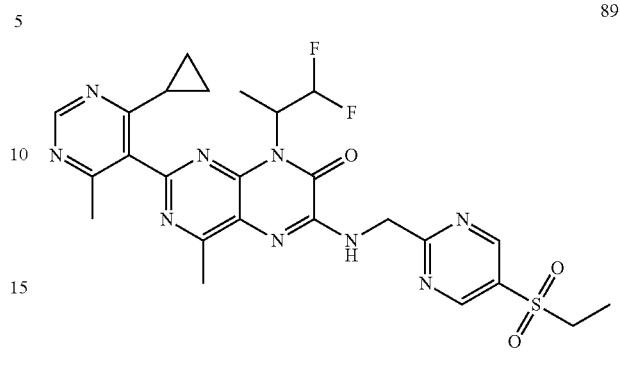
90
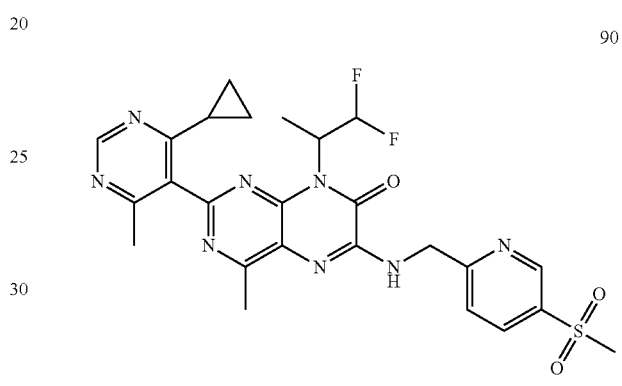
91
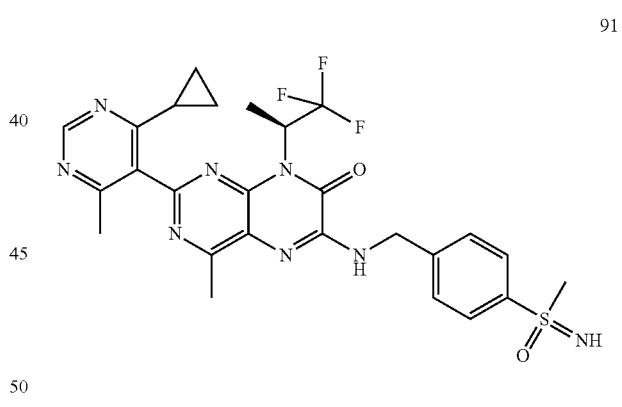
93
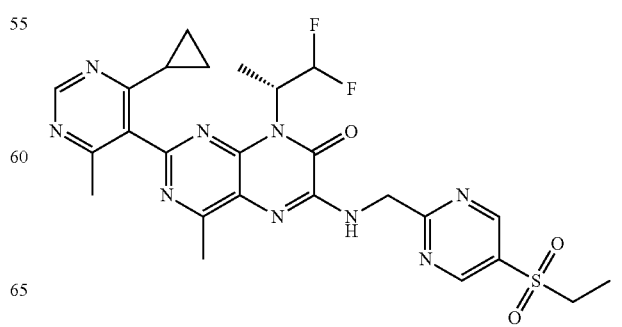

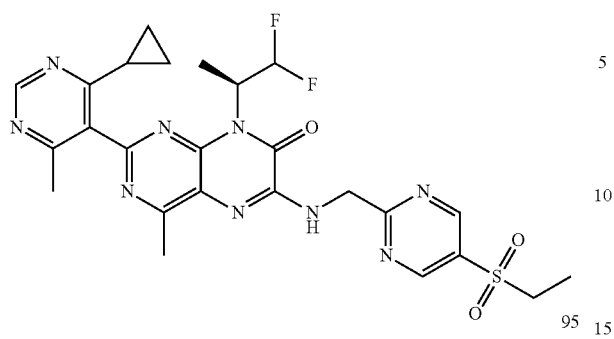
94
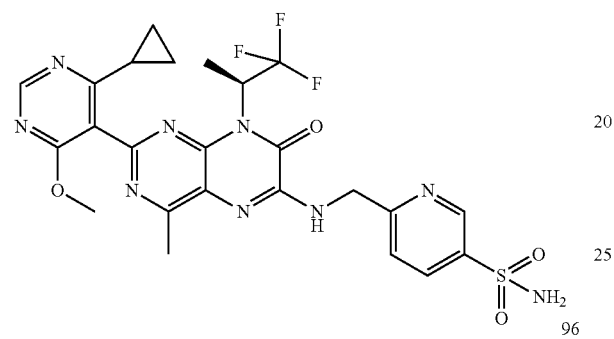
95
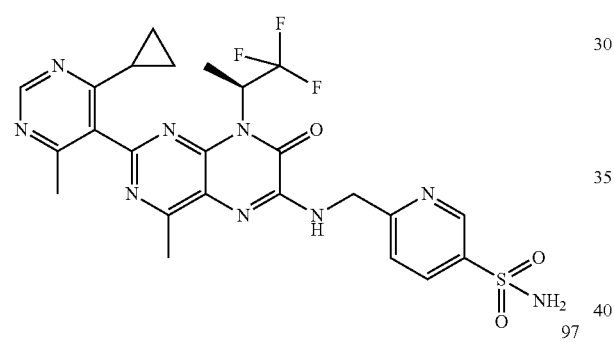
96
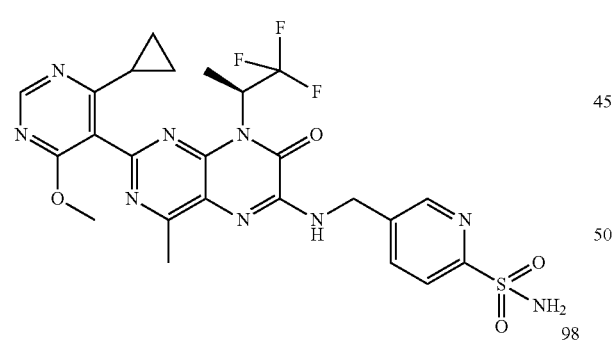
97
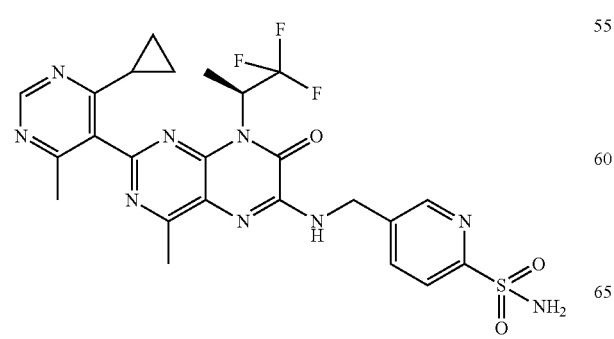
98
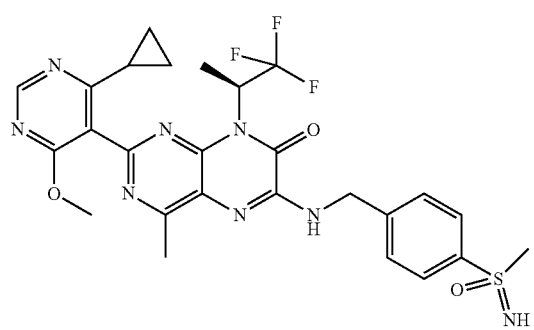
99
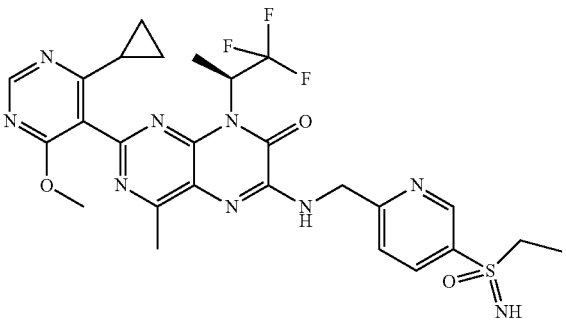
101
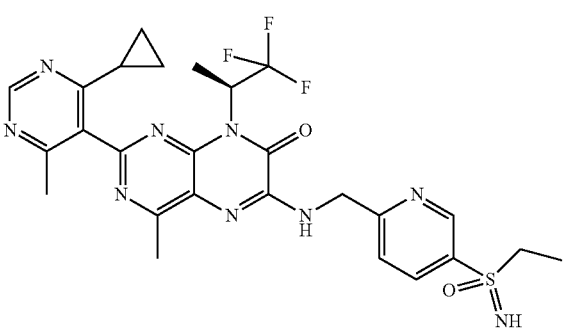
102
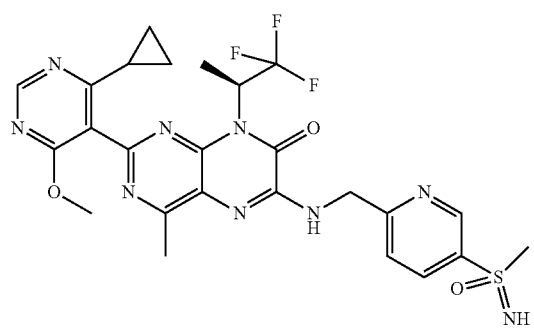
105

-continued

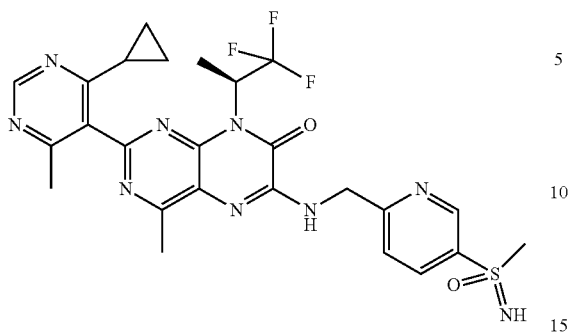

and the pharmaceutically acceptable salts thereof.

8. A pharmaceutical composition comprising a compound according to claim 1 and a pharmaceutically acceptable excipient or carrier.

9. A method for treating an autoimmune disease or allergic disorder wherein the activity of RORγ modulators would be of therapeutic benefit, comprising administering to a patient having such autoimmune disease or allergic disorder a therapeutically effective amount of a compound of formula (I) according to claim 1, or a pharmaceutically acceptable salt thereof.

* * * * *